(12) United States Patent
Albertsen et al.

(10) Patent No.: US 7,915,478 B2
(45) Date of Patent: Mar. 29, 2011

(54) MSCA1 NUCLEOTIDE SEQUENCES IMPACTING PLANT MALE FERTILITY AND METHOD OF USING SAME

(75) Inventors: Marc C. Albertsen, Grimes, IA (US); Tim Fox, Des Moines, IA (US); Mary Trimnell, West Des Moines, IA (US); Yongzhong Wu, Johnston, IA (US); Keith Lowe, Johnston, IA (US); Bailin Li, Hockessin, DE (US); Marianna Faller, Wilmington, DE (US)

(73) Assignees: Pioneer Hi-Bred International, Inc., Johnston, IA (US); E.I. Du Pont de Nemours and Company, Wilmington, DE (US)

( * ) Notice: Subject to any disclaimer, the term of this patent is extended or adjusted under 35 U.S.C. 154(b) by 680 days.

(21) Appl. No.: 11/833,385

(22) Filed: Aug. 3, 2007

(65) Prior Publication Data
US 2009/0038028 A1     Feb. 5, 2009

(51) Int. Cl.
C12N 15/82   (2006.01)
C12N 15/29   (2006.01)
C12N 15/56   (2006.01)
A01H 1/02    (2006.01)

(52) U.S. Cl. ........ 800/274; 800/278; 800/282; 800/287; 435/8; 435/204

(58) Field of Classification Search ........................ None
See application file for complete search history.

(56) References Cited

U.S. PATENT DOCUMENTS

| | | |
|---|---|---|
| 5,409,823 A | 4/1995 | Crossland et al. |
| 5,432,068 A | 7/1995 | Albertsen |
| 5,478,369 A | 12/1995 | Albertsen |
| 5,608,142 A | 3/1997 | Barton |
| 5,689,041 A | 11/1997 | Mariani |
| 5,689,051 A | 11/1997 | Cigan |
| 5,750,867 A | 5/1998 | Williams et al. |
| 5,750,868 A | 5/1998 | Cigan |
| 5,837,850 A | 11/1998 | Huffman |
| 5,859,341 A | 1/1999 | Albertsen |
| 5,880,331 A | 3/1999 | Krebbers |
| 5,977,433 A | 11/1999 | Williams |
| 6,008,437 A | 12/1999 | Krebbers |
| 6,037,523 A | 3/2000 | Albertsen et al. |
| 6,288,302 B1 | 9/2001 | Yu et al. |
| 6,743,968 B2 | 6/2004 | Dellaporta |
| 6,753,139 B1 | 6/2004 | Baulcombe |
| 7,071,375 B2 | 7/2006 | Brown et al. |
| 7,098,388 B2 | 8/2006 | Albertsen |
| 7,151,205 B2 | 12/2006 | Albertsen et al. |
| 2003/0175965 A1 | 9/2003 | Lowe et al. |
| 2005/0120416 A1 | 6/2005 | Perez |
| 2005/0246796 A1 | 11/2005 | Cigan et al. |
| 2006/0288440 A1 | 12/2006 | Albertsen |
| 2008/0244765 A1 | 10/2008 | Zhao et al. |
| 2009/0038026 A1 | 2/2009 | Albertsen |
| 2009/0038027 A1 | 2/2009 | Albertsen |

FOREIGN PATENT DOCUMENTS

| | | |
|---|---|---|
| WO | WO9201366 A1 | 2/1992 |
| WO | WO9325695 | 12/1993 |
| WO | WO9529247 A1 | 11/1995 |
| WO | WO9613588 A1 | 5/1996 |
| WO | WO9617945 A1 | 6/1996 |
| WO | WO9640925 A2 | 12/1996 |
| WO | WO9854340 A1 | 12/1998 |
| WO | WO9859061 A1 | 12/1998 |
| WO | WO0106845 A2 | 2/2001 |
| WO | WO0226789 A2 | 4/2002 |
| WO | WO02052924 A2 | 7/2002 |
| WO | WO03057848 A2 | 7/2003 |
| WO | WO03076632 | 9/2003 |
| WO | WO2007002267 A1 | 1/2007 |

OTHER PUBLICATIONS

Kovar et al. The Plant Cell 12: 583-598 (Apr. 2000).*
Williams (1995) Trends Biotechnol. 12, 344-349.
Perez-Prat (2002) "Hybrid seed production and the challenge of propagating male-sterile plants" Trends Plant Sci. 7, No. 5 1999-203.
Shupin et al.(2005) ROXY1, a member of the plant glutaredoxin family, is required for petal development in *Arabidopsis thaliana*, Development, 132, 1555-1565.
West and Albertsen (1985) "Three new male sterile genes" Maize Newsletter 59:87.
Neuffer et al. (1997) Mutants of maize, MS22, Cold Spring Harbor Laboratory Press, Cold Spring Harbor NY p. 265, & p. 311.
Johnston et al. (1986) A wildtype rice Msca1 gene from plant variety M202, Crop Science Vo.26 Jan.-Feb. , p. 198.
GenBank Acession No. XP_476652 (Nov. 2004) "Glutarexon-like protein (oryza sativa) (japonica-cultivar-group)".
Chaubal et al. (2003) "The transformation of anthers in the mscal mutant of maize" Planta 216:778-788.
Trimnell et al. (2001) "New male-sterile mutant allele of Msca1" MNL 75(63):31.
Merriam-Webster Dictionary (2004) www.m-w.com/cgi-bin/dictionary?book=Dictionary&va=mediate&x=22&y=21.
Guo et al. (2004) Proc. Natl. Acad Sci. USA 101:9205-9210.
Feldmann (1991) Plant J. 1:71-82.
Cone et al. (1988) Basic Life Sci. 47:149-159.
Donald (1990) EMBO J. 9:1717-1726.
Hao (1998) J. Biol. Chem 273:26857-26861.
Rebers (1999) Insect Biochem. Mol. 29:293-302.
Vrati (1996) Virology 220:186-199.
Millar (2001) Molecular Psychiatry 6:173-176.
Aranda-Agustin Nucleic Acids Res 26:4588-4596, (1998).
Tang (1999) Plant Cell 11:177-189.
Arndt (1997) Genome 40:785-797.
Colliver (1997) Plant Mol. Biol. 35:509-522.
Klann (1996) Plant Physiol. 112:1321-1330.
Lazar (1998) Mol. Cell Biol. 8:1247-1252.

(Continued)

Primary Examiner — David T Fox
(74) Attorney, Agent, or Firm — Patricia A. Sweeney

(57) ABSTRACT

Nucleotide sequences of a Mscal gene, critical to male fertility in plants are described, with DNA molecule and amino acid sequences set forth. Promoter sequences and their essential regions are also identified. The nucleotide sequences are useful in impacting male fertility in plants.

21 Claims, 19 Drawing Sheets

OTHER PUBLICATIONS

Hill (1998) Biochem Biophys. Res. Comm 244:573-577.
Lisch (2002) Trends Plant Sci. 7:498-504.
(2005) XP002478552 "Rice abiotic stress responsive polynucleotide SEQ ID No. 1602" Accession ACL27646.
(2001) XP002478553 "Oryza sativa Japonica Group genomic DNA, chromosome 7, BAC clone: OJ1048_C10" Accession AP003704.
Rouhier et al.(2006) "Genome-wide analysis of plant glutaredoxin system" Journal of Experimental Botany, vol. 57, No. 8: 1685-1696.
(2003) XP002478554 "Glutaredoxin-C9" Accession No. Q7XIZ1.
XP002478555 (2006) "Zea mays chromosome 7 clone ZMMBBb-226D18; ZMMBBb0226D18 sequencing in progress 13 unordered pieces" Accession No. AC195322.
Bortiri et al. (2006) "Advances in maize genomics: the emergence of positional cloning" Current Opinion in Plant Biology vol. 9, No. 2: 164-167.
Hessel et al. (2007) "Dual testcross QTL analysis: a solution to the current rate-limiting steps of positionally cloning QTL in maize" 49th Annual Maize Genetics Conference, [Online] 2007, p. 130, XP002478550.
Williams et al. (2006) "Map-based cloning of the nsf1 (nicosulfuron susceptible 1) gene of maize" 48th Annual maize Genetics Conference [Online] XP002478551.
Unger et al. (2002) "A chimeric ecdysone receptor facilitates methoxyfenozide-dependent restoration of male fertility in ms45 maize" Transgenic Research 11:455-465.
Unger et al. "Selection and orientation of adjacent genes influences DAM-mediated male sterlity in transformed maize" Transgenic Research (2001) 10:409-422.
Wesley et al. (2001) "Construct tesing for efficient, effective and high-throughput gene silencing in plants" The Plant Journal, 27(6): 581-590.
Iyer et al. (2000) "Transgene silencing in monocots" Plant Molecular Biology, 43:323-346.
Kapoor (2002) "Silencing of tapetum-specific zinc finger gene TAZ1 causes premature denegration of tapetum and pollen abortion in petunia" The Plant Cell. vol. 14, 2353-2367.
Smith et al. (2000) "Total silencing by intron-spliced hairpin RNAs" nature vol. 407: 319-320.
Waterhouse et al. (2003) "Exploring plant genomes by RNA-induced gene silencing" Nature Reviews, vol. 4: 29-38.
Mette et al. (2000) "Transcriptional silencing and promoter methylation triggered by double-stranded RNA" The EMBO Journal, vol. 19: 5194-5201.
Kooter et al. (1999) "Listening to the silent genes: transgene silencing, gene regulation and pathogen control" Trends in Plant Science, vol. 4 No. 9, pp. 340-347.
Cigan et al. (2001) "Phenotypic complementation of ms45 maize requires tapetal expression of MS45" Sex Plant Reprod. 14:135-142.
Sijen et al. (2001) "Transcritpional and posttranscriptional gene silencing are mechanistically related" Current Biology, 11:436-440.
Burgess et al. (2002) "A novel two-component system for cell lethality and its use in engineering nuclear male sterility in plants" The Plant Journal, 31(1): 113-125.
Luo et al. (2000) "FLP-mediated recombination for use in hybrid plant production" The Plant Journal, 23(3): 423-430.
Singh et al., Genetics 143(1):505-516 (May 1996).
Araya et al., pp. 93-91 in Plant Mitochondria, Brennicke A. et al. eds. VCH:Weinheim Germany (1993).
Chen et al., Sexual Plant Reproduction 13(2):85-94 (2000).

* cited by examiner

Figure 2: *Mscal* Genomic aattcgcgggacgtggcgttgtcggctccgtgtcggcggccgaaccaccacgaatcactgacgtatctcgtctcctctctcctctagactcccacgatacggccaac
gaagtgtatgtacatatataccatggtcatatggcaacaaacgccaacgccagcagagcactgcccggcggccttttccatctctctctctctctgatggggtgt
gcatgcctgactgactgatagatagatagatggtcaggtccgtctgatcctcatcggcctagctcaccccacgcgaaaaaagccactgctggctggcgcccagttgc
gcttgcaacagtcactttaacgagctccgtccttgcgtttgccctcctcgctctgcccctgccgccgctgccgctgcgtggtggtgctggtgcatgaggcaggcaggc
gtactagtgcatgcaattgcaatgcaaccgtaggagtgcgttgcgtaccctggtctgtccctgcggcctggcctgcccttgttcgttgcggatgcgggggggtgccgg
gtgggtactgtactgtactactgggtagagagatactactagatagagagagagagaggtcggtcaccccgggcgcgggacacagcctctgcgaaaaagcgatc
catgtcgcgcctagctttgacccggaacggatcccccaaccaggaaccagcagagcaggagggccaggccaccacctctcgccattccattcccggtcctagcta
gtcctgttctgttcctgtagcagtagcagtagctacggtactacgagtcctcctcgacgtcccaggcactactccactccacgcagcagcaggcagcgagcatctctc
gaccagatgcatacaagctacaccctcctcggctccgatcctacccatgccggcccaggcggcctataaaagcgcacccccggcccgtcttcctcccactgcatgc
ccattgccctcccccggccttcgccgtgccaacgacacacctcatcaccggccggaacattccacgaccgaagaaaccagtccctagctagtccacgcacgacc
aacaaggcaggcgagcgacgacagtccaagcctccaagaagaagaagaagaagaagaagaagaagatgctgcggatggaggtgcagcagcaggagtcggg
agtgagcggcggcgtggtggcggacgcggcggcggcgggatccgtggcggaagccgcgacgacgacgatggtggccgcggcgccgcactcggcgtcggc
gctggcggtgtacgagcgggtggcgcgcatggcggcggaacgcggtggtggtgttcagcgccagcggctgctgcatgtgccacgtcgtcaagcgcctgctg
ctgggcctcggcgtcggccccaccgtgtacgagctcgaccagatggccggcggcggcggggggcagggagatccaggcggcgctggcgcagctgctgccgcc
gggccagccgccccctgcccgtcgtcttcgttggcggccgcctcctcggcggcgtcgagaaggtcatggcgtgccacatcaacggcaccctcgtcccgctcctcaa
gcaggccggcgcgctctggctctgatcgcgccgtcgtcgtcgtcgtcgtcgtcgatcggccactgcaacagacaacagtgtgcgtgtgtgtgtggctgtgtgcgcat
ctccgtgcatgcgatcgatcgctgccccttagttagttactcactacttactaccttgcgttttaatgtaacctctactaagctagctagctcttgtcctgttccgtgcatgag
agaggtcgagtaatgccgcaatcgcctgctgcagttaatgcagcagcgcacgacgacgtcgccgatgatggttgatggtgcatcgattattgcactccatggatatc
atccatcttaaccggacgtggacgtacggtgccccggccggtgcagcaggggccagtcagcagcccttgtaaaagcgtacccgtacgtacgtcgtcgagacatca
acgacgtacggggacgcaacgcaaccagccaaaacgggatcgttcgaactagagcaagacgtacggcttttcgatgagctggccggtgtgttagactgttagacata
aaaaaaatacataatataataaacatagaagctatccatggtttctagctttatgttgggactgcactaatgaccatagcaatgcgctcatcaagttatcaaattttactccc
tccatggtgcctcacaacagtacgtacgtagtcgtttcgtgatgaaacacaatacacaaaattttactccctccgtttcattttacaagtcgtttccaacagccaatgcata
aatagcagcgacaactaaaatgaaacggagtaatacgtaaaaagtcttttataggaaacaaaacacgagcgtcaaccgtcaatcttcattatacgatgagagtttgtag
aacatagaatacaattagtcgaatcccttctcgtgcgatatgtatatatacatacgacggacgaactaaaccagtaccataatcaaaatcaatgtattcagtaagcccat
ctctaaatttcctaaagtgcaaacaaagattagaggtacgtcgcaaatatatataaaaaaatccactacacacgatcctctaattactgctccttattatcatggttaggcc
acgtacaacgggtgtcttaagctgtgtcttgttgaaggagggtaaatgtaaaaaaactcaagcacacatatcttaacgaagatattgtgtttggctttatgctcgatacatat
gggaacagctgattggtaaaattaatttattgaatgttccgattgatgcaatgaatatagcaagacatatgttttaattagacacgtccactgtattatattgtgttttagctat
atcttatacttggagtatcgtgcagcggtgtcagggttgtacatacatgcccttagccatctaccgacggcattcaatgcgtgtgagataaatcaggataagagcgaac
catgagatgcataagagaaccgatttccctgaaatatgaaactgtagg Figure 3: *Msca1* protein MLRMEVQQQESGVSGGVVADAAAAGSVAEAATTTMVAAAPHSASALAVYERVARMAGGNAVVV
FSASGCCMCHVVKRLLLGLGVGPTVYELDQMAGGGGGREIQAALAQLLPPGQPPLPVVFV
GGRLLGGVEKVMACHINGTLVPLLKQAGALWL Figure 4: *msca1* reference allele

```
>ms22ref
GGACGCGAGTGTGACCTTTTGCATGGCAAACTCGATCGCAGTCGCAGTCTCGCTGCATGCGTGCGTACGTACGTACGTGCAACGCAATGGATCGG
AATGCCCGATCTATCGACCGACGTGGAGGAGGACGGTCGATCTGCATGCATGCGAACAGTGCAAGTGGACATATATATATGCACCGTTGGACGT
TGGTACGGGCCGGGGGGCGGGGGGCCGGTGTGGCCGCGTGCACATGCAGCAGCCTTTATGATGGGGGTACGTGCACGAACTAAACTAACGGTGCCACACAA
GAAAGTGGAGAGAACTTCCCTCGATCAGGTGCTAGTTGCTTCTTGAGGCCCAGATGTCGGAGGCCCGGCCTGCCGTACGTACGTAACGTGACACG
ATGCGCTGATGTGCATCATGCATGTTATATGTATATATCATATAATACTCCAGCATGTCGGCGACCACACCTTGCTTCAGGACTTGTTTCGTCCGG
TCCCTCAGCTCGCTCCGACAACGACGACGACACTCTCTCCCGGCCCTTGTCGCGCTCTCGTCCAACAACAGCAGTCGTAGTAGCAAGAAAGCCA
AATGTGTGTTAATCATAAATTGTTGGTCAAAAGGCTACCTACCGTGTCCTAACAAGACCAAAAAGACGTGTGATAATGTTAACTAGAAGAAGCA
GTAGCCTTTTCCACTTTTAACTGGTTCACTGCACACTGAAGAAACATGTATATATACCCCCTCTCTCTATCTCTCTCCCTTGAAATCAACTTTTCTTT
TAACGCTCTCTTCGTTTCCATGGCATGCATCGTTCGCCTCCCCCCCCCCCCCCTCATTGCTCCATCCGGCCTTGCGTTGTATACCACCTCCGACGAC
CCTAAATAACAGATAAAGTTTTAGTTTCCATGAGTGAAGCCTCTATGCTTTATTCTTAAAATCCGACGACCAATTCTATTATATAAAAAGGAGTAT
AATTGGTGTACAAATGCATGGCACTGGAAAAAAAAGTCAAGCGTTAAAATACATTCCATGTCATTATCAAACTATATATGTTAACTAGGTGAGTAC
CCGTGCGTTGCAACGAGATCATATAATAACATAATAAGTTATATACAAAATGTGTCTTATATTGTTATAAAAAATATTTCATAATCCATTTATAA
TCCTAGCCATACATAAATTTTGTTATTTTAATTTAGCTGTTTCATTATTTCATTGCAACCATCAGTATCATGCAGACTTCGATATATGCCACGATTT
GCATGGTCTCATCATTGAAGAGCACGTGTCACACCTACCGGTAGAAGTTCCCTCGTACATTGTCAGTCATCAGGTACGCACCACCATACACGCTT
GCTTAAACAAAAAAAGCAAGTGCATGTGTTTGCGAAGATAATTAAAGGCAGGCCGACACAAAAGCTACCCCGACGATGGCGAGTGGTCATTGTT
GTCGGTCCTCCTCTGCGTCACCTCTGGTGCCAAGATGACGCCATAGTCCTTGATATAGTAGTCGTCGAACGCGCATGACATGACGAGTACCGATG
ACTCTTGGCTGGGCTGTCAAACGAAGTGCACCCCGGGCTCATCAGCGAGGTAGTACACCTAGCCGTTGCACCACCGGATGTGCCGCTCCTCTACA
TAAATCTTGTTCGAGGACACTCACACAACGTCAGCAACGACCGTCGTCCCAGCGCATAAGAATTCATGGCCGGTCAGTAGTGACTTACGTGGGAG
GTTGAGCTTCAGGTGGATGATGAGCTGGATGGTGTGACGGCGCCGTTGTCGGATGCGGTGCCCAGAACAACCCGAGAGTCGCCGGTGTTGGCGA
CGACCATGAGGTCCCCCTATTTGAAGATGGACAATGCGGAGCAGCCGCTCTGAACCGCGTCCAAGCAATTGCATGCAAGGCTCTTTTTTAAATAC
TACTCCCTCCATCCAAAATATATAATTCAGGAATCTCGTTGATAATTATCTACTACTACACATTATGCAAAGGTAGCAGGTAGACTTTGAGAGAG
ATGTATTATATATTTTTACTATAACAAATATTAACATAAACACACATGTGGTGTAGTAGTAGCTACGAGCACATTTGCTTGAGAGGTCGCAGGTT
CGAATCTCATTGGAGCCACATTTGTGAGAATGAGATTTGCGGGGAGGGGGGCACTAGCAACATGAATGAGAATGGGAATGGGCTTTACGGGGAG
GGGAGAATGGGAAAGACATTGCGGGAATGGAAATGACAGAACACGGAATGGCAGCCTACCCTTTACCGTCTTAATAAGTAGTAGAGATCAGGC
AACACAGCAGAGTAGTATTGCACCGTTACCAGTTCAGCTGAGGCTGAGACTGAGCGCGCAAAGGTACAGTTTGTGTCCGGCAAGGGAAGACGAC
GAGTCGACGACCGACCGACCGACAGACCGAGGACCGGACCGCCGGACGGGAAAGTCAATGGGCTGGGCAGTTTCATGCTAGTGGGCTGAACGA
TCTGTTATTTGATGTGGCCCACCACTGTTGAGGTCCACTAGTCCTTTACTCCTTTGGAGCGACGAGTCGGCCCATATCCTAGTTCCGCAGAGAGAC
TGACGAAGAGACCAGTGGAAGTTGGAACCCTGAAACCCGCTGCCTACAACTGCAGCTCCGTTTTATTTTGCCTTTTCACACGACGGCAATCTGGT
TTTTATTTATAGCGTAACGGAAATACTATACTACAGCAGAGTTTTTTTTTATTTGGATAAAGGCGTTGGCGTGTTGCAAATAAAGACGCGTGTCGG
TGTCACAACGAAGAAGAAGAAAAAGCAGGTTGATACCTACCACTATACTGTACCATATAGAGCGCACATGCAGCTGCGATCTCCCTTCTTCCCCC
ATCCATC
```

Figure 5: msca1-mg12 alignment

```
                M L R M E V Q Q Q E S G V S G G V V
Fert:   381 agaagaagatgctgcggatggaggtgcagcagcaggagtcgggagtgagcggcggcgtgg 440
            ||| | | || | || ||  |||||||||||||||||||||||||||||||||
Mg12:   358 agatgctgcggatggaggtgcagcagcagcaggagtcgggagtgagcggcggcgtgg 417
                M L R M E V Q Q Q Q E S G V S G G V V A D A A A A G S V A E A A           T T T M V
Fert:   441 tggcggacgcggcggcggcgggatccgtggcggaagccg------cgacgacgacgatgg 494
            ||||||||    |||||||||||||| |||| ||||         ||||||||||||||
Mg12:   418 tggcggac---gcggcggcgggatccgtagcggatgccgccacgacgacgacgacgatgg 474
                A D - A A A G S V A D A A T T T T T M V A A A F H S A S A L A V Y E R V A R M A
Fert:   495 tggccgcggcgccgcactcggcgtcggcgctggcggtgtacgagcgggtggcgcgcatgg 554
            ||||||||||||||||||||||||||||||||||||||||||||||||||||||||||||
Mg12:   475 tggccgcggcgccgcactcggcgtcggcgctggcggtgtacgagcgggtggcgcgcatgg 534
                A A A P H S A S A L A V Y E R V A R M A G G N A V V V F S A S G C C M C H V V K
Fert:   555 cgggcgggaacgcggtggtggtgttcagcgccagcggctgctgcatgtgccacgtcgtca 614
            ||||||||||||||||||||||||||||||||||||||||||||||||||||||||||||
Mg12:   535 cgggcgggaacgcggtggtggtgttcagcgccagcggctgctgcatgtgccacgtcgtca 594
                G G N A V V V F S A S G C C M C H V V K R L L L G L G V G P T V Y E L D Q M A A
Fert:   615 agccgctgctgctgggcctcggcgtcggccccaccgtgtacgagctcgaccagatggccg 674
            ||||||||||||||||||||||||||||||||||||||||||||||||||||||||||||
Mg12:   595 agccgctgctgctgggcctcggcgtcggccccaccgtgtacgagctcgaccagatggccg 654
                R L L L G L G V G P T V Y E L D Q M A A S G G G R E I Q A A L A Q L L P P G Q P
Fert:   675 ccagcggcgggggcagggagatccaggccggctggcgcagctgctgccgccgggccagc 734
            |||||||||||||||||||||||||||||||| |||||||||||||||||||||||||||
Mg12:   655 ccagcggcgggggcagggagatccaggccggctggcgcagctgctgccgccgggccagc 714
                S G G G R E I Q A A L A Q L L P P G Q P P L P V V
Fert:   735 cgccctgcccgTCGT 750
            |||||||||||
Mg12:   715 cgccctgcccgACATCAACGACATACGAACA 746
                P L P V T N D I R T F V G G R L G G V E F V M A C H
Fert:   751 CTTCGTTGGCGGCCGCCTCCTCGGCGGCCGTCGAGAAGGTCATGGCGTGCC I N G T L V P L L K G A G K L W
Fert:   801 ACATCAACGGCACCCTCGTCCCGCTCCTCAAGCAGGCCGGCGCGCTCTGG L *
Fert:   851 CTCTGATCGCGCCGTCGTCGTCGTCGATCGGCCACTGCAACAGACAACAG Fert:   901 TGTGCGTGTGTGTGTGGCTGTGTGCGCATCTCCGTGCATGCGATCGATCG Fert:   951 CTGCCCCTTAGTTAGTTACTCACTACTTACTATTACTACGCCTTGCGTTT Fert:  1001 TAATGTAACCTCTACTAAGCTAGCTAGCTCTTGTTCTGTTCCATGCATGC Fert:  1051 ATGAGAGAGGTCGAGTAATGCTGCAATCGCCTGCTGCAGTTAATGCAGCA Fert:  1101 GCGCGCGCACGACGTCGCCGATGATGGTGCATCGATTATTGCACTCCATG Fert:  1151 GATCATCCATCTTAACCGGACGTGGACGTACGGTGCCCCGGCCGGTGCAG Fert:  1201 GCAGAGGAGGGCGGCGGCCGGCGCTAGCTGCCTCC Fert:  1236 ggctgaggtcacagtctcacagagcagcaggccgggggccagtcagcagccttgtaaaag 1295
            ||||||||||||||||||||||||||||||||||||||||||||||||||||||||||||
Mg12:   747 ggctgaggtcacagtctcacagagcagcaggccgggggccagtcagcagccttgtaaaag 806

Fert:  1296 caaacgtacgtacgtcgtcgagac 1319
            |  ||||||||||||||||||||
Mg12:   807 cgtacgtacgtacgtcgtcgagac 830
```

Figure 6: GRX alignment from fertile and sterile alleles

```
                    REDOX
Mo17:       1  MLRMEVQQQ--ESGVSGGVVADAAAAGSVAEAATTT--MVAAAPHSASALAVYERVARMA  56
Mg12-Fert:  1  MLRMEVQQQ  ESGVSGGVVADAAAAGSVAEAATTT  MVAAAPHSASALAVYERVARMA  56
MG12-Ster:  1  MLRMEVQQQQQESGVSGGVVADAAA-GSVADAATTTTTMVAAAPHSASALAVYERVARMA  59

Mo17:      57  GGNAVVVFSASGCCMCKVVKRLLLGLGVGPTVYEIDQMAGGGGREIQAALAQLLPPGQP  116
Mg12-Fert: 57  GGNAVVVFSASGCCMCKVVKRLLLGLGVGPTVYEIDQMAASGGGREIQAALAQLLPPGQP  116
MG12-Ster: 60  GGNAVVVFSASGCCMCKVVKRLLLGLGVGPTVYEIDQMAASGGGREIQAALAQLLPPGQP  119

Mo17:     117  PLPVVFVGGRLLGGVEKVMACHINGTLVPLLKQAGALWL  155
Mg12-Fert:117  PLPVVFVGGRLLGGVEKVMACHINGTLVPLLKQAGALWL  155
MG12-Ster:120  PLPDINDIRTG  130
                          GSH-Binding
```

Figure 7: 890 bp Insertion in ms22-6036

Figure 7A

```
6036FERTILE versus 6036 sterile
        (1351 letters)

Fert:   12  ggccaggccaccacctctc--gccattccattcccggtcctagctagtcctgttctgttc  69
            ||||||||||||||||||  ||||||||||||||||||||||||||||||||||||||
6036s:  28  ggccaggccaccacctctctcgccattccattcccggtcctagctagtcctgttctgttc  87

Fert:   70  ctgtagcag---------tagctacggtactacgagtcctcctcgacgtcccaggcacta  120
            |||||||||         |||||||||||||||||||||||||| |||||||||||||
6036s:  88  ctgtagcagcagtagcagtagctacggtactacgagtcctcctcgrcgtcccaggcacta  147

Fert:  121  ctccactccacgcagcagcaggcagcgagcatctctcgaccagatgcatacaagctacac  180
            ||||||  |   |||||||  || ||||||||||||||||||||||||||||||||||
6036s: 148  ctccacgca--gcagcaggcagcggcgagcatctctcgaccagatgcatacaagctacac  205

Fert:  181  cctcctcggctccgatcctacccatgccggcccaggcggcctataaaagcgcaccccgg  240
            ||||||||||||||||||||||||||||||||||||||| |||||||||||||||||||
6036s: 206  cctcctcggctccgatcctacccatgccggcccaggcgtcctataaaagcgcaccccgg  265

Fert:  241  cccgtcttcctcccactgcatgcc--cattgccccccggccttcgccgtgccaacgaca  298
            ||||||||||||||||||||||    |  |||  || |  ||||||||||||||||||
6036s: 266  cccgtcttcctcccactgcaatactgcatgcccatcaccccttcgccgtgccaacgaca  325
```

Figure 7B

```
Fert:   299 cacctcatcaccggccggaacattccacgaccgaagaaaccagtccctagctagtccacg 358
            ||||||||||||||||||||||||||||||||||||||||||||||||||||||||||||
6036s:  326 cacctcatcaccggccggaacattccacgaccgaagaaaccagtccctagctagtccacg 385

Fert:   359 cacgaccaacaaggcaggcgagcgacgacagtccaaagcctccaagaagaagaagaacga 418
            ||||||||||||||||||||||||||||||||||||||||||||||||||||||||||||
6036s:  386 cacgaccaacaaggcaggcgagcgacgacagtccaaagcctccaagaagaagaagaacga 445

M  L  R  M  E  V  Q  Q  Q  Q  Q  E  S  G  V  S  G  G  V  V
Fert:   419 agatgctgcggatggaggtgcagcagcagcagcaggagtcgggagtgagcggcggcgtgg 478
            ||||||||||||||||||||||||||||||||||||||||||||||||||||||||||||
6036s:  446 agatgctgcggatggaggtgcagcagcagcagcaggagtcgggagtgagcggcggcgtgg 505
                                   M  L  R  M  E  V  Q  Q  Q  Q  Q  E  S  G  V  S  G  G  V  V A  D  A  A  A  A  S     G  A  D  A  A  P  T  T  T  T  M  V  A
Fert:   479 tggcggacgcggcggcggcatccggggcggatgccgcgccgacgacgacgacgatggtgg 538
            ||||||||||||||||||||       |||||    |||||||||||||||||||||||||
6036s:  506 tggcggacgcggcggcgggatccgtagcggatgccgccacgacgacgacgacgatggtgg 565
             A  D  A  A  A  G  S     V  A  D  A  A  T  T  T  T  T  M  V  A A  A  P  H  S  A  S  A  L  A  V  Y  E  R  V  A  R  M  A  G
Fert:   539 ccgcggcgccgcactcggcgtcggcgctggcggtgtacgagcgggtggcgcgcatggcgg 598
            ||||||||||||||||||||||||||||||||||||||||||||||||||||||||||||
6036s:  566 ccgcggcgccgcactcggcgtcggcgctggcggtgtacgagcgggtggcgcgcatggcgg 625
             A  A  P  H  S  A  S  A  L  A  V  Y  E  R  V  A  R  M  A  G
```

Figure 7C

```
                G  N  A  V  V  V  F  S  A  S  G  C  C  M  C  H  V  V  K  R
Fert:   599 gcgggaacgcggtggtggtgttcagcgccagcggctgctgcatgtgccacgtcgtcaagc 658
            ||||||||||||||||||||||||||||||||||||||||||||||||||||||||||||
6036s:  626 gcgggaacgcggtggtggtgttcagcgccagcggctgctgcatgtgccacgtcgtcaagc 685
                G  N  A  V  V  V  F  S  A  S  G  C  C  M  C  H  V  V  K  R L  L  L  G  L  G  V  G  P  T  V  Y  E  H  D  Q  M  A  A  G
Fert:   659 gcctgctgctgggcctcggcgtcggccccaccgtgtacgagcacgaccagatggccgccg 718
            |||||||||||||||||||||||||||||||||||||||||| |||||||||||||||
6036s:  686 gcctgctgctgggcctcggcgtcggccccaccgtgtacgagctcgaccagatggccgc-- 743
                L  L  L  G  L  G  V  G  P  T  V  Y  E  L  D  Q  M  A  A G  G  G  G  R  E  I  Q  A  A  L  A  Q  L  L  P  P  G  Q  P
Fert:   719 gcggcggcggggcagggagatccaggcggcgctggcgcagctgctgccgccgggccagc 778
            ||||||||||||||||||||||||||||||||||||||||||||||||||||||||||||
6036s:  744 -cggcggcggggcagggagatccaggcggcgctggcgcagctgctgccgccgggccagc 802
                G  G  G  G  R  E  I  Q  A  A  L  A  Q  L  L  P  P  G  Q  P MG12 deletion site
                          ^
                P  L  P  V  V  F  V  G  G  R  L  L  G  G  V  E     K
Fert:   779 cgcccctgcccgtcgtcttcgtgggcggacgcctcctcggcggcgtcgagaa 830
            |||||||||||||||||||||||||||||  || |||||||||||||||||
6036s:  803 cgcccctgcccgtcgtcttcgtgggcggccgactcctcggcggcgtcgagaa 854
                P  L  P  V  V  F  V  G  G  R  L  L  G  G  V  E     N
```

Figure 7D

```
Fert:   ---------------------------------------------------...

6036s: 855 TAGTCCTGTAAGTTTGGGCCGTGCTTGCTGGGCCAGCACGAGCACGGCACGAAATA
           S  P  V  S  L  G  R  A  C  W  A  S  T  S  T  A  R  N  R
           TIR

6036s:     GATAGCACGCAGCCCGGCCCAGCACGAAACAGAAAAAATCGGGCCAGCACGACACGGTAG
                                                *
6036s:     ACGGGCTGGGCCGTGCTCTAGCTGGTGGCCCGACGSCCCAAATAGCCCGGCACGCCGTCG
6036s:     TGGGCCGTGCTCGGGCCAGCCCGGCACGATTTAGGGTTAGGGTTCCTATGACGGCGGCTC
6036s:     TCCTCGTTTTCTCCGCTCGCTCTCGTCCGCTCGTTCTCTTCTGCGACCACAGCGCGCCGT
6036s:     CCACCGCTCGCTGGCCTCTCGCGCCTCAGCACCAAGACTTCGGCGGCGGGCCCTGCTCCT
6036s:     CCCAGCGCGCCACCTCGCGCTCCTCGTGCACCCGCCGAAGTCCCAGCAGGCCAGCACACC
6036s:     ACCTCACGCTCCTCCCAGCGAGCCGCCGAAGTCCCAGCGCGCCACCTCGCGCTCCTTCCA
6036s:     GCAAGCCGCCGCGCAATCGAGGACAAGCTGCAGGCCTACAGCCGCCGGAGCCCAGGCAAT
6036s:     CGAGGACCAGCTGCAGCCGTCGGAGCCTAGTTCCGGCCATGATCCCGCCCTCGCGCCGTA
6036s:     GCTGCGCCGCCGCCGCCGCCGGCCGACTTGACGGCCACGAGCTCGCCCTCGCCCGCCGCG
6036s:     ACACGACGGCGCCTGAGAGGAGCACCTGAAGCACTCTTACGGGCCGGGTCTGGGCCAGCA
6036s:     CGGCACGATGCAAGCCCACCGTGCTTTAGGGCCGTGCTGGGCCTATATTTTAAGACGTGA
6036s:     GCACGATATAGCCCGGCTCGAATGCATTTCGTGCTAGCCCGGCCCGAAGTATTTCAGCCC

Fert:   ...----------------------------------------------------

6036s:     GAAGCACGACGGGCCCGTGCCGGGTCAGCACGGCCCGGCCCAATTTGCAGGACTA      1745
                                                        TIR

8bp host site duplication
              V  E  K  V  M  A  C  H  I  N  G  T  L  V  P  L  L  K  Q  A
```

Figure 7E

```
Fert:   823  gtcgagaaggtcatggcgtgccacatcaacggcaccctcgtcccgctcctcaagcaggcc  882
             |||||||||| |||||||||||||||||||||||||||||||||||||||||||||||
6036s: 1746  gtcgagaaggttatggcgtgccacatcaacggcaccctcgtcccgctcctcaagcaggcc 1805

G  A  L  W  L  *
Fert:   883  ggcgcgctctggctctgatcgcgccgccgccgtcgtcgtcgatcggccactgcaaca  942
             |||||||||||||||||||||||||||||| |||||||||||||||||||||||||||||
6036s: 1806  ggcgcgctctggctctgatcgcgccgtcgccgtcgtcgtcgatcggccactgcaaca 1865

Fert:   943  g  943
             |
6036s: 1866  g 1866

Fert:   943  gtgtgtgtgtgtgggtgtccatctccgtgcatgcgatcgatcgctgccccttagacctta 1002
             |||||||||  || |||  ||||||| |||||||||||||||||||||||||||   |||
6036s: 1883  gtgtgtgtggctgtgtgcgcatctctgtgcatgcgatcgatcgctgccccttag---tta 1939

Fert:  1003  gttagttactcacttactac--cttagc-ttgcgttttaatgtaacctctactaagctag 1059
             |||| | ||| ||||||||    ||  || |||||||||||||||||||||||||||||
6036s: 1940  gttactcact-acttactattactacgccttgcgttttaatgtaacctctactaagctag 1998
```

Figure 7F

```
Fert:   1060 ctagctcttgttctgttccgtgcccatgcatgagagagatcgagtaatgctgcaatcgcc 1119
             |||||||||||||||||||| |||   ||||||||||||| |||||||||||||||||||
6036s:  1999 ctagctcttgttctgttccatgc--atgcatgagagaggtcgagtaatgctgcaatcgcc 2056

Fert:   1120 tgctgcaattaatgcagca----gcgcacgacgtcgccgatatatgatggtgcatcgatt 1175
             ||||||| ||||||||||||    ||||||||||||||||    ||||||||||||||||
6036s:  2057 tgctgcagttaatgcagcagcgcgcgcacgacgtcgccg----atgatggtgcatcgatt 2112

Fert:   1176 attgcactccgatccatggatatcatcgatcttaaccggacgtggacgtacggtgccccg 1235
             |||||||        |||||||  ||||||  ||||||||||||||||||||||||||||
6036s:  2113 attgcac-----tccatgg--atcatccatcttaaccggacgtggacgtacggtgccccg 2165

Fert:   1236 gccggtgcaggcagatcgaggagggcggcggccggc----gatgccccggctgagg--- 1288
             |||||||||||||    |||||||||||||||||||    |  ||| |||||||||
6036s:  2166 gccggtgcaggca----gaggagggcggcggccggcgctagctgcctccggctgaggtca 2221

Fert:   1289 -----tcacagagcagca-gccggggccagtcagca-gccttgtaaaagcgtacgtacg 1341
                  |||||||||||||| |||||||||||||||| |||||||||||||||||||||||
6036s:  2222 cagtctcacagagcagcaggccggggccagtcagcangccttgtaaaagcgtacgtacg 2281

Fert:   1342 tacgt 1346
             |||||
6036s:  2282 tacgt 2286
```

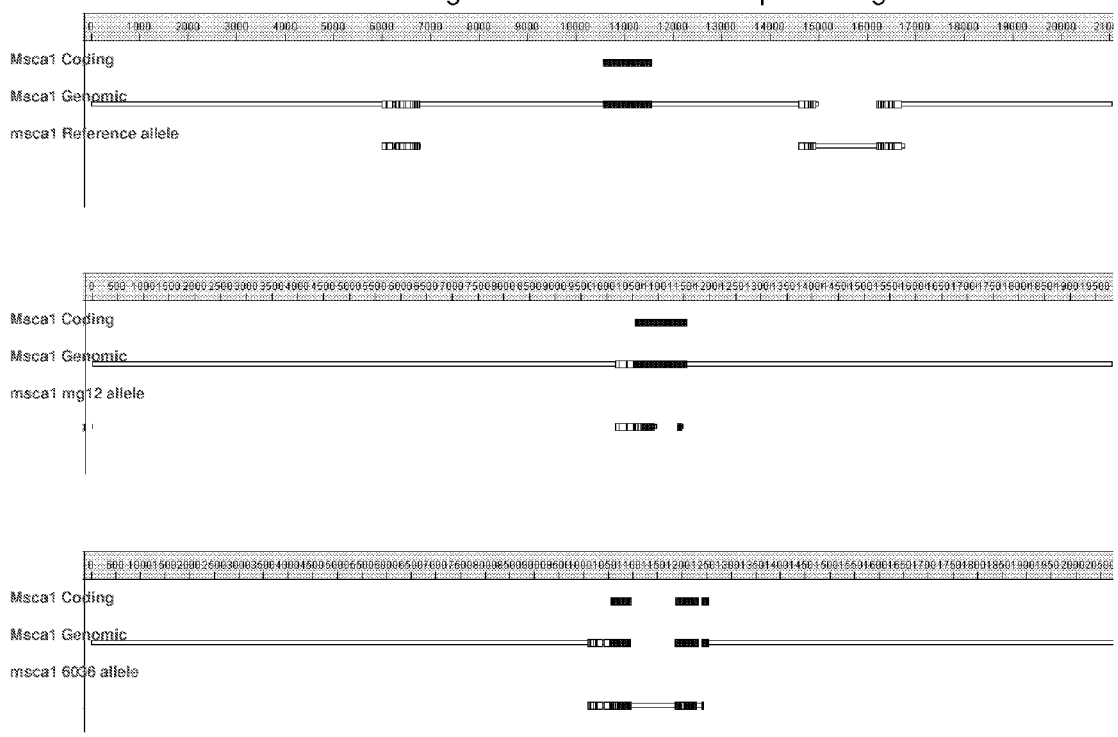

Figure 9: *Msca1* Promoter region aattcgcgggacgtggcgttgtcggctccgtgtcggcggccgaaccaccacgaatcactgacgtatctcgtctcctctctcctctagactcccacgatacg
gccaacgaagtgtatgtacatatatacccatggtcatatggcaacaaacgccaacgccagcagagcactgcccggcggccttttcccatctctctctctct
ctctgatggggtgtgcatgcctgactgactgatagatagatagatggtcaggtccgtctgatcctcatcggcctagctcaccccacgcgaaaaaagccact
gctggctggcgcccagttgcgcttgcaacagtcactttaacgagctccgtccttgcgtttgccctcctcgctctgccccctgccgccgctgccgctgcgtggt
ggtgctggtgcatgaggcaggcaggcgtactagtgcatgcaattgcaatgcaaccgtaggagtgcgttgcgtaccctggtctgtccctgcggcctggcct
gcccttgttcgttgcggatgcggggggtgccgggtgggtactgtactgtactactgggtagagagatactactagatagagagagagaggtcggtca
ccccgggcgcgggacacagcctctgcgaaaaagcgatccatgtcgcgcctagctttgacccggaacggatcccccaaccaggaaccagcagagcag
gagggccaggccaccacctctcgccattccattcccggtcctagctagtcctgttctgttcctgtagcagtagcagtagctacggtactacgagtcctcctc
gacgtcccaggcactactccactccacgcagcagcaggcagcgagcatctctcgaccagatgcatacaagctacaccctcctcggctccgatcctaccc
atgccggcccaggcggcc<u>tataaaag</u>cgcaccccggcccgtcttcctcccactgcatgcccattgccctccccggccttcgccgtgccaacgaca
cacctcatcaccggccggaacattccacgaccgaagaaaccagtccctagctagtccacgcacgaccaacaaggcaggcgagcgacgacagtccaa
gcctccaagaagaagaagaagaagaagaagaagaag

Figure 10: Rice *Msca1* Genomic

```
>OsMS22 genomic
tggaacgcatggcaagaagggtagtagtacgccgtacgatcagacggttacgcgtgatgtaacgtgtcgacgatccatgatccatcgactaggaggtcatcaccggggcccacct
gcccccggggagggaggttgcgttggtgggcccgggggagtcaaacgacggcggagatgagacggagagggccccgccgttatgctgtcgggctgtcggcgcttcacacag
tggccgtccgtacgtgatgtcgcctcctccagccgtctccaagtacagctatactagtagagtagtatactactgctcctatactgtacagtatacccgtactgtactagtggcaatatc
actcaaaacacatggagcattatgtatacatacaaccatcatgaatatatattcttctagaaacgaaaaaagcatgcacatcgccccctattttggggagttagttaattagaatattcagct
gataggaatctttaaaagaatcggataattaattaaccataatttctgtcatgcagggtatcaaatgtaccacattaaattttctagcaatgtaaaatctatgcatgcaccacactggaca
gcgaaatatatactcccttcgtactcataaagggaatcgttttggacagtgacacggtctccaaaacacaactttgacttttgtttctataaaaatatttattgaaaagtgatatatgtatac
ttttatgaaagtattttcaagacaaatctattcatatattttttatattttcaaattcaataatttaaaaattattcatgatttatattctcaaggtttgacttaaatattatcctaaacgattttctttat
gagtacggagggagtatacttacaattttgtacctctcgagtacgataaaatctctctccagattttgcgcgagaatatctgaacggtttgtagctgcattatctagaagatctcttgaaaa
tgaacatagttcatatattacctcatgtatgtggtgctatatatatatatgtttcactggatggttaattacttctgggaaactgttttaacatgcaacatgtactagctagctagctccatttct
cttcattccattccagagagctcctctatttcttttactaatcttttccccctatcaaaaagccaccagctttctagtaagcaacactagtcactttaacctcctcccttgcttttgcttactacac
cttgcatctctctctggtaaccgtatcgtggtggaaggaaaggaagaaaggagtgtactgggtagctcagctcagctcagctaggcagtggccatgtcagagcgtgtgttcgccga
gctcgcgaccatccactaccaaaaaagccttccatgtcgccactcctttgaccccctcgcaccacaccaattctccatctatatatcatccaccttcttcttcctcctctcattgccattgt
gtgtttgtgttacattgcaatcgtgccatttgaagaagaggaggagaggatgaggatgcaggtggtggagacggcggcggtggaggaggaggaggcggcggcggcgatgatgt
cggtgtacgagagggtggcgaggatggcgagcgggaacgcggtggtggtgttcagcgcgagcgggtgctgcatgtgccacgtcgtcaagcgcctcctcctcggcctcggcgtc
ggccccgccgtctacgagctcgaccagctcgccgccgccgccgacatccaggccgcgctgtcgcagctcctcccgccgggccagccgccggtgcccgtcgtgttcgtcggcg
gcaggctcctcggcggcgtcgagaaggtgatggcgtgccacatcaatggcaccctcgtcccctcctcaagcaggccggcgccctctggctctgatccatccatcgatccctacc
ttgcattgattaatgtatgatgcttaattaattaatcaagattttaatctatctcaaggaggagtttgtagatataattaattaacagagtgatctatcgcgatctagcttagcttaattacctag
gttggtgtggtgtggtgtgctgttgaatcggttggttgattagcgaagagcatgcggtgtgttaattaattttaagctacttgttggtcgacgatgagtttgaaatgcaatggaaatgcagt
gcttttaattaattgcatggtgtgtacgttgttcttggctagcttttccaaaacttgagtttgtttaaaaggtgccgatcgatcaatgtgtcttcactctgatcgatcaaaaaagagaaaagag
agatacagtcatacagtagctagctagcattacacagtctaaagtttggcttcttttaaacaaaaaaaataaaaaagcaaagaagcaaaagtttggcttcttttgaacgtacagcatgag
gcacgtagcgatgtatacgctatagtactattcgttcaaactaactgatggccgtttcttacttctttctttgagctgatgagagttggttgcgagattctttcatgtggcgtgaccgtttgat
gaacaaattaaagctgcagtgtcgtccttggttcatcatcgatcgacaaacacacacacacacacacacattgcaaacaattaacagatgattgttgttggccgtcgtcatggtcg
gtcagggcagagctagtgacagtcaaaagcaacgtatacgtatacgtatgtaatggcgaaagcagcagcagctgctagctgctggttctacagtgcttttaagtggctgggtcagtc
actgcatgcaatgcaggcaaaagagctagctagaattgcatatatacatgatctgagagaaagaaagagagagagatagagaaaattatttaa
```

Figure 11: Rice *Msca1* protein

>OSMS22
MSERVFAELATIHYQKSLPCRHSFDPPRTTPILHLYIIHLLLPPLIAIVCLCYIAIVPFEEEEERMRM
QVVETAAVEEEEAAAAMMSVYERVARMASGNAVVVFSASGCCMCHVVKRLLLGLGVGPAV
YELDQLAAAADIQAALSQLLPPGQPPVPVVFVGGRLLGGVEKVMACHINGTL
VPLLKQAGALWL

Figure 12: Rice *Mscal* Promoter region tggaacgcatggcaagaagggtagtagtacgccgtacgatcagacggttacgcgtgatgtaacgtgtcgacgatccatgatccatcgactaggaggtcatcaccggggcccacctgcccccc
gggagggaggttgcgttggtgggcccgggggagtcaaacgacggcggagatgagacggagagggccccgccgttatgctgtcgggctgtcggcgcttcacacagtggccgtccgtacgtg
atgtcgcctcctccagccgtctccaagtacagctatactagtagagtagtatactactgctcctatactgtacagtatacccgtactgtactagtggcaatatcactcaaaacacatggagcattatg
tatacatacaaccatcatgaatatatattcttctagaaacgaaaaaagcatgcacatcgcccctattttggggagttagttaattagaatattcagctgataggaatctttaaaagaatcggataattaat
taaccataatttctgtcatgcagggtatcaaatgtaccacattaaattttctagcaatgtaaaatctatgcatgcaccacactggacagcgaaatatatactcccttcgtactcataaagggaatcgtttt
ggacagtgacacggtctccaaaacacaactttgacttttgtttctataaaaatatttattgaaaagtgatatatgtatacttttatgaaagtattttcaagacaaatctattcatatattttttatattttcaaat
tcaataatttaaaaattattcatgatttatattctcaaggtttgacttaaatattatcctaaacgattttctttatgagtacggagggagtatacttacaattttgtacctctcgagtacgataaaatctctctcc
agattttgcgcgagaatatctgaacggtttgtagctgcattatctagaagatctcttgaaaatgaacatagttcatatattacctcatgtatgtggtgctatatatatatatgtttcactggatggttaattac
ttctgggaaactgttttaacatgcaacatgtactagctagctagctccatttctcttcattccattccagagagctcctctatttctttactaatctttttccccctatcaaaaagccaccagctttctagtaag
caacactagtcactttaacctcctcccttgcttttgcttactacaccttgcatctctctctggtaaccgtatcgtggtggaaggaaaggaagaaaggagtgtactgggtagctcagctcagctcagcta
ggcagtggcc Figure 13: Rice *msca1* mutant allele

```
>OsMS22 mutant
ttgtaaaacgacggccagtgaattgtaatacgactcactatagggcgaattgggccctctagatgcatgctcgagcggccgccagtgtgatggatatctgcagaattcgcccttttgagcatgcatg
ctaagctagtactccagctggtagcttttggtaagcttatcatatccatcacgtcacatatatcatatatgcatgatttcttgctacctcgccactagcttttgctgaaacggtttttatattggagaaacac
gacaccgcatgcatgcatgtgccatgtacgaaatttggccccgtttagttcccaaaagttttcccaaaatcatcacatcgaattcttggatatatgcatggagcattaaatataaattaaaagaaaaa
ctaattacacagttaagggggaaatcgcgagacaaatattttgagcttaatttgttcatgattagccataagtgctacagtaacccacatgtgctaatgatggattaattaggctcaaaagattcgtctc
gcggtttccatgcgagttacgaaattagtttttcatttgtgtccgaaaaccccttctgacattcggtcaaacatccgatgtgacacccaaaaaattttatttcacgactaaacatgcccttgtttcataaat
ttaagttgcttttcatgcatgcaaaccaaagtaaactactgtagcttagtaaatttgcaaacttcgccttttcccccccagtggagatgcatgcatgcgacgcattaatgatcgacatatatatgtcgatca
ttaactgatgatcactgatcatatcgatagaaatcataagattgatgtttgtgttgtaaccagggtttaccttaccgccggggccggggttaccgtgccccggcggtaagcacggttaccgcgcggt
aaccgcggtaaccgtgaaaaaccgtacaaaaccgtgcaaaatttatcaaaaattcaaattattttttaaatttatttgtatttaaggaggttaccgcggtatttatattaccgtaccccccgcggtaagccc
ggtaaccgcgcggttaccggcggtaagttaaaccctggttgtaactcgcagtggttgtcattgtgaatcggccgatacaatacgtcaatatgatcatagacgcgactttgttaatccatcatatatatc
tcaatcgatctgcaatatgtgtgtgaaccgtgtgcatgtcgtcgaatctttgacaacatctatcgatatcgatctcctcagatggatcgatcgatatcatatgaacaatgcattgcagcggtgggccat
cacagggcatgcatgcaaccatgcaaggcaccagctaccttctattttggcatgcatttcattactacgccatgcaattaacccagagagacagcgtctcaactagcaacatactctctccgtctca
aaatataagatattttagttggatgtgacattcttagtactccctccatccacaaaagttagacatatttcacatttgagtttttccaaataagttgttcctatttgtagtctttatgtatttaagacttaaatgaa
gagataaattaaatgttttatgagaacccaaggagtcatccaaatactcattggttgcatgcttgcattcactccttgattttgtaacatccaagaagatttaatttctcattggtctttgtgacaaaagtaa
tatgcgtaacttttgtggatggagggagtactacgaatctgaacaggcagtagtactaggatacatgtgtcacatctatctaaaatctctcttattttgggacggatggagtatactccctccgtactcc
taaaggaagtcgtttaggacagcgacatggtctccaaaacacaactttgacttcttgtttctataaaaatatttattgaaaagtgatatatgtatactttatgaaagtattttcaagacaaatctattcatat
aattttttacattttcaaaatcaataacttgagagttattcgtgatttatattcctaaggtttgacttaaacattatcctaaacgactttcttttatgagtacaatgagtacagagggagtattaattaatcaatcg
agggactggaccagccaatagatatatatgatgtggccaagctgaaattaaattatgtctgtacctaaagcatgcataattaatgaacattatgtatagtaagagcgagtttaatagtagagctaatta
ttggctaatagcctattttagatctaacatgtataataagttatcattcctcatttctctctcacataagcttatagtacgggcttatattccactattatccttgctctaaagcataatatatgtcttgctcgtag
tgtggagtgtggaaatgtagagtatgaaaagagagagaaaaaacaggcaagagaaaaacctatgagaaaaaaccataattcacatgcatatacacttaaacaaaaaacgaatagacattgtaac
ccttaattcttgtaatctaattaagtgctatataattcaaaaaacaatcaacgtattcatgatatatttaaaattctaatatttataatatgaataaatgataacccagtcatgcaatgtgaacgagttgataa
ctcgtttaagaaaaaaaataataataaggtattgtgcttcttaattcaacggaagcacctcacatatatcaatacaaaactaatcaaaaagactaaactaccctcatttattaaattccaatgcaattatt
ccactccttatcaattcccaacacatttttatccatccatcgatccctaccttgcattgattaatgtgtgatgcttaattaattaatcaagattttaatctacctcaaggaggagtttgtagatataattaatta
acagagtgatctatcgcgatctagcttaatcacctaggttggtgtggtggtgtgctgttgaatcggttggttaattagcgaagagcatgcggtgtgttaattaattttaagctacttgttggtc
gacgatgagtttgaaatgcaatggaaatgcagtgcttttaattaattgcatggtgtgtacgttgttcttggctagcttttccaaaacttgagtttgtttaaaaggtgccgatcgatcaatgtgtcttcactct
gatcgatcaaaaagagaaaagagagatacagtcatacagtagctagctagcaatacacagtctgaagtttggcttcatttaaacaaaaaaaataaaaaagcaaagaagcaaaagtttggcttctt
ttgaacgtacagcatgaggcacgtagcgatgtatacgctatagtactattcgttcaaactaactgatggccgtttcttactttctttctttgagctgatgagagttggttgcgagattctttcatgtggcat
gaccgtcatttccacagttcagtcactgaagcttgacttgaaaatgaacatcagtcaacagggacaaaaaaaaaatttacggaccaaataacgcctgttattatcctactaaaaatcgtcttcgttgtc
accatcagagaggatcacaagggcgaattccagcacactggcggccgttactagtg
```

MSCA1 NUCLEOTIDE SEQUENCES IMPACTING PLANT MALE FERTILITY AND METHOD OF USING SAME

BACKGROUND OF THE INVENTION

Development of hybrid plant breeding has made possible considerable advances in quality and quantity of crops produced. Increased yield and combination of desirable characteristics, such as resistance to disease and insects, heat and drought tolerance, along with variations in plant composition are all possible because of hybridization procedures. These procedures frequently rely heavily on providing for a male parent contributing pollen to a female parent to produce the resulting hybrid.

Field crops are bred through techniques that take advantage of the plant's method of pollination. A plant is self-pollinating if pollen from one flower is transferred to the same or another flower of the same plant or a genetically identical plant. A plant is cross-pollinated if the pollen comes from a flower on a different plant.

In certain species, such as *Brassica campestris*, the plant is normally self-sterile and can only be cross-pollinated. In self-pollinating species, such as soybeans and cotton, the male and female plants are anatomically juxtaposed. During natural pollination, the male reproductive organs of a given flower pollinate the female reproductive organs of the same flower.

Maize plants (*Zea mays* L.) present a unique situation in that they can be bred by both self-pollination and cross-pollination techniques. Maize has male flowers, located on the tassel, and female flowers, located on the ear, on the same plant. It can self or cross pollinate. Natural pollination occurs in maize when wind blows pollen from the tassels to the silks that protrude from the tops of the incipient ears.

The development of maize hybrids requires the development of homozygous inbred lines, the crossing of these lines, and the evaluation of the crosses. Pedigree breeding and recurrent selection are two of the breeding methods used to develop inbred lines from populations. Breeding programs combine desirable traits from two or more inbred lines or various broad-based sources into breeding pools from which new inbred lines are developed by selfing and selection of desired phenotypes. A hybrid maize variety is the cross of two such inbred lines, each of which may have one or more desirable characteristics lacked by the other or which complement the other. The new inbreds are crossed with other inbred lines and the hybrids from these crosses are evaluated to determine which have commercial potential. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

Hybrid maize seed can be produced by a male sterility system incorporating manual detasseling. To produce hybrid seed, the male tassel is removed from the growing female inbred parent, which can be planted in various alternating row patterns with the male inbred parent. Consequently, providing that there is sufficient isolation from sources of foreign maize pollen, the ears of the female inbred will be fertilized only with pollen from the male inbred. The resulting seed is therefore hybrid ($F_1$) and will form hybrid plants.

Field variation impacting plant development can result in plants tasseling after manual detasseling of the female parent is completed. Or, a female inbred plant tassel may not be completely removed during the detasseling process. In any event, the result is that the female plant will successfully shed pollen and some female plants will be self-pollinated. This will result in seed of the female inbred being harvested along with the hybrid seed which is normally produced. Female inbred seed does not exhibit heterosis and therefore is not as productive as $F_1$ seed. In addition, the presence of female inbred seed can represent a germplasm security risk for the company producing the hybrid.

Alternatively, the female inbred can be mechanically detasseled by machine. Mechanical detasseling is approximately as reliable as hand detasseling, but is faster and less costly. However, most detasseling machines produce more damage to the plants than hand detasseling. Thus, no form of detasseling is presently entirely satisfactory, and a need continues to exist for alternatives which further reduce production costs and to eliminate self-pollination of the female parent in the production of hybrid seed.

A reliable system of genetic male sterility would provide advantages. The laborious detasseling process can be avoided in some genotypes by using cytoplasmic male-sterile (CMS) inbreds. In the absence of a fertility restorer gene, plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Usually seed from detasseled normal maize and CMS produced seed of the same hybrid must be blended to insure that adequate pollen loads are available for fertilization when the hybrid plants are grown and to insure cytoplasmic diversity.

One type of genetic sterility is disclosed in U.S. Pat. Nos. 4,654,465 and 4,727,219 to Brar, et al. However, this form of genetic male sterility requires maintenance of multiple mutant genes at separate locations within the genome and requires a complex marker system to track the genes and make use of the system convenient. Patterson also described a genic system of chromosomal translocations which can be effective, but which are complicated. (See, U.S. Pat. Nos. 3,861,709 and 3,710,511.)

Many other attempts have been made to improve on these systems. For example, Fabijanski, et al., developed several methods of causing male sterility in plants (see EPO 89/3010153.8 publication no. 329,308 and PCT application PCT/CA90/00037 published as WO 90/08828). One method includes delivering into the plant a gene encoding a cytotoxic substance associated with a male tissue specific promoter. Another involves an antisense system in which a gene critical to fertility is identified and an antisense to the gene inserted in the plant. Fabijanski, et al. also shows several cytotoxic antisense systems. See EP0329308. Still other systems use "repressor" genes which inhibit the expression of another gene critical to male sterility. See PCT/GB90/00102, published as WO 90/08829. For yet another example see U.S. Pat. No. 6,281,348.

A still further improvement of this system is one described at U.S. Pat. No. 5,478,369 in which a method of imparting controllable male sterility is achieved by inactivating or otherwise silencing a gene native to the plant that is critical for male fertility and transforming that plant with the gene critical to male fertility linked to an inducible promoter controlling expression of the gene. That is, the expression of the endogenous sequence is prevented, by any of the methods known to a skilled person in the art for preventing expression of a sequence (such an antisense methods, cosuppression, mutation, use of ribozymes or hairpins, various repression systems and the like, discussed infra.) The plant is thus constitutively sterile, becoming fertile only when the promoter is induced and its linked male fertility gene is expressed.

In a number of circumstances, a male sterility plant trait is expressed by maintenance of a homozygous recessive condition. Difficulties arise in maintaining the homozygous condition, when a restoration gene must be used for maintenance. For example, a natural mutation in a gene critical to male fertility can impart a male sterility phenotype to plants when this mutant allele is in the homozygous state. But because this homozygosity results in male sterility, the homozygous male-sterile line cannot be maintained. Fertility is restored when the non-mutant form of the gene is introduced into the plant. However, this form of line maintenance removes the desired homozygous recessive condition, restores full male fertility in half of the resulting progeny, and prevents maintenance of pure male sterile maternal lines. These issues can be avoided where production of pollen containing the restoration gene is eliminated, thus providing a maintainer plant producing only pollen not containing the restoration gene, and the progeny retain their homozygous condition when fertilized by such pollen. An example of one approach is shown in Dellaporta et al., U.S. Pat. No. 6,743,968, in which a plant is produced having a hemizygotic construct comprising a gene that produces a product fatal to a cell, linked with a pollen-specific promoter, and the restoration gene. When crossed with the homozygous recessive male sterile plant, the progeny thus retains the homozygous recessive condition.

As noted, an essential aspect of much of the work underway with male sterility systems is the identification of genes impacting male fertility. Such a gene can be used in a variety of systems to control male fertility including those described herein.

Genetic male sterility results from a mutation, suppression, or other impact to one of the genes critical to a specific step in microsporogenesis, the term applied to the entire process of pollen formation. These genes can be collectively referred to as male fertility genes (or, alternatively, male sterility genes). There are many steps in the overall pathway where gene function impacts fertility. This seems aptly supported by the frequency of genetic male sterility in maize. New alleles of male sterility mutants are uncovered in materials that range from elite inbreds to unadapted populations.

At U.S. Pat. No. 5,478,369 there is described a method by which the Ms45 male fertility gene was tagged and cloned on maize chromosome 9. Previously, there had been described a male sterility gene on chromosome 9, ms2, which had never been cloned and sequenced. It is not allelic to the gene referred to in the '369 patent. See Albertsen, M. and Phillips, R. L., "Developmental Cytology of 13 Genetic Male Sterile Loci in Maize" *Canadian Journal of Genetics & Cytology* 23:195-208 (January 1981). The only fertility gene cloned before that had been the *Arabadopsis* gene described at Aarts, et al., supra.

Examples of genes that have been discovered subsequently that are critical to male fertility are numerous and include the *Arabidopsis* ABORTED MICROSPORES (AMS) gene, Sorensen et al., *The Plant Journal* (2003) 33(2):413-423); the *Arabidopsis* MS1 gene (Wilson et al., *The Plant Journal* (2001) 39(2):170-181); the NEF1 gene (Ariizumi et al., The Plant Journal (2004) 39(2):170-181); *Arabidopsis* AtGPAT1 gene (Zheng et al., *The Plant Cell* (2003) 15:1872-1887); the *Arabdiopsis* dde2-2 mutation was shown to be defective in the allene oxide syntase gene (Malek et al., *Planta* (2002)216: 187-192); the *Arabidopsis* faceless pollen-1 gene (flp1) (Ariizumi et al, Plant Mol. Biol. (2003) 53:107-116); the *Arabidopisis* MALE MEIOCYTE DEATH1 gene (Yang et al., *The Plant Cell* (2003) 15: 1281-1295); the tapetum-specific zinc finger gene, TAZ1 (Kapoor et al., *The Plant Cell* (2002) 14:2353-2367); and the TAPETUM DETERMINANT1 gene (Lan et al, *The Plant Cell* (2003) 15:2792-2804).

The table below lists a number of known male fertility mutants or genes from *Zea mays*.

| GENE NAME | ALTERNATE NAME | REFERENCE |
|---|---|---|
| ms1 male sterile1 | male sterile1, ms1 | Singleton, WR and Jones, DF. 1930. J Hered 21: 266-268 |
| ms10 male sterile10 | male sterile10, ms10 | Beadle, GW. 1932. Genetics 17: 413-431 |
| ms11 male sterile11 | ms11, male sterile11 | Beadle, GW. 1932. Genetics 17: 413-431 |
| ms12 male sterile12 | ms12, male sterile12 | Beadle, GW. 1932. Genetics 17: 413-431 |
| ms13 male sterile13 | ms*-6060, male sterile13, ms13 | Beadle, GW. 1932. Genetics 17: 413-431 |
| ms14 male sterile14 | ms14, male sterile14 | Beadle, GW. 1932. Genetics 17: 413-431 |
| ms17 male sterile17 | ms17, male sterile17 | Emerson, RA. 1932. Science 75: 566 |
| ms2 male sterile2 | male sterile2, ms2 | Eyster, WH. 1931. J Hered 22: 99-102 |
| ms20 male sterile20 | ms20, male sterile20 | Eyster, WH. 1934. Genetics of *Zea mays*. Bibliographia Genetica 11: 187-392 |
| ms23 male sterile23 | ms*-6059, ms*-6031, ms*-6027, ms*-6018, ms*-6011, ms35, male sterile23, ms*-Bear7, ms23 | West, DP and Albertsen, MC. 1985. MNL 59: 87 |
| ms24 male sterile24 | ms24, male sterile24 | West, DP and Albertsen, MC. 1985. MNL 59: 87 |
| ms25 male sterile25 | ms*-6065, ms*-6057, ms25, male sterile25, ms*-6022 | Loukides, CA; Broadwater, AH; Bedinger, PA. 1995. Am J Bot 82: 1017-1023 |
| ms27 male sterile27 | ms27, male sterile27 | Albertsen, MC. 1996. MNL 70: 30-31 |

-continued

| GENE NAME | ALTERNATE NAME | REFERENCE |
|---|---|---|
| ms28 male sterile28 | ms28, male sterile28 | Golubovskaya, IN. 1979. MNL 53: 66-70 |
| ms29 male sterile29 | male sterile29, ms*-JH84A, ms29 | Trimnell, MR et al. 1998. MNL 72: 37-38 |
| ms3 male sterile3 | Group 3, ms3, male sterile3 | Eyster, WH. 1931. J Hered 22: 99-102 |
| ms30 male sterile30 | ms30, msx, ms*-6028, ms*-Li89, male sterile30, ms*-LI89 | Albertsen, MC et al. 1999. MNL 73: 48 |
| ms31 male sterile31 | ms*-CG889D, ms31, male sterile31 | Trimnell, MR et al. 1998. MNL 72: 38 |
| ms32 male sterile32 | male sterile32, ms32 | Trimnell, MR et al. 1999. MNL 73: 48-49 |
| ms33 male sterile33 | ms*-6054, ms*-6024, ms33, ms*-GC89A, ms*-6029, male sterile6019, Group 7, ms*-6038, ms*-Stan1, ms*-6041, ms*-6019, male sterile33 | Patterson, EB. 1995. MNL 69: 126-128 |
| ms34 male sterile34 | Group 1, ms*-6014, ms*-6010, male sterile34, ms34, ms*-6013, ms*-6004, male sterile6004 | Patterson, EB. 1995. MNL 69: 126-128 |
| ms36 male sterile36 | male sterile36, ms*-MS85A, ms36 | Trimnell, MR et al. 1999. MNL 73: 49-50 |
| ms37 male sterile 37 | ms*-SB177, ms37, male sterile 37 | Trimnell, MR et al. 1999. MNL 73: 48 |
| ms38 male sterile38 | ms30, ms38, ms*-WL87A, male sterile38 | Albertsen, MC et al. 1996. MNL 70: 30 |
| ms43 male sterile43 | ms43, male sterile43, ms29 | Golubovskaya, IN. 1979. Int Rev Cytol 58: 247-290 |
| ms45 male sterile45 | Group 6, male sterile45, ms*-6006, ms*-6040, ms*-BS1, ms*-BS2, ms*-BS3, ms45, ms45'-9301 | Albertsen, MC; Fox, TW; Trimnell, MR. 1993. Proc Annu Corn Sorghum Ind Res Conf 48: 224-233 |
| ms48 male sterile48 | male sterile48, ms*-6049, ms48 | Trimnell, M et al. 2002. MNL 76: 38 |
| ms5 male sterile5 | ms*-6061, ms*-6048, ms*-6062, male sterile5, ms5 | Beadle, GW. 1932. Genetics 17: 413-431 |
| ms50 male sterile50 | ms50, male sterile50, ms*-6055, ms*-6026 | Trimnell, M et al. 2002. MNL 76: 39 |
| ms7 male sterile7 | ms7, male sterile7 | Beadle, GW. 1932. Genetics 17: 413-431 |
| ms8 male sterile8 | male sterile8, ms8 | Beadle, GW. 1932. Genetics 17: 413-431 |
| ms9 male sterile9 | Group 5, male sterile9, ms9 | Beadle, GW. 1932. Genetics 17: 413-431 |
| ms49 male sterile49 | ms*-MB92, ms49, male sterile49 | Trimnell, M et al. 2002. MNL 76: 38-39 |

There remains a need to identify nucleotide sequences critical to male fertility in plants. There also remains a need to identify regulatory regions which preferentially direct expression to male tissue of a plant.

In the present invention the inventors provide novel DNA molecules and the amino acid sequence encoded that are critical to male fertility in plants. These can be used in any of the systems where control of fertility is useful, including those described above.

Thus, one object of the invention is to provide a nucleic acid sequence, the expression of which is critical to male fertility in plants and in which a mutation of the sequence causes male sterility when in the homozygous state.

Another object is to provide regulatory regions that preferentially direct expression of operably linked nucleotide sequences to male tissue(s) of a plant.

A further object of the invention is to provide a method of using such nucleotide sequences to mediate male fertility in plants.

Further objects of the invention will become apparent in the description and claims that follow.

SUMMARY OF THE INVENTION

This invention relates to nucleic acid sequences, and, specifically, DNA molecules and the amino acid encoded by the DNA molecules, which are critical to male fertility. Impacting the functional expression of such sequences results in the mediation of male fertility. Regulatory regions directing expression preferentially to male tissue are also provided. The invention also relates to use of such nucleotide sequences to mediate fertility in plants.

BRIEF DESCRIPTION OF THE DRAWINGS

FIG. 2 is the nucleotide sequence of the Msca1 gene (SEQ ID NO: 1)
FIG. 3 is the protein sequence of Msca1 (SEQ ID NO: 2)
FIG. 4 is the msca1-ref nucleotide sequence (SEQ ID NO: 3)
FIG. 5 is an alignment of fertile and sterile msca1-mg12 alleles, (the nucleotide sequence of the fertile is SEQ ID NO: 4; the protein sequence is SEQ ID NO: 5; the nucleotide sequence of msca1-mg12 sterile is SEQ ID NO: 6 and the protein sequence is SEQ ID NO: 7). The fertile allele sequence contains an additional 490 base pairs deleted from the 3' region of the sterile sequence.

FIG. 6 shows alignment of the Msca1 wildtype gene from the corn hybrid Missouri 17 (Mo17) (SEQ ID NO: 8) with msca1-mg12 alleles in a fertile plant (Mg12-Fert) (SEQ ID NO: 9) and a sterile plant (Mg12-Ster) (SEQ ID NO: 10). The circled region refers to the CCMC redox motif (SEQ ID NO: 11) and the gluteredoxin binding site (GSH Binding) (SEQ ID NO: 12) is underlined.

FIGS. 7A-7F show alignment of the msca1 alleles, Ms22-6036 from a fertile plant (Fert) SEQ ID NO: 13, coding SEQ ID NO: 23) with a sterile plant (6036s) (SEQ ID NO: 14, coding SEQ ID NO: 24). The sterile sequence contains an 850 base pair insertion at the 3' end. The insertion contains small perfect TIRs of eight basepairs (indicated at "TIR") with about 200 basepairs of a transposon-like sequence.

FIG. 8 shows a graphic alignment of the Msca1 sequence with mutant alleles msca1-ref, msca1-mg12 and msca1-6036.

FIG. 9 is the full length promoter of Msca1 (SEQ ID NO: 15)

FIG. 10 is the nucleotide sequence of the rice Msca1 gene (SEQ ID NO: 16)

FIG. 11 is the protein sequence of rice Msca1 (SEQ ID NO: 17)

FIG. 12 is the full length promoter of rice Msca1 (SEQ ID NO: 18)

FIG. 13 is the sequence of the rice msca1 allele (SEQ ID NO: 19).

DISCLOSURE OF THE INVENTION

Figure 1:
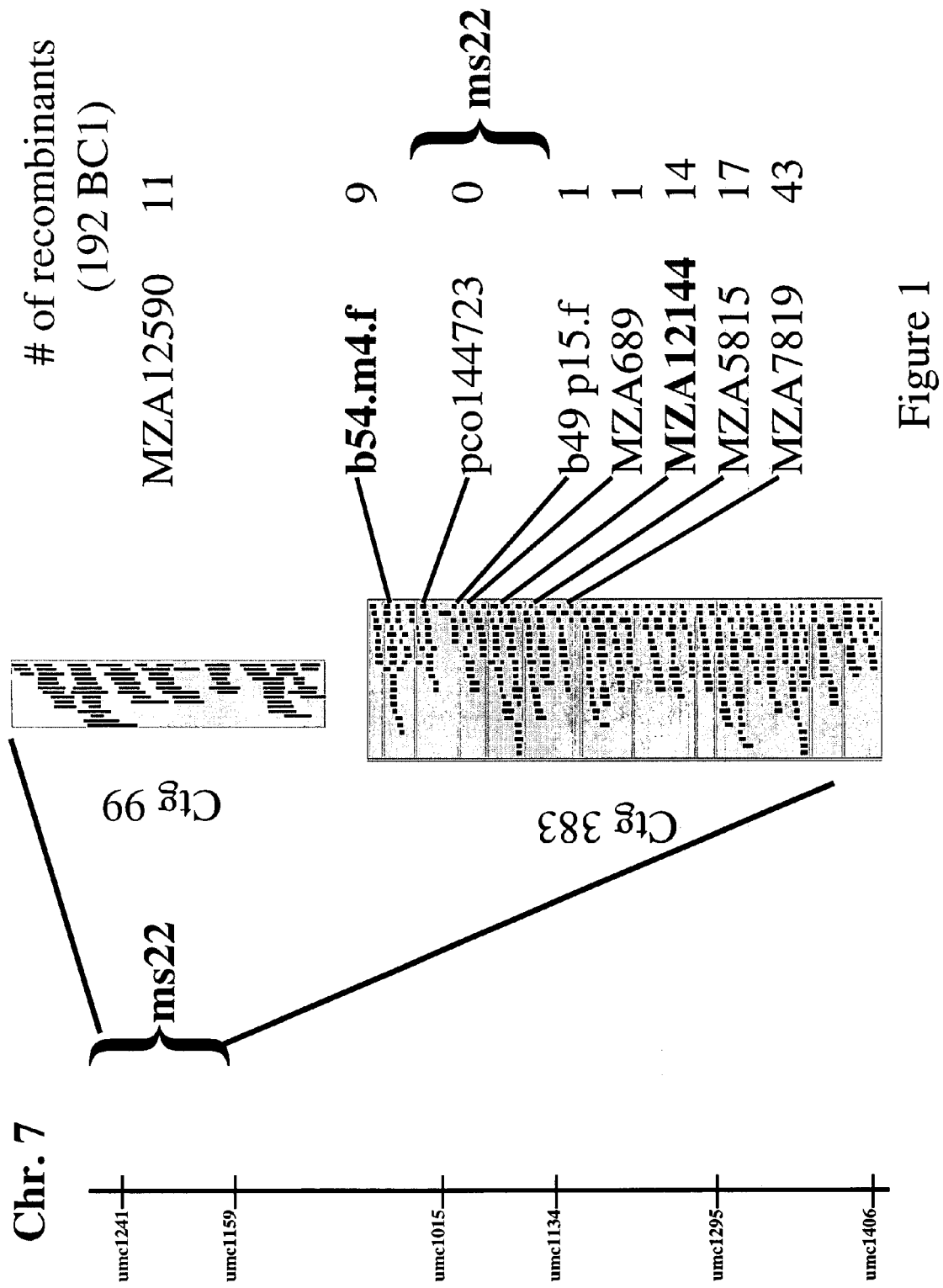
FIG. 1 is a locus map of the male fertility gene Msca1.

All references referred to are incorporated herein by reference.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

The invention includes using the sequences shown herein to impact male fertility in a plant, that is, to control male fertility by manipulation of the genome using the genes of the invention. By way of example, without limitation, any of the methods described infra can be used with the sequence of the invention such as introducing a mutant sequence into a plant to cause sterility, causing mutation to the native sequence, introducing an antisense of the sequence into the plant, use of hairpin formations, linking it with other sequences to control its expression, or any one of a myriad of processes available to one skilled in the art to impact male fertility in a plant.

The Msca1 gene (also referred to as Ms22) described herein is located on short arm of maize chromosome 7 and its dominant allele encodes a protein critical to male fertility. The locus map is represented at FIG. 1. The Msca1 gene can be used in the systems described above, and other systems impacting male fertility.

Mutations referred to as ms22 or msca1 were first noted as phenotypically male sterile with anthers did not exude from the tassel and lacked sporogenous tissue. West and Albertsen (1985) *Maize Newsletter* 59:87; Neuffer et al. (1977) Mutants of maize. *Cold Spring Harbor Laboratory Press*, Cold Spring Harbor, N.Y. The mutant locus was originally referred to as ms22 but was later changed to msca1, or male sterile converted anther. See Chaubal et al. "The transformation of anthers in the msca1 mutant of maize" *Planta* (2003)216: 778-788.

Study of the mutant included collecting anthers from young spikelets of immature tassels in plant families segregating 1:1 for male sterile/male fertility plants for microscopic study. Using an $F_2$ family segregating for the msca1 mutation, DNA was isolated from male sterile plants, electrophoresed and hybridized with restriction fragment length polymorphism markers, and mapped to chromosome 7. See Chaubal et al. "The transformation of anthers in the msca1 mutant of maize" *Planta* (2003)216:778-788.

The msca1 mutants are unusual in that stamen primordia develop normally, but differentiation and cell division do not occur, with the tissue instead developing into nonfunctional vascular tissue. There is no asymmetric division of archesporial cells into large primary sporogenous and smaller primary parietal cells. Instead, the anther contains parenchymal cells and non-functional vascular strands with no formation of normal anther cells such as microspores, tapetum, middle layer and endothecium. All of the cell layers of the anther convert in mutant plants into vegetative structures. Since the Msca1 gene operates after stamen primordial initiation and before division of the archesporial cells, interruption of gene expression acts as a developmental block. As opposed to other male sterility genes such as MAC1, EMS1 or GNE2 (Sorensen et al. (2002) *Plant J.* 29:581-594) rather than breaking down cells in the quartet stage, microspores never develop. Mutations in the SPOROCYTELESS/NOZZLE gene act early in development, but impact both anther and ovule formation such that plants are male and female sterile. Yang et al. The SPOROCYTELESS gene of *Arabidopsis* is required for initiation of sporogenesis and encodes a novel nuclear protein. Genes Dev. 1999 Aug. 15; 13(16):2108-17. The Msca1 gene expression when interrupted does not impact floral tissue. Rather, the anther is transformed into a vegetative structure and microsporogenesis never begins and the end result is greatly increased reliability in maintenance of male sterility.

The invention is also directed to impacting male fertility of a plant by impacting the Msca1 nucleotide sequence. Impacting male fertility refers to a change in the male fertility of the plant from the fertility phenotype prior to impacting the nucleotide sequence. It may result in male sterility, as when the sequence is impacted such that expression of the Msca1 male fertility critical gene does not occur as in the wild-type condition. The fertility of a plant may also be impacted by, for example, introducing into a plant that comprises a mutated msca1 allele, a Msca1 nucleotide sequence which restores fertility. Clearly, many variations are possible in impacting male fertility depending upon the specific application. Impacting the Msca1 nucleotide sequence can be accomplished using many tools available to one skilled in the art, as discussed in examples below. By way of example, the gene may contain an insertion, such as that shown in msca1-6036 allele, or have a deletion, such as with msca1-mg12 allele. Use of mutagenesis, antisense genes, co-suppression, hairpin formations, selecting for mutant plants, insertion of one or more additional sequences which act to disrupt the gene expression are a few examples of the many means available to interrupt expression of the Msca1 gene. Further, the invention is directed to restoring male fertility in a plant having expression of Msca1 disrupted, by introducing into the plant the wild-type Msca1 complementary sequence.

It will be evident to one skilled in the art that variations, mutations, derivations including fragments smaller than the entire sequence set forth may be used which retain the male sterility controlling properties of the gene. As used herein, a "functional fragment" of the Msca1 sequence is a nucleotide sequence that is formed by one or more deletions from the entire sequence and which retains the functional of being critical for male fertility. One of ordinary skill in the art can readily assess the variant or fragment by its introduction into plants homozygous for a stable male sterile allele of Msca1, followed by observation of the plant's male tissue development.

The sequences of the invention may be isolated from any plant, including, but not limited to corn (*Zea mays*), canola (*Brassica napus, Brassica rapa* ssp.), alfalfa (*Medicago sativa*), rice (*Oryza sativa*), rye (*Secale cereals*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), millet (*Panicum* spp.), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats (*Avena sativa*), barley (*Hordeum vulgare*), vegetables, ornamentals, and conifers. Preferably, plants include corn, soybean, sunflower, safflower, canola, wheat, barley, rye, alfalfa, rice, cotton and sorghum.

Sequences from other plants may be isolated according to well-known techniques based on their sequence homology to the homologous coding region of the sequences set forth herein. In these techniques, all or part of the known coding sequence is used as a probe which selectively hybridizes to other sequences present in a population of cloned genomic DNA fragments (i.e. genomic libraries) from a chosen organism. Methods are readily available in the art for the hybridization of nucleic acid sequences. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

Thus the invention also includes those nucleotide sequences which selectively hybridize to the Msca1 nucleotide sequences under stringent conditions. In referring to a sequence that "selectively hybridizes" with Msca1, the term includes reference to hybridization, under stringent hybridization conditions, of a nucleic acid sequence to the specified nucleic acid target sequence to a detectably greater degree than its hybridization to non-target nucleic acid.

The terms "stringent conditions" or "stringent hybridization conditions" includes reference to conditions under which a probe will hybridize to its target sequence, to a detectably greater degree than to other sequences. Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Generally, probes of this type are in a range of about 1000 nucleotides in length to about 250 nucleotides in length.

An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995). See also Sambrook et al. (1989) *Molecular Cloning: A Laboratory Manual* (2nd ed. Cold Spring Harbor Laboratory, Cold Spring Harbor, N.Y.).

In general, sequences that correspond to the nucleotide sequences of the present invention and hybridize to the nucleotide sequence disclosed herein will be at least 50% homologous, 70% homologous, and even 85%, 86%, 87%, 88%, 89%, 90%, 91%, 92%, 93%, 94%, 95%, 96%, 97%, 98%, 99% homologous or more with the disclosed sequence. That is, the sequence similarity between probe and target may range, sharing at least about 50%, about 70%, and even about 85% or more sequence similarity.

Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

Preferred hybridization conditions for the nucleotide sequence of the invention include hybridization at 42° C. in 50% (w/v) formamide, 6×SSC, 0.5% (w/v) SDS, 100 (g/ml salmon sperm DNA. Exemplary low stringency washing conditions include hybridization at 42° C. in a solution of 2×SSC, 0.5% (w/v) SDS for 30 minutes and repeating. Exemplary moderate stringency conditions include a wash in 2×SSC, 0.5% (w/v) SDS at 50° C. for 30 minutes and repeating. Exemplary high stringency conditions include a wash in 0.1× SSC, 0.1% (w/v) SDS, at 65° C. for 30 minutes to one hour and repeating. Sequences that correspond to the promoter of the present invention may be obtained using all the above conditions. For purposes of defining the invention, the high stringency conditions are used.

The following terms are used to describe the sequence relationships between two or more nucleic acids or polynucleotides: (a) "reference sequence", (b) "comparison window", (c) "sequence identity", and (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, or 100 nucleotides in length, or longer. Those of skill in the art understand that to avoid a high similarity to a reference sequence due to inclusion of gaps in the polynucleotide sequence a gap penalty is typically introduced and is subtracted from the number of matches.

Methods of aligning sequences for comparison are well-known in the art. Thus, the determination of percent sequence identity between any two sequences can be accomplished using a mathematical algorithm. Non-limiting examples of such mathematical algorithms are the algorithm of Myers and Miller (1988) *CABIOS* 4: 11-17; the local alignment algorithm of Smith et al. (1981) *Adv. Appl. Math.* 2: 482; the global alignment algorithm of Needleman and Wunsch (1970) *J. Mol. Biol.* 48: 443-453; the search-for-local-alignment-method of Pearson and Lipman (1988) *Proc. Natl. Acad. Sci.* 85: 2444-2448; the algorithm of Karlin and Altschul (1990) *Proc. Natl. Acad. Sci. USA* 87: 2264, modified as in Karlin and Altschul (1993) *Proc. Natl. Acad. Sci. USA* 90: 5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73: 237-244 (1988); Higgins et al. (1989) *CABIOS* 5: 151-153; Corpet et al. (1988) *Nucleic Acids Res.* 16: 10881-90; Huang et al. (1992) *CABIOS* 8: 155-65; and Pearson et al. (1994) *Meth. Mol. Biol.* 24: 307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215: 403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25: 3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3 and the nwsgapdna.cmp scoring matrix; % identity and % similarity for an amino acid sequence using GAP Weight of 8 and Length Weight of 2; and the BLOSUM62 scoring matrix or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

Identity to the sequence of the present invention would mean a polynucleotide sequence having at least 65% sequence identity, more preferably at least 70% sequence identity, more preferably at least 75% sequence identity, more preferably at least 80% identity, more preferably at least 85% 86%, 87%, 88%, 89%, 90%, 91%, 92%, 93%, 94%, 95%, 96%, 97%, 98%, 99% sequence identity.

The promoter of the Msca1 gene is also the subject of the present invention, as shown in the 1132 base pair sequence of FIG. 9 (SEQ ID NO: 15). The regulatory region of the gene comprises bases 1 to 1132 of FIG. 9, SEQ ID NO: 15 and other functional fragments of same. Promoter regions can be readily identified by one skilled in the art. The putative start codon containing the ATG motif is identified at base 1133 of SEQ ID NO: 1 (See FIG. 2) and upstream from the start codon is the presumptive promoter.

By "promoter" is intended a regulatory region of DNA usually comprising a TATA box capable of directing RNA polymerase II to initiate RNA synthesis at the appropriate transcription initiation site for a particular coding sequence. A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the region upstream of the TATA box from the particular promoter region identified herein. Thus the promoter region disclosed herein is generally further defined by comprising upstream regulatory elements such as those responsible for tissue and temporal expression of the coding sequence, enhancers and the like. In the same manner, the promoter elements which enable expression in the desired tissue such as male tissue can be identified, isolated, and used with other core promoters to confirm male tissue-preferred expression. By core promoter is meant the minimal sequence required to initiate transcription, such as the sequence called the TATA box which is common to promoters in genes encoding proteins. Thus the upstream promoter of Msca1 can optionally be used in conjunction with its own or core promoters from other sources. The promoter may be native or non-native to the cell in which it is found.

By way of example, a putative TATA box can be identified by primer extension analysis as described in by *Current Protocols in Molecular Biology*, Ausubel, F. M. et al. eds; John Wiley and Sons, New York pp. 4.8.1-4.8.5 (1987). Regulatory regions of anther genes, such as promoters, may be identified in genomic subclones using functional analysis, usually verified by the observation of reporter gene expression in anther tissue and a lower level or absence of reporter gene expression in non-anther tissue. The possibility of the regulatory regions residing "upstream" or 5' ward of the translational start site can be tested by subcloning a DNA fragment that contains the upstream region into expression vectors for transient expression experiments. It is expected that smaller subgenomic fragments may contain the regions essential for male-tissue preferred expression. For example, the essential regions of the CaMV 19S and 35S promoters have been identified in relatively small fragments derived from larger genomic pieces as described in U.S. Pat. No. 5,352,605.

The selection of an appropriate expression vector with which to test for functional expression will depend upon the host and the method of introducing the expression vector into the host and such methods are well known to one skilled in the art. For eukaryotes, the regions in the vector include regions that control initiation of transcription and control processing. These regions are operably linked to a reporter gene such as CYP, UidA, encoding glucuronidase (GUS), or luciferase as described herein. Expression vectors containing putative regulatory regions located in genomic fragments can be introduced into intact tissues such as staged anthers, embryos or into callus. Methods of DNA delivery are described below. For the transient assay system, various analysis may be employed. In one example, staged, isolated anthers are immediately placed onto tassel culture medium (Pareddy, D. R. and J. F. Petelino, *Crop Sci. J.*; Vol. 29; pp. 1564-1566; (1989)) solidified with 0.5% Phytagel (Sigma, St. Louis) or other solidifying media. The expression vector DNA is introduced within 5 hours preferably by microprojectile-mediated delivery with 1.2 µm particles at 1000-1100 Psi. After DNA delivery, the anthers are incubated at 26° C. upon the same tassel culture medium for 17 hours and analyzed by preparing a whole tissue homogenate and assaying for GUS or for lucifierase activity (see Gruber, et al., supra).

The isolated promoter sequence of the present invention can be modified to provide for a range of expression levels of the heterologous nucleotide sequence. Less than the entire promoter region can be utilized and the ability to drive anther-preferred expression retained. However, it is recognized that expression levels of mRNA can be decreased with deletions of portions of the promoter sequence. Thus, the promoter can be modified to be a weak or strong promoter. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. Generally, at least about 30 nucleotides of an isolated promoter sequence will be used to drive expression of a nucleotide sequence. It is recognized that to increase transcription levels, enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

The promoter of the present invention can be isolated from the 5' region of its native coding region or 5' untranslated region (5'UTR). Likewise the terminator can be isolated from the 3' region flanking its respective stop codon. The term "isolated" refers to material such as a nucleic acid or protein which is substantially or essentially free from components which normally accompany or interact with the material as found in it naturally occurring environment, or if the material is in its natural environment, the material has been altered by deliberate human intervention to a composition and/or placed at a locus in a cell other than the locus native to the material. Methods for isolation of promoter regions are well known in the art.

"Functional variants" of the regulatory sequences are also encompassed by the compositions of the present invention. Functional variants include, for example, the native regulatory sequences of the invention having one or more nucleotide substitutions, deletions or insertions. Functional variants of the invention may be created by site-directed mutagenesis, induced mutation, or may occur as allelic variants (polymorphisms).

As used herein, a "functional fragment" of the regulatory sequence is a nucleotide sequence that is a regulatory sequence variant formed by one or more deletions from a larger sequence. For example, the 5' portion of a promoter up to the TATA box near the transcription start site can be deleted without abolishing promoter activity, as described by Opsahl-Sorteberg, H-G. et al., "Identification of a 49-bp fragment of the HvLTP2 promoter directing aleruone cell specific expression" *Gene* 341:49-58 (2004). Such variants should retain promoter activity, particularly the ability to drive expression in male tissues. Activity can be measured by Northern blot analysis, reporter activity measurements when using transcriptional fusions, and the like. See, for example, Sambrook et al. (1989) *Molecular Cloning: A Laboratory Manual* (2nd ed. Cold Spring Harbor Laboratory, Cold Spring Harbor, N.Y.), herein incorporated by reference.

Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology See particularly, Mullis et al. (1987) Methods Enzymol. 155:335-350, and Erlich, ed. (1989) *PCR Technology* (Stockton Press, New York).

Sequences which hybridize to the regulatory sequences of the present invention are within the scope of the invention. Sequences that correspond to the promoter sequences of the present invention and hybridize to the promoter sequences disclosed herein will be at least 50% homologous, 70% homologous, and even 85% 86%, 87%, 88%, 89%, 90%, 91%, 92%, 93%, 94%, 95%, 96%, 97%, 98%, 99% homologous or more with the disclosed sequence.

Smaller fragments may yet contain the regulatory properties of the promoter so identified and deletion analysis is one method of identifying essential regions. Deletion analysis can occur from both the 5' and 3' ends of the regulatory region. Fragments can be obtained by site-directed mutagenesis, mutagenesis using the polymerase chain reaction and the like. (See, *Directed Mutagenesis: A Practical Approach* IRL Press (1991)). The 3' deletions can delineate the essential region and identify the 3' end so that this region may then be operably linked to a core promoter of choice. Once the essential region is identified, transcription of an exogenous gene may be controlled by the essential region plus a core promoter. By core promoter is meant the sequence called the TATA box which is common to promoters in all genes encoding proteins. Thus the upstream promoter of Msca1 can optionally be used in conjunction with its own or core promoters from other sources. The promoter may be native or non-native to the cell in which it is found.

The core promoter can be any one of known core promoters such as the Cauliflower Mosaic Virus 35S or 19S promoter (U.S. Pat. No. 5,352,605), ubiquitin promoter (U.S. Pat. No. 5,510,474) the IN2 core promoter (U.S. Pat. No. 5,364,780) or a Figwort Mosaic Virus promoter (Gruber, et al. "Vectors for Plant Transformation" *Methods in Plant Molecular Biology and Biotechnology*) et al. eds, CRC Press pp. 89-119 (1993)).

Promoter sequences from other plants may be isolated according to well-known techniques based on their sequence homology to the promoter sequence set forth herein. In these techniques, all or part of the known promoter sequence is used as a probe which selectively hybridizes to other sequences present in a population of cloned genomic DNA fragments (i.e. genomic libraries) from a chosen organism. Methods are readily available in the art for the hybridization of nucleic acid sequences.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see e.g. Innis et al., eds., (1990) *PCR Protocols, A Guide to Methods and Applications*, Academic Press).

Further, a promoter of the present invention can be linked with nucleotide sequences other than the Msca1 gene to express other heterologous nucleotide sequences. The nucleotide sequence for the promoter of the invention, as well as fragments and variants thereof, can be provided in expression cassettes along with heterologous nucleotide sequences for expression in the plant of interest, more particularly in the male tissue of the plant. Such an expression cassette is provided with a plurality of restriction sites for insertion of the nucleotide sequence to be under the transcriptional regulation of the promoter. These expression cassettes are useful in the genetic manipulation of any plant to achieve a desired phenotypic response.

Examples of other nucleotide sequences which can be used as the exogenous gene of the expression vector with the Msca1 promoter, or other promoters taught herein or known to those of skill in the art include complementary nucleotidic units such as antisense molecules (callase antisense RNA, bamase antisense RNA and chalcone synthase antisense RNA, Ms45 antisense RNA), ribozymes and external guide sequences, an aptamer or single stranded nucleotides. The exogenous nucleotide sequence can also encode carbohydrate degrading or modifying enzymes, amylases, debranching enzymes and pectinases, such as the alpha amylase gene, auxins, rol B, cytotoxins, diptheria toxin, DAM methylase, avidin, or may be selected from a prokaryotic regulatory system. By way of example, Mariani, et al., *Nature Vol.* 347;

pp. 737; (1990), have shown that expression in the tapetum of either *Aspergillus oryzae* RNase-T1 or an RNase of *Bacillus amyloliquefaciens*, designated "barnase," induced destruction of the tapetal cells, resulting in male infertility. Quaas, et al., *Eur. J. Biochem. Vol.* 173: pp. 617 (1988), describe the chemical synthesis of the RNase-T1, while the nucleotide sequence of the barnase gene is disclosed in Hartley, *J. Molec. Biol.*; Vol. 202: pp. 913 (1988). The rolB gene of *Agrobacterium rhizogenes* codes for an enzyme that interferes with auxin metabolism by catalyzing the release of free indoles from indoxyl-β-glucosides. Estruch, et al., *EMBO J. Vol.* 11: pp. 3125 (1991) and Spena, et al., *Theor. Appl. Genet.*; Vol. 84: pp. 520 (1992), have shown that the anther-specific expression of the rolB gene in tobacco resulted in plants having shriveled anthers in which pollen production was severely decreased and the rolB gene is an example of a gene that is useful for the control of pollen production. Slightom, et al., *J. Biol. Chem. Vol.* 261: pp. 108 (1985), disclose the nucleotide sequence of the rolB gene. DNA molecules encoding the diphtheria toxin gene can be obtained from the American Type Culture Collection (Rockville, Md.), ATCC No. 39359 or ATCC No. 67011 and see Fabijanski, et al., E.P. Appl. No. 90902754.2, "Molecular Methods of Hybrid Seed Production" for examples and methods of use. The DAM methylase gene is used to cause sterility in the methods discussed at U.S. Pat. No. 5,689,049 and PCT/US95/15229 Cigan, A. M. and Albertsen, M. C., "Reversible Nuclear Genetic System for Male Sterility in Transgenic Plants." Also see discussion of use of the avidin gene to cause sterility at U.S. Pat. No. 5,962,769 "Induction of Male Sterility in Plants by Expression of High Levels of Avidin" by Albertsen et al.

The invention includes vectors with the Msca1 gene and/or its promoter. A vector is prepared comprising Msca1, a promoter that will drive expression of the gene in the plant and a terminator region. As noted, the promoter in the construct may be the native promoter or a substituted promoter which will provide expression in the plant. The promoter in the construct may be an inducible promoter, so that expression of the sense or antisense molecule in the construct can be controlled by exposure to the inducer. In this regard, a plant-compatible promoter element can be employed in the construct, influenced by the end result desired. When linking the Msca1 nucleotide sequence with another promoter, it will be preferable that the promoter drive expression of the sequence sufficiently early in plant development that the Msca1 sequence or fragment or variant is expressed after primordial initiation but before division of archesporial cells. Examples of the variety of promoters that could be used include the constitutive viral promoters such as the cauliflower mosaic virus (CaMV) 19S and 35S promoters or the figwort mosaic virus 35S promoter. See Kay et al., (1987) *Science* 236:1299 and European patent application No. 0 342 926; and the ubiquitin promoter (see for example U.S. Pat. No. 5,510,474) or any other ubiquitin-like promoter, which encodes a ubiquitin protein, but may have varying particular sequences (for example U.S. Pat. Nos. 5,614,399 and 6,054,574).

It will be evident to one skilled in the art that the construct can also contain one of the variety of other promoters available, depending upon the particular application. For example, the promoter may be linked with a selectable marker, or a gene of interest for expression in the plant cell. In this regard, any plant-compatible promoter can be employed. Those can be the 35S and ubiquitin-like promoters as referred to above, or any other plant gene promoters, such as, for example, the promoter for the small subunit of ribulose-1,5-bis-phosphate carboxylase, or promoters from the tumor-inducing plasmids from *Agrobacterium tumefaciens*, such as the nopaline synthase and octopine synthase promoters; the barley lipid transfer protein promoter, LTP2 (Kalla et al., *Plant J.* (1994) 6(6): 849-60); the END2 promoter (Linnestad et al. U.S. Pat. No. 6,903,205); and the polygalacturonase PG47 promoter (See Allen and Lonsdale, *Plant J.* (1993) 3:261-271; WO 94/01572; U.S. Pat. No. 5,412,085 See international application WO 91/19806 for a review of illustrative plant promoters suitably employed in the present invention.

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods. Any inducible promoter can be used in the instant invention. See Ward et al. *Plant Mol. Biol.* 22: 361-366 (1993). Exemplary inducible promoters include ecdysone receptor promoters, U.S. Pat. No. 6,504,082; promoters from the ACE1 system which responds to copper (Mett et al. PNAS 90: 4567-4571 (1993)); In2-1 and In2-2 gene from maize which respond to benzenesulfonamide herbicide safeners (U.S. Pat. No. 5,364,780; Hershey et al., *Mol. Gen. Genetics* 227: 229-237 (1991) and Gatz et al., *Mol. Gen. Genetics* 243: 32-38 (1994)); the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2): 247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789, 156).

Tissue-preferred promoters can be utilized to target enhanced transcription and/or expression within a particular plant tissue. Promoters may express in the tissue of interest, along with expression in other plant tissue, may express strongly in the tissue of interest and to a much lesser degree than other tissue, or may express highly preferably in the tissue of interest. Tissue-preferred promoters include those described in Yamamoto et al. (1997) *Plant J.* 12(2): 255-265; Kawamata et al. (1997) *Plant Cell Physiol.* 38(7): 792-803; Hansen et al. (1997) *Mol. Gen. Genet.* 254(3):337-343; Russell et al. (1997) *Transgenic Res.* 6(2): 157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20: 181-196; Orozco et al. (1993) *Plant Mol Biol.* 23(6): 1129-1138; Matsuoka et al. (1993) *Proc Natl. Acad. Sci. USA* 90(20): 9586-9590; and Guevara-Garcia et al. (1993) *Plant J.* 4(3): 495-505. In one embodiment, the promoters are those which preferentially express to the male or female tissue of the plant. The invention does not require that any particular male tissue-preferred promoter be used in the process, and any of the many such promoters known to one skilled in the art may be employed. The native Msca1 promoter described herein is one example of a useful promoter. Another such promoter is the 5126 promoter, which preferentially directs expression of the gene to which it is linked to male tissue of the plants, as described in U.S. Pat. Nos. 5,837,851 and 5,689,051. Other examples include the Ms45 promoter described at U.S. Pat. No. 6,037,523; Ms26 promoter described at US Publication No. 20060015968; SF3 promoter described at U.S. Pat. No. 6,452,069; the BS92-7 promoter described at WO 02/063021; a SGB6 regulatory element described at U.S. Pat. No. 5,470,359; the TA29 promoter (Koltunow et al. (1990) "Different temporal and spatial gene expression patterns occur during anther development." *Plant Cell* 2:1201-1224; Goldberg, R. B., Beals, T. P. and Sanders, P. M., (1993) "Anther development: basic principles and practical applications" *Plant Cell* 5:1217-1229; and U.S. Pat. No. 6,399,856); the type 2 metallothionein-like gene promoter (Charbonnel-Campaa et al., *Gene* (2000) 254:199-208); and the *Brassica* Bca9 promoter (Lee et al., *Plant Cell Rep.* (2003) 22:268-273).

Certain constructs may also include a gamete tissue preferred promoter, depending upon the various components and the applications in which it is employed. Male gamete preferred promoters include the PG47 promoter, supra as well as ZM13 promoter (Hamilton et al., *Plant Mol. Biol.* (1998) 38:663-669); actin depolymerizing factor promoters (such as Zmabp1, Zmabp2; see for example Lopez et al. *Proc. Natl. Acad. Sci.* USA (1996) 93: 7415-7420); the promoter of the maize petctin methylesterase-liked gene, ZmC5 (Wakeley et al. *Plant Mol. Biol.* (1998) 37:187-192); the profilin gene promoter Zmpro1 (Kovar et al., *The Plant Cell* (2000) 12:583-598); the sulphated pentapeptide phytosulphokine gene ZmPSK1 (Lorbiecke et al., *Journal of Experimental Botany* (2005) 56(417): 1805-1819); the promoter of the calmodulin binding protein Mpcbp (Reddy et al. *J. Biol. Chem.* (2000) 275(45):35457-70).

Other components of the vector may be included, also depending upon intended use of the gene. Examples include selectable markers, targeting or regulatory sequences, stabilizing or leader sequences, introns etc. General descriptions and examples of plant expression vectors and reporter genes can be found in Gruber, et al., "Vectors for Plant Transformation" in *Method in Plant Molecular Biology and Biotechnology*, Glick et al eds; CRC Press pp. 89-119 (1993). The selection of an appropriate expression vector will depend upon the host and the method of introducing the expression vector into the host. The expression cassette will also include at the 3' terminus of the heterologous nucleotide sequence of interest, a transcriptional and translational termination region functional in plants. The termination region can be native with the promoter nucleotide sequence of the present invention, can be native with the DNA sequence of interest, or can be derived from another source. Convenient termination regions are available from the Ti-plasmid of *A. tumefaciens*, such as the octopine synthase and nopaline synthase termination regions. See also, Guerineau et al. *Mol. Gen. Genet.* 262:141-144 (1991); Proudfoot, *Cell* 64:671-674 (1991); Sanfacon et al. *Genes Dev.* 5:141-149 (1991); Mogen et al. *Plant Cell* 2:1261-1272 (1990); Munroe et al. *Gene* 91:151-158 (1990); Ballas et al. *Nucleic Acids Res.* 17:7891-7903 (1989); Joshi et al. *Nucleic Acid Res.* 15:9627-9639 (1987).

The expression cassettes can additionally contain 5' leader sequences. Such leader sequences can act to enhance translation. Translation leaders are known in the art and include by way of example, picornavirus leaders, EMCV leader (Encephalomyocarditis 5' noncoding region), Elroy-Stein et al. *Proc. Nat. Acad. Sci. USA* 86:6126-6130 (1989); potyvirus leaders, for example, TEV leader (Tobacco Etch Virus), Allison et al.; MDMV leader (Maize Dwarf Mosaic Virus), *Virology* 154:9-20 (1986); human immunoglobulin heavy-chain binding protein (BiP), Macejak et al. *Nature* 353:90-94 (1991); untranslated leader from the coat protein mRNA of alfalfa mosaic virus (AMV RNA 4), Jobling et al. *Nature* 325:622-625 (1987); Tobacco mosaic virus leader (TMV), Gallie et al. (1989) Molecular Biology of RNA, pages 237-256; and maize chlorotic mottle virus leader (MCMV) Lommel et al. *Virology* 81:382-385 (1991). See also Della-Cioppa et al. *Plant Physiology* 84:965-968 (1987). The cassette can also contain sequences that enhance translation and/or mRNA stability such as introns.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, *Zea mays* Brittle-1 chloroplast transit peptide (Nelson et al. *Plant physiol* 117(4):1235-1252 (1998); Sullivan et al. *Plant Cell* 3(12):1337-48; Sullivan et al., *Planta* (1995) 196(3): 477-84; Sullivan et al., *J. Biol. Chem.* (1992) 267(26):18999-9004) and the like. One skilled in the art will readily appreciate the many options available in expressing a product to a particular organelle. For example, the barley alpha amylase sequence is often used to direct expression to the endoplasmic reticulum (Rogers, *J. Biol. Chem.* 260:3731-3738 (1985)). Use of transit peptides is well known (e.g., see U.S. Pat. Nos. 5,717,084; 5,728,925).

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions, such as transitions and transversions, can be involved.

As noted herein, the present invention provides vectors capable of expressing genes of interest. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra).

The transformation vector comprising the promoter sequence of the present invention, or another promoter operably linked to a heterologous nucleotide sequence in an expression cassette and/or the nucleotide sequence of the present invention, can also contain at least one additional nucleotide sequence for a gene to be cotransformed into the organism. Alternatively, the additional sequence(s) can be provided on another transformation vector.

Reporter genes can be included in the transformation vectors. Examples of suitable reporter genes known in the art can be found in, for example, Jefferson et al. (1991) in *Plant Molecular Biology Manual*, ed. Gelvin et al. (Kluwer Academic Publishers), pp. 1-33; DeWet et al. *Mol. Cell. Biol.* 7:725-737 (1987); Goff et al. *EMBO J.* 9:2517-2522 (1990);

Kain et al. *BioTechniques* 19:650-655 (1995); and Chiu et al. *Current Biology* 6:325-330 (1996).

Selectable reporter genes for selection of transformed cells or tissues can be included in the transformation vectors. These can include genes that confer antibiotic resistance or resistance to herbicides. Examples of suitable selectable marker genes include, but are not limited to, genes encoding resistance to chloramphenicol, Herrera Estrella et al. *EMBO J.* 2:987-992(1983); methotrexate, Herrera Estrella et al. *Nature* 303:209-213(1983); Meijer et al. *Plant Mol. Biol.* 16:807-820 (1991); hygromycin, Waldron et al. *Plant Mol. Biol.* 5:103-108 (1985), Zhijian et al. *Plant Science* 108:219-227 (1995); streptomycin, Jones et al. *Mol. Gen. Genet.* 210:86-91(1987); spectinomycin, Bretagne-Sagnard et al. *Transgenic Res.* 5:131-137 (1996); bleomycin, Hille et al. *Plant Mol. Biol.* 7:171-176 (1990); sulfonamide, Guerineau et al. *Plant Mol. Biol.* 15:127-136(1990); bromoxynil, Stalker et al. *Science* 242:419-423 (1988); glyphosate, Shaw et al. *Science* 233:478-481(1986); and phosphinothricin, DeBlock et al. *EMBO J.* 6:2513-2518 (1987).

Scorable or screenable markers may also be employed, where presence of the sequence produces a measurable product. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. *The EMBO Journal* vol. 6 No. 13 pp. 3901-3907); and alkaline phosphatase. Other screenable markers include the anthocyanin/flavonoid genes in general (See discussion at Taylor and Briggs, *The Plant Cell* (1990) 2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., *Plant Cell* (1996) δ: 1171-1179; Scheffler et al. *Mol. Gen. Genet.* (1994) 242:40-48) and maize C2 (Wienand et al., *Mol. Gen. Genet.* (1986) 203:202-207); the B gene (Chandler et al., *Plant Cell* (1989) 1:1175-1183), the p1 gene (Grotewold et al, *Proc. Natl. Acad. Sci. USA* (1991) 88:4587-4591; Grotewold et al., *Cell* (1994) 76:543-553; Sidorenko et al., *Plant Mol. Biol.* (1999)39:11-19); the bronze locus genes (Ralston et al., *Genetics* (1988) 119:185-197; Nash et al., *Plant Cell* (1990) 2(11): 1039-1049), among others. Yet further examples of suitable markers include the cyan fluorescent protein (CYP) gene (Bolte et al. (2004) *J. Cell Science* 117: 943-54 and Kato et al. (2002) *Plant Physiol* 129: 913-42), the yellow fluorescent protein gene (PhiYFP™ from Evrogen; see Bolte et al. (2004) *J. Cell Science* 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) *EMBO J.* 8:343); a green fluorescent protein (GFP) gene (Sheen et al., *Plant J.* (1995) 8(5):777-84); and DsRed2 where plant cells transformed with the marker gene are red in color, and thus visually selectable (Dietrich et al. (2002) *Biotechniques* 2(2): 286-293). Additional examples include a p-lactamase gene (Sutcliffe, *Proc. Nat'l. Acad. Sci. U.S.A.* (1978) 75:3737), which encodes an enzyme for which various chromogenic substrates are known (e.g., PADAC, a chromogenic cephalosporin); a xylE gene (Zukowsky et al., *Proc. Nat'l. Acad. Sci. U.S.A.* (1983) 80:1101), which encodes a catechol dioxygenase that can convert chromogenic catechols; an α-amylase gene (Ikuta et al., *Biotech.* (1990) 8:241); and a tyrosinase gene (Katz et al., *J. Gen. Microbiol.* (1983) 129:2703), which encodes an enzyme capable of oxidizing tyrosine to DOPA and dopaquinone, which in turn condenses to form the easily detectable compound melanin. Clearly, many such markers are available to one skilled in the art.

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription or transcript and translation of the sequence to effect phenotypic changes in the organism. Thus, any method which provides for efficient transformation/transfection may be employed.

Methods for introducing expression vectors into plant tissue available to one skilled in the art are varied and will depend on the plant selected. Procedures for transforming a wide variety of plant species are well known and described throughout the literature. See, for example, Miki et al, "Procedures for Introducing Foreign DNA into Plants" in *Methods in Plant Molecular Biotechnology*, supra; Klein et al, *Bio/Technology* 10:268 (1992); and Weising et al., *Ann. Rev. Genet.* 22: 421-477 (1988). For example, the DNA construct may be introduced into the genomic DNA of the plant cell using techniques such as microprojectile-mediated delivery, Klein et al., *Nature* 327: 70-73 (1987); electroporation, Fromm et al., *Proc. Natl. Acad. Sci.* 82: 5824 (1985); polyethylene glycol (PEG) precipitation, Paszkowski et al., *EMBO J.* 3: 2717-2722 (1984); direct gene transfer WO 85/01856 and EP No. 0 275 069; in vitro protoplast transformation, U.S. Pat. No. 4,684,611; and microinjection of plant cell protoplasts or embryogenic callus, Crossway, *Mol. Gen. Genetics* 202:179-185 (1985). Co-cultivation of plant tissue with *Agrobacterium tumefaciens* is another option, where the DNA constructs are placed into a binary vector system. See e.g., U.S. Pat. No. 5,591,616; Ishida et al., "High Efficiency Transformation of Maize (*Zea mays* L.) mediated by *Agrobacterium tumefaciens*" *Nature Biotechnology* 14:745-750 (1996). The virulence functions of the *Agrobacterium tumefaciens* host will direct the insertion of the construct into the plant cell DNA when the cell is infected by the bacteria. See, for example Horsch et al., *Science* 233: 496-498 (1984), and Fraley et al., *Proc. Natl. Acad. Sci.* 80: 4803 (1983).

Standard methods for transformation of canola are described at Moloney et al. "High Efficiency Transformation of *Brassica napus* using *Agrobacterium* Vectors" *Plant Cell Reports* 8:238-242 (1989). Corn transformation is described by Fromm et al, *Bio/Technology* 8:833 (1990) and Gordon-Kamm et al, supra. *Agrobacterium* is primarily used in dicots, but certain monocots such as maize can be transformed by *Agrobacterium*. See supra and U.S. Pat. No. 5,550,318. Rice transformation is described by Hiei et al., "Efficient Transformation of Rice (*Oryza sativs* L.) Mediated by *Agrobacterium* and Sequence Analysis of the Boundaries of the T-DNA" *The Plant Journal* 6(2): 271-282 (1994, Christou et al, *Trends in Biotechnology* 10:239 (1992) and Lee et al, *Proc. Nat'l Acad. Sci. USA* 88:6389 (1991). Wheat can be transformed by techniques similar to those used for transforming corn or rice. *Sorghum* transformation is described at Casas et al, supra and sorghum by Wan et al, *Plant Physicol.* 104:37 (1994). Soybean transformation is described in a number of publications, including U.S. Pat. No. 5,015,580.

When referring to "introduction" of the nucleotide sequence into a plant, it is meant that this can occur by direct transformation methods, such as *Agrobacterium* transformation of plant tissue, microprojectile bombardment, electroporation, or any one of many methods known to one skilled in the art; or, it can occur by crossing a plant having the heterologous nucleotide sequence with another plant so that progeny have the nucleotide sequence incorporated into their genomes. Such breeding techniques are well known to one skilled in the art.

The plant breeding methods used herein are well known to one skilled in the art. For a discussion of plant breeding techniques, see Poehlman (1987) *Breeding Field Crops*. AVI Publication Co., Westport Conn. Many of the plants which would be most preferred in this method are bred through techniques that take advantage of the plant's method of pollination.

Backcrossing methods may be used to introduce a gene into the plants. This technique has been used for decades to introduce traits into a plant. An example of a description of this and other plant breeding methodologies that are well known can be found in references such as *Plant Breeding Methodology*, edit. Neal Jensen, John Wiley & Sons, Inc. (1988). In a typical backcross protocol, the original variety of interest (recurrent parent) is crossed to a second variety (non-recurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

In certain embodiments of the invention, it is desirable to maintain the male sterile homozygous recessive condition of a male sterile plant, when using a transgenic restoration approach, while decreasing the number of plants, plantings and steps needed for maintenance of a plant with such traits. Homozygosity is a genetic condition existing when identical alleles reside at corresponding loci on homologous chromosomes. Heterozygosity is a genetic condition existing when different alleles reside at corresponding loci on homologous chromosomes. Hemizygosity is a genetic condition existing when there is only one copy of a gene (or set of genes) with no allelic counterpart on the sister chromosome. In an embodiment, the homozygous recessive condition results in conferring on the plant a trait of interest, which can be any trait desired and which results from the recessive genotype, such as increased drought or cold tolerance, early maturity, changed oil or protein content, or any of a multitude of the many traits of interest to plant breeders. In one embodiment, the homozygous recessive condition confers male sterility upon the plant. When the sequence which is the functional complement of the homozygous condition is introduced into the plant (that is, a sequence which, when introduced into and expressed in the plant having the homozygous recessive condition, restores the wild-type condition), fertility is restored by virtue of restoration of the wild-type fertile phenotype.

Maintenance of the homozygous recessive condition is achieved by introducing into a plant restoration transgene construct into a plant that is linked to a sequence which interferes with the function or formation of male gametes of the plant to create a maintainer or donor plant. The restoring transgene, upon introduction into a plant that is homozygous recessive for the genetic trait, restores the genetic function of that trait, with the plant producing only viable pollen containing a copy of the recessive allele but not containing the restoration transgene. The transgene is kept in the hemizygous state in the maintainer plant. By transgene, it is meant any nucleic acid sequence which is introduced into the genome of a cell by genetic engineering techniques. A transgene may be a native DNA sequence, or a heterologous DNA sequence (i.e., "foreign DNA"). The term native DNA sequence refers to a nucleotide sequence which is naturally found in the cell but that may have been modified from its original form. The pollen from the maintainer can be used to fertilize plants that are homozygous for the recessive trait, and the progeny will therefore retain their homozygous recessive condition. The maintainer plant containing the restoring transgene construct is propagated by self-fertilization, with the resulting seed used to produce further plants that are homozygous recessive plants and contain the restoring transgene construct.

The maintainer plant serves as a pollen donor to the plant having the homozygous recessive trait. The maintainer is optimally produced from a plant having the homozygous recessive trait and which also has nucleotide sequences introduced therein which would restore the trait created by the homozygous recessive alleles. Further, the restoration sequence is linked to nucleotide sequences which interfere with the function or formation of male gametes. The gene can operate to prevent formation of male gametes or prevent function of the male gametes by any of a variety of well-know modalities and is not limited to a particular methodology. By way of example but not limitation, this can include use of genes which express a product cytotoxic to male gametes (See for example, U.S. Pat. No. 5,792,853; U.S. Pat. No. 5,689,049; PCT/EP89/00495); inhibit product formation of another gene important to male gamete function or formation (See, U.S. Pat. Nos. 5,859,341; 6,297,426); combine with another gene product to produce a substance preventing gene formation or function (See U.S. Pat. Nos. 6,162,964; 6,013,859; 6,281,348; 6,399,856; 6,248,935; 6,750,868; 5,792,853); are antisense to or cause co-suppression of a gene critical to male gamete function or formation (See U.S. Pat. Nos. 6,184,439; 5,728,926; 6,191,343; 5,728,558; 5,741,684); interfere with expression through use of hairpin formations (Smith et al. (2000) *Nature* 407:319-320; WO 99/53050 and WO 98/53083) or the like. Many nucleotide sequences are known which inhibit pollen formation or function and any sequences which accomplish this function will suffice. A discussion of genes which can impact proper development or function is included at U.S. Pat. No. 6,399,856 and includes genes with inhibitory effects such as cytotoxin genes, methylase genes, and growth-inhibiting genes. Example of such genes include, but are not limited to diphtheria toxin A-chain gene (Czako, M. and An, G. (1991) "Expression of DNA coding for Diptheria toxin Chain A is toxic to plant cells" *Plant Physiol.* 95 687-692. and Greenfield et al *PNAS* 80:6853 (1983), Palmiter et al *Cell* 50:435 (1987)); cell cycle division mutants such as CDC in maize (Colasanti, J., Tyers, M. and Sundaresan, V., "Isolation and Characterization of cDNA clones encoding a functional P34 cdc2 homologue from *Zea mays*" PNAS 88, 3377-3381 (1991)); the WT gene (Farmer, A. A., Loftus, T. M., Mills, A. A., Sato, K. V., Neill, J., Yang, M., Tron, T., Trumpower, B. L. and Stanbridge, E. G. *Hum. Mol. Genet.* 3, 723-728 (1994)); and P68 (Chen, J. J., Pal, J. K., Petryshyn, R., Kuo, I., Yang, J. M., Throop, M. S., Gehrke, L. and London, I. M. "Eukaryotic translation initiation kinases" *PNAS* 88, 315-319 (1991)).

Further examples of so-called "cytotoxic" genes are discussed supra and can include, but are not limited to pectate lyase gene pelE, from *Erwinia chrysanthermi* (Kenn et al *J. Bacteroil* 168:595 (1986)); T-urf13 gene from cms-T maize mitochondrial genomes (Braun et al *Plant Cell* 2:153 (1990); Dewey et al. *PNAS* 84:5374 (1987)); CytA toxin gene from *Bacillus thuringiensis Israeliensis* that causes cell membrane disruption (McLean et al *J. Bacteriol* 169:1017 (1987), U.S. Pat. No. 4,918,006); DNAses, RNAses, (U.S. Pat. No. 5,633, 441); proteases, or a genes expressing anti-sense RNA. A suitable gene may also encode a protein involved in inhibiting pistil development, pollen stigma interactions, pollen tube growth or fertilization, or a combination thereof. In addition genes that either interfere with the normal accumulation of starch in pollen or affect osmotic balance within pollen may also be suitable.

In an illustrative embodiment, the DAM-methylase gene is used, discussed supra and at U.S. Pat. Nos. 5,792,852 and 5,689,049, the expression product of which catalyzes methylation of adenine residues in the DNA of the plant. Methylated adenines will affect cell viability and will be found only in the tissues in which the DAM-methylase gene is expressed. In another embodiment, an α-amylase gene can be used with a male tissue-preferred promoter. During the initial germinating period of cereal seeds, the aleurone layer cells will synthesize α-amylase, which participates in hydrolyzing starch to form glucose and maltose, so as to provide the nutrients needed for the growth of the germ (J. C. Rogers and C. Milliman, *J. Biol. Chem.*, 259 (19): 12234-12240, 1984; Rogers, J. C., *J. Biol. Chem.*, 260: 3731-3738, 1985). In an embodiment, the α-amylase gene used can be the *Zea mays* α-amylase-1 gene. Young et al. "Cloning of an α-amylase cDNA from aleurone tissue of germinating maize seed" *Plant Physiol.* 105(2) 759-760 and GenBank accession No. L25805, GI:426481). Sequences encoding α-amylase are not typically found in pollen cells, and when expression is directed to male tissue, the result is a breakdown of the energy source for the pollen grains, and repression of pollen development.

One skilled in this area readily appreciates the methods described herein are applicable to any other crops which have the potential to outcross. By way of example, but not limitation it can include maize, soybean, sorghum, or any plant with the capacity to outcross.

Ordinarily, to produce more plants having the recessive condition, one might cross the recessive plant with another recessive plant. This may not be desirable for some recessive traits and may be impossible for recessive traits affecting reproductive development. Alternatively, one could cross the homozygous plant with a second plant having the restoration gene, but this requires further crossing to segregate away the restoring gene to once again reach the recessive phenotypic state. Instead, in one process the homozygous recessive condition can be maintained, while crossing it with the maintainer plant. This method can be used with any situation in which is it desired to continue the recessive condition. This results in a cost-effective system that is relatively easy to operate to maintain a population of homozygous recessive plants.

A sporophytic gene is one which operates independently of the gametes. When the homozygous recessive condition is one which produces male sterility by preventing male sporophyte development, the maintainer plant, of necessity, must contain a functional restoring transgene construct capable of complementing the mutation and rendering the homozygous recessive plant able to produce viable pollen. Linking this sporophytic restoration gene with a second functional nucleotide sequence which interferes with the function or formation of the male gametes of the plant results in a maintainer plant that produces viable pollen that only contains the recessive allele of the sporophytic gene at its native locus due to the action of the second nucleotide sequence in interfering with pollen formation or function. This viable pollen fraction is non-transgenic with regard to the restoring transgene construct.

In a still further embodiment, a marker gene, as discussed supra, may be provided in the construct with the restoring transgene. By way of example without limitation, use of a herbicide resistant marker, such as bar allows one to eliminate cells not having the restoring transgene. In yet another example, when using a scorable marker, such as the Ds Red2 fluorescent protein, any inadvertent transmission of the transgene can also be detected visually, and such escapes eliminated from progeny. Clearly, many other variations in the restoring construct are available to one skilled in the art.

In an illustrative embodiment, a method of maintaining a homozygous recessive condition of a male sterile plant at a genetic locus is provided, in which is employed a first nucleotide sequence which is a gene critical to male fertility, a second nucleotide sequence which inhibits the function or formation of viable male gametes, an optional third nucleotide sequence which is operably linked to the first sequence and preferentially expresses the sequence in male plant cells, an optional fourth nucleotide sequence operably linked to a fourth nucleotide sequence, the fourth sequence directing expression to male gametes, and an optional fifth nucleotide sequence which is a selectable or scorable marker allowing for selection of plant cells.

For example, it is desirable to produce male sterile female plants for use in the hybrid production process which are sterile as a result of being homozygous for a mutation in the Ms45 gene; a gene which is critical to male fertility. Such a mutant Ms45 allele is designated as ms45 and a plant that is homozygous for ms45 (represented by the notation ms45/ms45) displays the homozygous recessive male sterility phenotype and produces no functional pollen. See, U.S. Pat. Nos. 5,478,369; 5,850,014; 6,265,640; and 5,824,524. In both the inbred and hybrid production processes, it is maintaining this homozygous recessive condition is important. When sequences encoding the Ms45 gene are introduced into a plant that is homozygous recessive for ms45, male fertility results. By the method of the invention, a plant which is ms45/ms45 homozygous recessive may have introduced into it a functional sporophytic Ms45 gene, and thus is male fertile. This gene can be linked to a gene which operates to render pollen containing the restoring transgene construct nonfunctional or prevents its formation, or which produces a lethal product in pollen, linked to the promoter directing its expression to the male gametes to produce a plant that only produced pollen containing ms45 without the restoring transgene construct.

An example is a construct which includes the Ms45 gene, linked with a 5126 promoter, a male tissue-preferred promoter (See U.S. Pat. Nos. 5,750,868; 5,837,851; and 5,689,051) and further linked to the cytotoxic DAM methylase gene under control of the polygalacturonase promoter, PG47 promoter (See U.S. Pat. Nos. 5,792,853; 5,689,049) in a hemizygotic condition. Therefore the resulting plant produces pollen, but the only viable pollen results from the allele not containing the restoring Ms45/DAM methylase construct and thus contains only the ms45 gene. It can therefore be used as a pollinator to fertilize the homozygous recessive plant (ms45/ms45), and progeny produced will continue to be male sterile as a result of maintaining homozygosity for ms45. The progeny will also not contain the introduced restoring transgene construct.

In yet another restoring construct example, the Msca1 gene is linked with a Msca1 promoter, and further linked to the *Zea mays* α-amylase gene under control of the male tissue-preferred PG47 promoter. The scorable marker used in an embodiment is DS-RED2.

A desirable result of the process of the invention is that the plant having the restorer nucleotide sequence may be self-fertilized, that is pollen from the plant transferred to the flower of the same plant to achieve the propagation of restorer plants. (Note that in referring to "self fertilization", it includes the situation where the plant producing the pollen is fertilized with that same plant's pollen, and the situation where two or more identical inbred plants are planted together and pollen from the identical inbred plant pollinate a separate but identical inbred plant). The restoring transgene construct will not be present in the pollen cells but it will be contained in 50% of the ovules (the female gamete). The seed resulting from the self-fertilization can be planted, and selection made for the seed having the restoring transgene construct. The selection process can occur by any one of many known processes; the most common where the restoration nucleotide sequence is linked to a marker gene. The marker can be scorable or selectable, and allows those plants produced from the seed having the restoration gene to be identified.

In an embodiment of the invention, it is possible to provide that the male gamete-tissue preferred promoter is inducible. Additional control is thus allowed in the process, where so desired, by providing that the plant having the restoration nucleotide sequences is constitutively male sterile. This type of male sterility is set forth the in U.S. Pat. No. 5,859,341. In order for the plant to become fertile, the inducing substance must be provided, and the plant will become fertile. Again, when combined with the process of the invention as described supra, the only pollen produced will not contain the restoration nucleotide sequences.

Further detailed description is provided below by way of instruction and illustration and is not intended to limit the scope of the invention.

EXAMPLE 1

Cloning and Sequencing of the Msca1 Gene

Following mapping of the msca1 mutation to the short arm of chromosome 7, a map-based cloning approach was undertaken to clone the msca1 gene. The process of genomic library screenings is commonly known among those skilled in the art and is described at Sambrook, J., Fritsch, E. F., Maniatis T., et al., *Molecular Cloning: A Laboratory Manual*, Cold Spring Harbor Laboratory, Cold Spring Harbor Lab Press, Plainview, N.Y. (1989). A large mapping population was developed using the msca1-ref allele (West, D P and Albertsen, M C. Three new male-sterile genes 1985. *MNL* 59:87). Markers were used to saturate map this population and an interval (155 KB) was defined by markers pco144723 and b49p15.f that spanned 2 BAC (Bacterial Artificial Chromosome) clones. Sequencing and additional marker development from the BACs narrowed the interval to 9 Kb. Sequence of this region revealed only one open reading frame, coding for a putative plant-specific glutaredoxin gene. The nucleotide sequence is shown in FIG. 2 (SEQ ID NO: 1) and the protein sequence is shown in FIG. 3 (SEQ ID NO: 2). Other glutaredoxin family members have previously been shown to have a role in plant development (Shuping Xing, Mario G. Rosso and Sabine Zachgo. ROXY1, a member of the plant glutaredoxin family, is required for petal development in *Arabidopsis thaliana* (2005) *Development* 132, 1555-1565). Glutaredoxin genes are ubiquitous small heat-stable oxidoreductases that are believed to function in a wide range of cellular processes from DNA synthesis to protein folding, redox regulation of transcription and translation, and cellular signaling, among others. In a BLAST comparison of the Msca1 gene, the sequences with highest similarity were regions that had 77% identity to a glutaredoxin-like protein. GenBank access No. XP_476652.

Southern analysis of the msca1 reference allele indicated that the glutaredoxin gene was deleted. Sequencing of the reference allele revealed a 7823 bp deletion, coupled with a 1268 bp insertion 4 Kb downstream from the glutaredoxin gene. The msca1-ref sequence is shown in FIG. 4 (SEQ ID NO: 3).

EXAMPLE 2

Identification and Cloning of Additional msca1 Alleles

Two additional mutant alleles of msca1 were available, msca1-mg12 and msca1-6036 (Trimnell M, Fox T, Albertsen MC (2001) New male-sterile mutant allele of Msca1. MNL 75(63):31). Cloning and sequencing of the msca1-mg12 allele revealed a 490 bp deletion in the 3' region of the glutaredoxin gene. Alignment of a fertile and sterile msca1-mg12 allele is shown in FIG. 5. Alignment of the glutaredoxin region from a wild-type plant (Missouri 17), an msca1-mg12 fertile and sterile plant is shown in FIG. 6. Missing from the sterile plant is the GSH binding site, (LPVVFVGGRLLG; SEQ ID NO: 12). A motif for the redox region, CCMC (SEQ ID NO: 11), was present in the gene, and GSH binding region, LPVVFVGGRLLG (SEQ ID NO: 12), present in fertile plant, is absent in the sterile mutant as can be seen in the alignment shown in FIG. 6.

Figure 7:
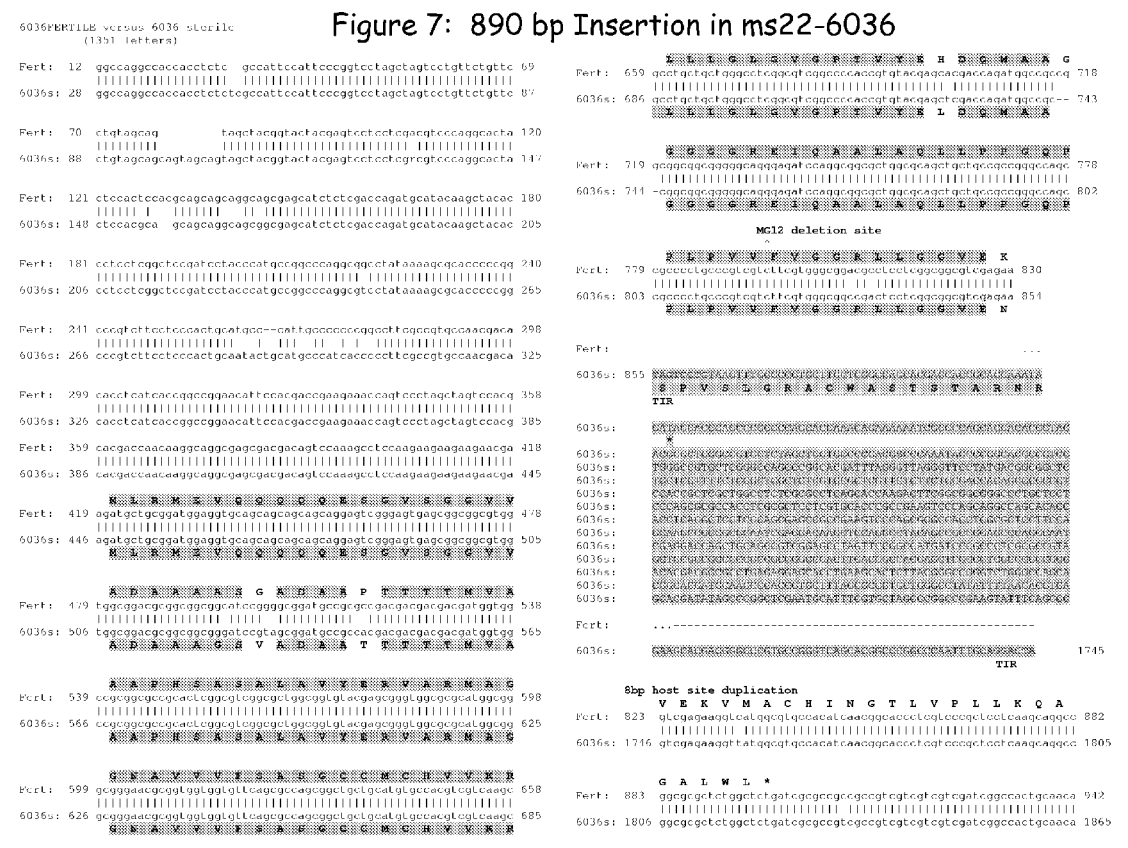

In cloning and sequencing of the msca1-6036 allele, a ~850 bp insertion was detected. Alignment showing comparison with a fertile plant versus the sterile allele is shown in FIG. 7. This insertion created an 8 bp host site duplication (GTC-GAGAA) and it also appears to contain small perfect TIRs (See the region of the sequence following base 854 in FIG. 7, marked at the start with "TIR"). It was also noted there is ~200 bp of significant homology at the ends of the insertion, reminiscent of a plant transposon. A graphic alignment of the msca1 coding region, genomic region, the reference allele, the msca1-mg12 allele and msca1-6036 allele is shown in FIG. 8.

EXAMPLE 3

Identification of Promoter

Upstream of the likely translational start codon at 1133 bp of SEQ ID NO: 1 of Msca1, 1132 bp of DNA was present in the genomic clone of Msca1. A reasonable TATA box was observed by inspection, starting at base 921 of SEQ ID NO: 1 and about 200 bp upstream of the translational start codon. See FIG. 9, which is SEQ. ID NO 15. The putative TATA box (TATAAAA) is underlined. Thus, the present invention encompasses a DNA molecule having a nucleotide sequence of SEQ ID NO: SEQ ID NO: 15 (FIG. 9), or those with sequence identity, which hybridize to same under stringent conditions and fragments, and having the function of a male tissue-preferred regulatory region.

EXAMPLE 4

Library Screening to Identify Msca1 from Rice

As noted above, Msca1 is a male fertility gene in maize. When it is mutated, and made homozygous recessive, male sterility will result. An orthologue of Msca1 was identified in rice. The rice Deleteagene population was prepared and used to screen for individuals harboring deletions of the msca1 gene. (Xin Li et. al A fast neutron deletion mutagenesis-based reverse genetics system for plants. *The Plant Journal* Volume 27 Page 235—August 2001). With this process, random deletion libraries are produced using fast neutrons to cause mutations. The libraries are screened for specific deletion mutants using polymerase chain reaction (PCR). In a typical protocol, 18 seeds from lines are pooled, planted, seedlings collected and genomic DNA isolated from the tissue. The DNA so isolated from all the mutated lines is collected into pools, beginning with mega pools, each having DNA of 2592 lines. A pair of primers are selected that are specific to sequences which flanks a gene targeted for deletion along with another pair of internally nested primers. The primers used for msca1 were as follows:

```
5' TGAGCATGCATGCTAAGCTAGTACTCCAGC  (SEQ ID NO: 20)

5' GTGATCCTCTCTGATGGTGACAACGAAGAC  (SEQ ID NO: 21)
```

The goal is to screen the library with one primer specific to the gene and a primer specific to the insertion element in such a way that one can discriminate between amplification of wild-type DNA from insertion DNA in large pools. The primers amplify both wild-type and mutant genes, but the PCR extension time is reduced in order to suppress amplification of the wild-type DNA. A long extension time is first used to confirm primer quality, then a shorter extension time to determine under what conditions amplification of wild-type DNA is suppressed. This time is used to screen the mega pools. A second round of PCR using nested primers is used to increase sensitivity. Gel electrophoresis detects the presence of amplified fragments in deletion alleles, and if a band is found in a mega pool, PCR analysis continues on smaller pool groups until a single plant is identified.

Primers derived from the rice msca1 gene yielded a putative deletion product in the initial screen of the 10 mega pools (having 2592 families per pool), which encompasses the entire mutant population. From this a deletion product in mega pool 7 was identified. This product was cloned and sequenced and was identified as a deletion allele of the rice msca1 gene as shown in FIG. 13. Subsequent screenings were performed on the nine superpools comprised of 288 families per pool, the 16 pools (having 16 families per pool), the 9 sub pools (two families per pool) to ultimately identify the individual families harboring the deletion. Two families were identified. Seed from each of these families were grown and genotyped using a set of wild-type primers and a set of primers that specifically amplify across the deletion. Family 21-77 was identified as containing the deletion in the rice msca1 gene and 2 plants within this family were homozygous for the mutation. Plants from family 21-77 were grown to maturity and male fertility phenotype was noted. The two plants genotyped as being homozygous for the msca1 deletion were completely male sterile, whereas sibling plants were male fertile, confirming the function of Msca1 in rice as being required for male fertility, analogous to the maize Msca1 function. Cytological examination of the anthers showed them to be small and mis-shapened with no evidence of microspore development. Stigmas from mutant flowers appeared to be normal. Crosses onto one of the mutant panicles resulted in seed set, demonstrating the female flower is viable. The second mutant had its panicle bagged and did not set any seed, confirming the male sterility phenotype.

EXAMPLE 5

Cloning and Sequence of Msca1 from Rice

A wildtype rice Msca1 gene from plant variety M202 (Johnson, C. W., Carnahan, H.L., Tseng, S. T., Oster, J.J., and Hill, J.E. Registration of "M202" rice. Crop Science, Vol 26. January-February. 1986 page 198) was cloned and sequenced using methods described supra and the 2860 base pairs of nucleotide sequence is shown in FIG. 10 (SEQ ID NO: 16). The putative amino acid sequence is shown in FIG. 11 (SEQ ID NO: 17). A motif for the redox region, CCMC, and the GSH binding region VPVVFVGGRLLG (SEQ ID NO: 11 and 25, respectively) is present in the rice Msca1 protein as shown in FIG. 11. The subclone of this gene is very similar in size and sequence composition to the maize Msca1 genomic clone that has been shown to complement the maize Msca1 mutation.

EXAMPLE 6

Identification of Msca1 Promoter from Rice

Upstream of the likely translational start codon at 1317 bp of SEQ ID NO: 16 (FIG. 10) of Msca1, 1316 bp of DNA was present in the genomic clone of rice Msca1. A reasonable TATA box was observed by inspection, starting at base 1008 of SEQ ID NO: 16 and about 200 bp upstream of the translational start codon. See FIG. 12, which is SEQ. ID NO: 18 showing the promoter. The putative TATA box (TATATATATATA) (SEQ ID NO: 22). is underlined. Thus, the present invention encompasses a DNA molecule having a nucleotide sequence of SEQ ID NO: 18 (or those with sequence identity or which hybridize under stringent conditions or fragments of same) and having the function of a male tissue-preferred regulatory region.

EXAMPLE 7

Construct Preparation with Msca1 Gene

A construct designated PHP27077 is made by assembling following DNA components:
1. The plasmid pSB11 backbone DNA (pSB31 lacking the EcoRI fragment carrying the 35SGUS and 35SBAR genes, Ishida et al., *Nature Biotechnol*. (1996) 14:745-750). This DNA backbone contains T-DNA border sequences and the replication origin from pBR322.
2. The 35S:PAT gene which encodes the enzyme phosphinothricin acetyltransferase (PAT) from *Streptomyces viridochomagenes* (nucleotides 6-557 from accession number A02774, Strauch et al. 1988, EP 0275957-A) under the transcriptional control of the cauliflower mosaic virus (CaMV) 35S promoter and terminator (nucleotides 6906-7439, and 7439-7632, respectively from Franck et al. 1980, *Cell* 21: 285-294).
3. The Msca1 sequence as set forth in FIG. 2 (SEQ ID NO: 1)

EXAMPLE 8

Transformation of Maize msca1 Plants

A male-sterile female which was homozygous for the msca1-ref mutant allele, (msca1) was repeatedly crossed with bulked pollen from maize Hi-type II plants (Armstrong 1994, In: Freeling and Walbot (eds). *The Maize Handbook*. Springer, New York, pp 663-671) resulting in the introgression of this msca1 allele in transformation amenable maize germplasm over multiple generations. The resultant source of material for transformation consisted of embryos segregating (1:1 or 3:1) for msca1 and allowed for both transformation directly into a homozygous msca1 background and to test the genetic complementation of the msca1 mutation in $T_0$ plants. *Agrobacterum*-mediated transformation was performed according to Zhao et al. 1999, (U.S. Pat. No. 5,981,840). Genotyping and molecular analysis (integration and plant transcription units/PTU) of transformants were done according Cigan et al., (*Sex. Plant. Reprod*. 1(2001) 4:135-142). Single copy, intact PTU events were identified by Southern analysis. Msca1 genotyping was accomplished by PCR of the single copy events. No morphological difference was observed between the transgenic plants and the non-transgenic control plants except for the degree of male fertility. Transformants were completely male fertile while non-transgenic control plants were completely male sterile, indicating that the expression of the Msca1 gene complemented the homozygous recessive msca1 male sterile phenotype.

EXAMPLE 9

Transformation of msca1 Plants with a Construct with msca1 Having a Frameshift

A second construct, PHP27618, is essentially the same as PHP27077, but has had a frameshift introduced into the msca1 gene, adding four base pairs at position 1508 of the sequence SEQ ID NO: 1) to disrupt the putative translation of the gene. Single copy, intact PTU events were identified by Southern analysis. Msca1 genotyping was done by PCR on the single copy events. Male fertility/sterility phenotype scores were taken at flowering. Results show that the frame-shifted Msca1 genomic fragment does not restore male fertility to msca1/msca1 plants which indicates that the putative translation product shown in FIG. 3 is the correct translational frame for the Msca1 gene. Specific results are shown below. PHP27077—10 Single Copy Events

| Events | Genotype | Fertility |
|---|---|---|
| 2 | Msca1/Msca1 | F |
| 1 | Msca1/msca1 | F |
| 7 | msca1/msca1 | F |

PHP27618 (Frame Shift)—6 Single Copy Events

| Events | Genotype | Fertility |
|---|---|---|
| 2 | Msca1/msca1 | F |
| 4 | msca1/msca1 | S |

EXAMPLE 10

Expression of Promoter

A construct PHP28154 was prepared with bases 1-1109 of the Msca1 promoter (SEQ ID NO: 15) and also included the cyan fluorescent protein (CFP) marker (Bolte et al. (2004) *J. Cell Science* 117: 943-54 and Kato et al. (2002) *Plant Physiol* 129: 913-42). Following *Agrobacterium* transformation (into GS3, the events were subjected to quantitative polymerase chain reaction (QPCR) of the PAT gene to determine copy number. Duplicate plants for most of the events were sent to the greenhouse. Tissue dissection from the duplicates was initiated at around the three to four leaf stage through the eight leaf stage. No signal could be seen in vegetative meristems, or in any other plant part e.g. roots, leaves. Well after the meristem had transitioned into a floral structure and anthers were being formed, CFP signal could be observed in the anther initials up through a developed anther (~1 mm). The signal disappeared once the anther had fully developed pollen mother cells, just prior to meiosis. This observation of CFP expression demonstrates the role of Msca1 in determining anther morphology.

EXAMPLE 11

Complementation Study of an Alternative Msca1 Promoter Fragment

Another construct, PHP27612, was prepared which included a smaller portion of the Msca1 genomic sequence. This fragment included 1291 bases of the genomic Msca1, starting from position 610 to 1900 bp SEQ ID NO: 1 (FIG. 2) which corresponds to a promoter length of 522 bases, from 610 to 1132 bases of the promoter sequence in FIG. 9. (SEQ ID NO: 15). The construct was prepared with the following components:

1. The plasmid pSB11 backbone DNA (pSB31 lacking the EcoRI fragment carrying the 35SGUS and 35SBAR genes, Ishida et al., *Nature Biotechnol*. (1996) 14:745-750). This DNA backbone contains T-DNA border sequences and the replication origin from pBR322.
2. The PG47PRO:ZM-AA1 gene which contains alpha-amylase 1 coding region from *Zea mays*.
3. LTP2:DS-RED2 (ALT1) which contains red florescence coding region (a variant of *Discosoma* sp. red fluorescent protein (DsRed), from Clontech mutated to remove BstEII site, codon sequence unchanged) driven by LTP2 promoter, supra.

Plants were transformed with PHP27612 as described supra, into msca1 sterile mutants. The introduction of the construct did not complement the mutation and the plants remained sterile, indicating that there are regulatory elements outside of this 1291 basepair fragment that are required for normal Msca1 biological function.

As is evident from the above, nucleotide sequences which map to the short arm of chromosome 7 of the *Zea mays* genome, at the same site as the Msca1 gene, and its alleles, are genes critical to male fertility in plants, that is, are necessary for fertility of a plant, or, when mutated from the sequence found in a fertile plant, cause sterility in the plant. Thus it can be seen that the invention achieves at least all of its objectives.

What is claimed is:

1. A method of maintaining a homozygous recessive condition of a male sterile plant, the method comprising:
   (a) providing a first plant comprising homozygous recessive alleles of a Msca1 gene wherein said plant is male sterile;
   (b) providing a second plant comprising homozygous recessive alleles of the Msca1 gene and a construct in the hemizygous condition, the construct comprising:
      (i) a first nucleotide sequence comprising the Msca1 nucleotide sequence, that when expressed in the first plant would restore male fertility;
      (ii) a second nucleotide sequence that when expressed inhibits the function or formation of viable male gametes in the second plant, such that viable male gametes are produced in the second plant containing the recessive allele of Msca1 and that do not contain the construct; and
   (c) fertilizing the first plant with the male gametes of the second plant to produce progeny which maintain the homozygous recessive condition of the first plant,
   wherein the first nucleotide sequence is selected from the group consisting of:
   (a) SEQ ID NO: 16;
   (b) a nucleic acid sequence encoding the amino acid sequence comprising SEQ ID NO: 17;
   (c) a nucleic acid sequence having at least 90% identity to the full length of any of the foregoing sequences wherein the sequence impacts male fertility in a plant;
   (d) a nucleic acid sequence having at least 95% identity to the full length of any of the sequences of parts (a) or (b) wherein the sequence impacts male fertility in a plant; and
   (e) a nucleic acid sequence which hybridizes to the full length complement of any of the sequences of parts (a) or (b) under highly stringent conditions of a wash of 0.1 SSC, 0.1% (w/v) SDS at 65° C. wherein the sequence impacts male fertility in a plant.

2. The method of claim 1, wherein the first nucleotide sequence is operably linked to a third nucleotide sequence regulating expression of the first nucleotide sequence.

3. The method of claim 2 wherein the third nucleotide sequence is selected from the group consisting of:
   (a) SEQ ID NO: 18; and
   (b) a functional fragment of SEQ ID NO: 18, wherein said fragment is required for male tissue preferred expression.

4. The method of claim 3, wherein the second nucleotide sequence is operably linked to a fourth nucleotide sequence, the fourth nucleotide sequence directing expression preferentially to male gametes.

5. The method of claim 4, wherein the second nucleotide sequence is selected from the group consisting of the nucleotide sequence of the DAM methylase gene, *Zea mays* alpha amylase gene, and a cytotoxin encoding gene.

6. The method of claim 4, wherein the fourth nucleotide sequence is selected from the group consisting of the regulatory region of the polygalacturonase 47 gene, Zm13 gene, pectin methylesterase gene, calmodulin binding protein gene, actin depolymerizing factor gene, profilin gene, and sulphated pentapeptide phytosulphokine gene.

7. The method of claim 3, wherein said construct further comprises a fifth nucleotide sequence encoding a product capable of being used for selection of plant cells having the construct.

8. The method of claim 7, further comprising selecting for said second plant by identifying plants having said construct.

9. The method of claim 2, wherein the third nucleotide sequence functions only in the presence of an inducing substance or condition.

10. The method of claim 1, wherein the second nucleotide sequence is linked to a third nucleotide sequence, the third nucleotide sequence directing expression preferentially to male gametes.

11. The method of claim 10, wherein the second nucleotide sequence is selected from the group consisting of the nucleotide sequence of the DAM methylase gene, *Zea mays* alpha amylase gene, and cytotoxin encoding gene.

12. The method of claim 10, wherein the third nucleotide sequence is selected from the group consisting of the regulatory region of the polygalacturonase 47 gene, Zm13 gene, pectin methylesterase gene, calmodulin binding protein gene, actin depolymerizing factor gene, profilin gene, and sulphated pentapeptide phytosulphokine gene.

13. The method of claim 1, wherein said construct further comprises a third nucleotide sequence encoding a product capable of being used for selection of plant cells having the construct.

14. The method of claim 13 wherein the third nucleotide sequence is selected from the group consisting of red fluorescent gene, cyan fluorescent protein gene, yellow fluorescent protein gene, luciferase gene, green fluorescent protein gene, anthocyanin p1 gene and phosphinothricin acetyltransferase encoding gene.

15. The method of claim 13 further comprising selecting for said second plant by identifying plants having said construct.

16. A method of producing seed from a plant having male gametes, the method comprising:
   (a) introducing into a male sterile plant comprising homozygous recessive alleles of a Msca1 gene, a construct in the hemizygous condition comprising:
      (i) a first nucleotide sequence comprising the Msca1 nucleotide sequence;
      (ii) a second nucleotide sequence, that when expressed inhibits the function or formation of male gametes in the plant, such that the plant produces viable male gametes that do not contain the construct;
   (b) self fertilizing the plant; and
   (c) producing seed which contain the construct,
wherein the first nucleotide sequence is selected from the group consisting of:
   (a) SEQ ID NO: 16;
   (b) a nucleic acid sequence encoding the amino acid sequence comprising SEQ ID NO: 17;
   (c) a nucleic acid sequence having at least 90% identity to the full length of any of the foregoing sequences wherein the sequence impacts male fertility in a plant;
   (d) a nucleic acid sequence having at least 95% identity to the full length of any of the sequences of parts (a) or (b) wherein the sequence impacts male fertility in a plant; and
   (e) a nucleic acid sequence which hybridizes to the full length complement of any of the sequences of parts (a) or (b) under highly stringent conditions of a wash of 0.1 SSC, 0.1% (w/v) SDS at 65° C. wherein the sequence impacts male fertility in a plant.

17. A method of restoring male fertility in a male sterile plant, the male sterile plant comprising homozygous recessive alleles of a gene that impacts male fertility, the method comprising introducing into said plant a nucleotide sequence that is the functional complement of the homozygous recessive condition, wherein the nucleotide sequence is selected from the group consisting of:
   (a) SEQ ID NO: 16;
   (b) a nucleic acid sequence encoding the amino acid sequence comprising SEQ ID NO: 17;
   (c) a nucleic acid sequence having at least 90% identity to the full length of any of the foregoing sequences wherein the sequence impacts male fertility in a plant;
   (d) a nucleic acid sequence having at least 95% identity to the full length of any of the sequences of parts (a) or (b) wherein the sequence impacts male fertility in a plant; and
   (e) a nucleic acid sequence which hybridizes to the full length complement of any of the sequences of parts (a) or (b) under highly stringent conditions of a wash of 0.1 SSC, 0.1% (w/v) SDS at 65° C. wherein the sequence impacts male fertility in a plant.

18. The method of claim 1 wherein said first nucleotide sequence is selected from the group consisting of:
   (a) SEQ ID NO: 16;
   (b) a nucleic acid sequence encoding the amino acid sequence comprising SEQ ID NO: 17;
   (c) a nucleic acid sequence having at least 95% identity to the full length of any of the foregoing sequences wherein the sequence impacts male fertility in a plant; and
   (d) a nucleic acid sequence which hybridizes to the full length complement of any of the sequences of parts (a) or (b) under highly stringent conditions of a wash of 0.1 SSC, 0.1% (w/v) SDS at 65° C. wherein the sequence impacts male fertility in a plant.

19. The method of claim 3 wherein said first nucleotide sequence is selected from the group consisting of:
   (a) SEQ ID NO: 16;
   (b) a nucleic acid sequence encoding the amino acid sequence comprising SEQ ID NO: 17;
   (c) a nucleic acid sequence having at least 95% identity to the full length of any of the foregoing sequences wherein the sequence impacts male fertility in a plant; and
   (d) a nucleic acid sequence which hybridizes to the full length complement of any of the sequences of parts (a) or (b) under highly stringent conditions of a wash of 0.1 SSC, 0.1% (w/v) SDS at 65° C. wherein the sequence impacts male fertility in a plant.

20. The method of claim 16 wherein said first nucleotide sequence is selected from the group consisting of:
   (a) SEQ ID NO: 16;
   (b) a nucleic acid sequence encoding the amino acid sequence comprising SEQ ID NO: 17;
   (c) a nucleic acid sequence having at least 95% identity to the full length of any of the foregoing sequences wherein the sequence impacts male fertility in a plant; and
   (d) a nucleic acid sequence which hybridizes to the full length complement of any of the sequences of parts (a) or (b) under highly stringent conditions of a wash of 0.1 SSC, 0.1% (w/v) SDS at 65° C. wherein the sequence impacts male fertility in a plant.

21. The method of claim 17 wherein said nucleotide sequence is selected from the group consisting of:
   (a) SEQ ID NO: 16;
   (b) a nucleic acid sequence encoding the amino acid sequence comprising SEQ ID NO: 17;
   (c) a nucleic acid sequence having at least 95% identity to the full length of any of the foregoing sequences wherein the sequence impacts male fertility in a plant; and
   (d) a nucleic acid sequence which hybridizes to the full length complement of any of the sequences of parts (a) or (b) under highly stringent conditions of a wash of 0.1 SSC, 0.1% (w/v) SDS at 65° C. wherein the sequence impacts male fertility in a plant.

* * * * *

SEQUENCE LISTING

```
<160> NUMBER OF SEQ ID NOS: 25

<210> SEQ ID NO 1
<211> LENGTH: 3052
<212> TYPE: DNA
<213> ORGANISM: Zea mays

<400> SEQUENCE: 1
aattcgcggg acgtggcgtt gtcggctccg tgtcggcggc cgaaccacca cgaatcactg       60
```

```
acgtatctcg tctcctctct cctctagact cccacgatac ggccaacgaa gtgtatgtac    120
atatataccc atggtcatat ggcaacaaac gccaacgcca gcagagcact gcccggcggc    180 cttttttccca tctctctctc tctctctgat ggggtgtgca tgcctgactg actgatagat    240
agatagatgg tcaggtccgt ctgatcctca tcggcctagc tcaccccacg cgaaaaaagc    300
cactgctggc tggcgcccag ttgcgcttgc aacagtcact ttaacgagct ccgtccttgc    360
gtttgccctc ctcgctctgc ccctgccgcc gctgccgctg cgtggtggtg ctggtgcatg    420
aggcaggcag gcgtactagt gcatgcaatt gcaatgcaac cgtaggagtg cgttgcgtac    480
cctggtctgt ccctgcggcc tggcctgccc ttgttcgttg cggatgcggg gggtgccggg    540
tgggtactgt actgtactac tgggtagaga gatactacta gatagagaga gagagaggtc    600
ggtcaccccg ggcgcgggac acagcctctg cgaaaaagcg atccatgtcg cgcctagctt    660
tgacccggaa cggatccccc aaccaggaac cagcagagca ggagggccag gccaccacct    720
ctcgccattc cattcccggt cctagctagt cctgttctgt tcctgtagca gtagcagtag    780
ctacggtact acgagtcctc ctcgacgtcc caggcactac tccactccac gcagcagcag    840
gcagcgagca tctctcgacc agatgcatac aagctacacc ctcctcggct ccgatcctac    900
ccatgccggc ccaggcggcc tataaaagcg caccccggc ccgtcttcct cccactgcat    960
gcccattgcc cctcccccgg ccttcgccgt gccaacgaca cacctcatca ccggccggaa    1020
cattccacga ccgaagaaac cagtccctag ctagtccacg cacgaccaac aaggcaggcg    1080
agcgacgaca gtccaagcct ccaagaagaa gaagaagaag aagaagaaga agatgctgcg    1140
gatggaggtg cagcagcagg agtcgggagt gagcggcggc gtggtggcgg acgcggcggc    1200
ggcgggatcc gtggcggaag ccgcgacgac gacgatggtg gccgcggcgc cgcactcggc    1260
gtcggcgctg gcggtgtacg agcgggtggc gcgcatggcg ggcgggaacg cggtggtggt    1320
gttcagcgcc agcggctgct gcatgtgcca cgtcgtcaag cgcctgctgc tgggcctcgg    1380
cgtcggcccc accgtgtacg agctcgacca gatggccggc ggcggcgggg gcagggagat    1440
ccaggcggcg ctggcgcagc tgctgccgcc gggccagccg cccctgcccg tcgtcttcgt    1500
tggcggccgc ctcctcggcg gcgtcgagaa ggtcatggct tgccacatca acggcaccct    1560
cgtcccgctc ctcaagcagg ccggcgcgct ctggctctga tcgcgccgtc gtcgtcgtcg    1620
tcgtcgtcga tcggccactg caacagacaa cagtgtgcgt gtgtgtgtgg ctgtgtgcgc    1680
atctccgtgc atgcgatcga tcgctgcccc ttagttagtt actcactact tactaccttg    1740
cgttttaatg taacctctac taagctagct agctcttgtc ctgttccgtg catgagagag    1800
gtcgagtaat gccgcaatcg cctgctgcag ttaatgcagc agcgcacgac gacgtcgccg    1860
atgatggttg atggtgcatc gattattgca ctccatggat atcatccatc ttaaccggac    1920
gtggacgtac ggtgccccgg ccggtgcagc aggggggccag tcagcagcct tgtaaaagcg    1980
tacccgtacg tacgtcgtcg agacatcaac gacgtacggg gacgcaacgc aaccagccaa    2040
aacgggatcg ttcgaactag agcaagacgt acggctttcg atgagctggc ggtgtgttag    2100
actgttagac ataaaaaaaa tacataatat aataaacata gaagctatcc atggtttcta    2160
gctttatgtt gggactgcac taatgaccat agcaatgcgc tcatcaagtt atcaaatttt    2220
actccctcca tggtgcctca caacagtacg tacgtagtcg tttcgtgatg aaacacaata    2280
cacaaaattt tactccctcc gtttcatttt acaagtcgtt tccaacagcc aatgcataaa    2340
tagcagcgac aactaaaatg aaacggagta atacgtaaaa agtctttata ggaaacaaaa    2400
cacgagcgtc aaccgtcaat cttcattata cgatgagagt ttgtagaaca tagaatacaa    2460
```

-continued

```
ttagtcgaat cccttctcgt gcgatatgta tatatacata cgacggacga actaaaccag    2520
taccataatc aaaatcaatg tattcagtaa gcccatctct aaatttccta aagtgcaaac    2580
aaagattaga ggtacgtcgc aaatatatat aaaaaaatcc actacacacg atcctctaat    2640
tactgctcct tattatcatg gttaggccac gtacaacggg tgtcttaagc tgtgtcttgt    2700
tgaaggaggg taaatgtaaa aaaactcaag acacatatct taacgaagat attgtgtttg    2760
gctttatgct cgatacatat gggaacagct gattggtaaa attaatttat tgaatgttcc    2820
gattgatgca atgaatatag caagacatat gttttaatta gacacgtcca ctgtattata    2880
ttgtgtttta gctatatctt atacttggag tatcgtgcag cggtgtcagg gttgtacata    2940
catgccctta gccatctacc gacggcattc aatgcgtgtg agataaatca ggataagagc    3000
gaaccatgag atgcataaga gaaccgattt ccctgaaata tgaaactgta gg            3052
```

<210> SEQ ID NO 2
<211> LENGTH: 155
<212> TYPE: PRT
<213> ORGANISM: Zea mays

<400> SEQUENCE: 2

```
Met Leu Arg Met Glu Val Gln Gln Gln Glu Ser Gly Val Ser Gly Gly
 1               5                  10                  15

Val Val Ala Asp Ala Ala Ala Gly Ser Val Ala Glu Ala Ala Thr
             20                  25                  30

Thr Thr Met Val Ala Ala Pro His Ser Ala Ser Ala Leu Ala Val
         35                  40                  45

Tyr Glu Arg Val Ala Arg Met Ala Gly Gly Asn Ala Val Val Phe
     50                  55                  60

Ser Ala Ser Gly Cys Cys Met Cys His Val Val Lys Arg Leu Leu Leu
 65                  70                  75                  80

Gly Leu Gly Val Gly Pro Thr Val Tyr Glu Leu Asp Gln Met Ala Gly
                 85                  90                  95

Gly Gly Gly Gly Arg Glu Ile Gln Ala Ala Leu Ala Gln Leu Leu Pro
            100                 105                 110

Pro Gly Gln Pro Pro Leu Pro Val Val Phe Val Gly Gly Arg Leu Leu
        115                 120                 125

Gly Gly Val Glu Lys Val Met Ala Cys His Ile Asn Gly Thr Leu Val
    130                 135                 140

Pro Leu Leu Lys Gln Ala Gly Ala Leu Trp Leu
145                 150                 155
```

<210> SEQ ID NO 3
<211> LENGTH: 2856
<212> TYPE: DNA
<213> ORGANISM: Zea mays

<400> SEQUENCE: 3

```
ggacgcgagt gtgacctttt gcatggcaaa ctcgatcgca gtcgcagtct cgctgcatgc      60
gtgcgtacgt acgtacgtgc aacgcaatgg atcggaatgc ccgatctatc gaccgacgtg     120
gaggaggacg gtcgatctgc atgcatgcga acagtgcaag tggacatata tatatgcacc     180
gttggacgtt ggtacgggcc gggggcgcgg tgtggccgcg tgcacatgca gcagcccttta   240 tgatggggt acgtgcacga actaaactaa cggtgccaca caagaaagtg gagagaactt     300
ccctcgatca ggtgctagtt gcttcttgag gcccagatgt cggaggcccg gcctgccgta   360
cgtacgtaac gtgacacgat gcgctgatgt gcatcatgca tgttatatgt atatatcata   420
```

| | |
|---|---|
| taatactcca gcatgtcggc gaccacacct tgcttcagga cttgtttcgt ccggtccctc | 480 |
| agctcgctcc gacaacgacg acgacactct ctcccggccc ttgtcgcgct ctcgtccaac | 540 |
| aacagcagtc gtagtagcaa gaaagccaaa tgtgtgttaa tcataaattg ttggtcaaaa | 600 |
| ggctacctac cgtgtcctaa caagaccaaa aagacgtgtg ataatgttaa ctagaagaag | 660 |
| cagtagcctt ttccactttt aactggttca ctgcacactg aagaaacatg tatatatacc | 720 |
| ccctctctct atctctctcc cttgaaatca acttttcttt taacgctctc ttcgtttcca | 780 |
| tggcatgcat cgttcgcctc cccccccccc cctcattgc tccatccggc cttgcgttgt | 840 |
| ataccacctc cgacgaccct aaataacaga taaagtttta gtttccatga gtgaagcctc | 900 |
| tatgctttat tcttaaaatc cgacgaccaa ttctattata taaaaaggag tataattggt | 960 |
| gtacaaatgc atggcactgg aaaaaaagtc aagcgttaaa atacattcca tgtcattatc | 1020 |
| aaactatata tgttaactag gtgagtaccc gtgcgttgca acgagatcat ataataacat | 1080 |
| aataagttat atacaaaatg tgtcttatat tgttataaaa aatatttcat aatccattta | 1140 |
| taatcctagc catacataaa ttttgttatt ttaatttagc tgtttcatta tttcattgca | 1200 |
| accatcagta tcatgcagac ttcgatatat gccacgattt gcatggtctc atcattgaag | 1260 |
| agcacgtgtc acacctaccg gtagaagttc cctcgtacat tgtcagtcat caggtacgca | 1320 |
| ccaccataca cgcttgctta aacaaaaaaa gcaagtgcat gtgtttgcga agataattaa | 1380 |
| aggcaggccg acacaaaagc taccccgacg atggcgagtg gtcattgttg tcggtcctcc | 1440 |
| tctgcgtcac ctctggtgcc aagatgacgc catagtcctt gatatagtag tcgtcgaacg | 1500 |
| cgcatgacat gacgagtacc gatgactctt ggctgggctg tcaaacgaag tgcaccccgg | 1560 |
| gctcatcagc gaggtagtac acctagccgt tgcaccaccg gatgtgccgc tcctctacat | 1620 |
| aaatcttgtt cgaggacact cacacaacgt cagcaacgac cgtcgtccca gcgcataaga | 1680 |
| attcatggcc ggtcagtagt gacttacgtg ggaggttgag cttcaggtgg atgatgagct | 1740 |
| ggatggtgtg acggcgccgt tgtcggatgc ggtgcccaga acaacccgag agtcgccggt | 1800 |
| gttggcgacg accatgaggt cccctatttt gaagatggac aatgcggagc agccgctctg | 1860 |
| aaccgcgtcc aagcaattgc atgcaaggct ctttttttaaa tactactccc tccatccaaa | 1920 |
| atatataatt caggaatctc gttgataatt atctactact acacattatg caaaggtagc | 1980 |
| aggtagactt tgagagagat gtattatata tttttactat aacaaatatt aacataaaca | 2040 |
| cacatgtggt gtagtagtag ctacgagcac atttgcttga gaggtcgcag gttcgaatct | 2100 |
| cattggagcc acatttgtga gaatgagatt tgcgggagg ggcactag caacatgaat | 2160 |
| gagaatggga atgggcttta cggggagggg agaatgggaa agacattgcg ggaatggaaa | 2220 |
| tgacagaaca cggaatggca gcctacccctt taccgtctta ataagtagta gagatcaggc | 2280 |
| aacacagcag agtagtattg caccgttacc agttcagctg aggctgagac tgagcgcgca | 2340 |
| aaggtacagt ttgtgtccgg caagggaaga cgacagtcg acgaccgacc gaccgacaga | 2400 |
| ccgaggaccg gaccgccgga cgggaaagtc aatgggctgg gcagtttcat gctagtgggc | 2460 |
| tgaacgatct gttatttgat gtggcccacc actgttgagg tccactagtc ctttactcct | 2520 |
| ttggagcgac gagtcggccc atatcctagt tccgcagaga gactgacgaa gagaccagtg | 2580 |
| gaagttggaa ccctgaaacc cgctgcctac aactgcagct ccgttttatt ttgccttttc | 2640 |
| acacgacggc aatctggttt ttatttatag cgtaacggaa atactatact acagcagagt | 2700 |
| ttttttttat ttggataaag gcgttggcgt gttgcaaata aagacgcgtg tcggtgtcac | 2760 |
| aacgaagaag aagaaaaagc aggttgatac ctaccactat actgtaccat atagagcgca | 2820 |

```
catgcagctg cgatctccct tcttccccca tccatc                              2856
```

<210> SEQ ID NO 4
<211> LENGTH: 939
<212> TYPE: DNA
<213> ORGANISM: Zea mays
<220> FEATURE:
<221> NAME/KEY: CDS
<222> LOCATION: (9)..(473)

<400> SEQUENCE: 4

```
agaagaag atg ctg cgg atg gag gtg cag cag cag gag tcg gga gtg agc        50
         Met Leu Arg Met Glu Val Gln Gln Gln Glu Ser Gly Val Ser
          1               5                  10 ggc ggc gtg gtg gcg gac gcg gcg gcg gga tcc gtg gcg gaa gcc             98
Gly Gly Val Val Ala Asp Ala Ala Ala Gly Ser Val Ala Glu Ala
 15                  20                  25                  30 gcg acg acg acg atg gtg gcc gcg gcg ccg cac tcg gcg tcg gcg ctg        146
Ala Thr Thr Thr Met Val Ala Ala Ala Pro His Ser Ala Ser Ala Leu
                 35                  40                  45 gcg gtg tac gag cgg gtg gcg cgc atg gcg ggc ggg aac gcg gtg gtg        194
Ala Val Tyr Glu Arg Val Ala Arg Met Ala Gly Gly Asn Ala Val Val
             50                  55                  60 gtg ttc agc gcc agc ggc tgc tgc atg tgc cac gtc gtc aag cgc ctg        242
Val Phe Ser Ala Ser Gly Cys Cys Met Cys His Val Val Lys Arg Leu
 65                  70                  75 ctg ctg ggc ctc ggc gtc ggc ccc acc gtg tac gag ctc gac cag atg        290
Leu Leu Gly Leu Gly Val Gly Pro Thr Val Tyr Glu Leu Asp Gln Met
 80                  85                  90 gcc gcc agc ggc ggg ggc agg gag atc cag gcc gcg ctg gcg cag ctg        338
Ala Ala Ser Gly Gly Gly Arg Glu Ile Gln Ala Ala Leu Ala Gln Leu
 95                 100                 105                 110 ctg ccg ccg ggc cag ccg ccc ctg ccc gtc gtc ttc gtt ggc ggc cgc        386
Leu Pro Pro Gly Gln Pro Pro Leu Pro Val Val Phe Val Gly Gly Arg
                115                 120                 125 ctc ctc ggc ggc gtc gag aag gtc atg gcg tgc cac atc aac ggc acc        434
Leu Leu Gly Gly Val Glu Lys Val Met Ala Cys His Ile Asn Gly Thr
            130                 135                 140 ctc gtc ccg ctc ctc aag cag gcc ggc gcg ctc tgg ctc tgatcgcgcc        483
Leu Val Pro Leu Leu Lys Gln Ala Gly Ala Leu Trp Leu
145                 150                 155 gtcgtcgtcg tcgatcggcc actgcaacag acaacagtgt gcgtgtgtgt gtggctgtgt        543
gcgcatctcc gtgcatgcga tcgatcgctg ccccttagtt agttactcac tacttactat        603
tactacgcct tgcgttttaa tgtaacctct actaagctag ctagctcttg ttctgttcca        663
tgcatgcatg agagaggtcg agtaatgctg caatcgcctg ctgcagttaa tgcagcagcg        723
cgcgcacgac gtcgccgatg atggtgcatc gattattgca ctccatggat catccatctt        783
aaccggacgt ggacgtacgg tgccccggcc ggtgcaggca gaggagggcg gcggccggcg        843
ctagctgcct ccggctgagg tcacagtctc acagagcagc aggccggggg ccagtcagca        903
gccttgtaaa agcaaacgta cgtacgtcgt cgagac                                  939
```

<210> SEQ ID NO 5
<211> LENGTH: 155
<212> TYPE: PRT
<213> ORGANISM: Zea mays

<400> SEQUENCE: 5

```
Met Leu Arg Met Glu Val Gln Gln Gln Glu Ser Gly Val Ser Gly Gly
 1               5                  10                  15
```

```
Val Val Ala Asp Ala Ala Ala Ala Gly Ser Val Ala Glu Ala Ala Thr
            20                  25                  30

Thr Thr Met Val Ala Ala Ala Pro His Ser Ala Ser Ala Leu Ala Val
        35                  40                  45

Tyr Glu Arg Val Ala Arg Met Ala Gly Gly Asn Ala Val Val Val Phe
    50                  55                  60

Ser Ala Ser Gly Cys Cys Met Cys His Val Val Lys Arg Leu Leu Leu
65                  70                  75                  80

Gly Leu Gly Val Gly Pro Thr Val Tyr Glu Leu Asp Gln Met Ala Ala
                85                  90                  95

Ser Gly Gly Gly Arg Glu Ile Gln Ala Ala Leu Ala Gln Leu Leu Pro
            100                 105                 110

Pro Gly Gln Pro Pro Leu Pro Val Val Phe Val Gly Gly Arg Leu Leu
        115                 120                 125

Gly Gly Val Glu Lys Val Met Ala Cys His Ile Asn Gly Thr Leu Val
    130                 135                 140

Pro Leu Leu Lys Gln Ala Gly Ala Leu Trp Leu
145                 150                 155

<210> SEQ ID NO 6
<211> LENGTH: 473
<212> TYPE: DNA
<213> ORGANISM: Zea mays
<220> FEATURE:
<221> NAME/KEY: CDS
<222> LOCATION: (3)..(389)

<400> SEQUENCE: 6 ag atg ctg cgg atg gag gtg cag cag cag cag cag gag tcg gga gtg      47
   Met Leu Arg Met Glu Val Gln Gln Gln Gln Gln Glu Ser Gly Val
   1               5                   10                  15 agc ggc ggc gtg gtg gcg gac gcg gcg gcg gga tcc gta gcg gat gcc    95
Ser Gly Gly Val Val Ala Asp Ala Ala Ala Gly Ser Val Ala Asp Ala
                20                  25                  30 gcc acg acg acg acg acg atg gtg gcc gcg gcg ccg cac tcg gcg tcg   143
Ala Thr Thr Thr Thr Thr Met Val Ala Ala Ala Pro His Ser Ala Ser
            35                  40                  45 gcg ctg gcg gtg tac gag cgg gtg gcg cgc atg gcg ggc ggg aac gcg   191
Ala Leu Ala Val Tyr Glu Arg Val Ala Arg Met Ala Gly Gly Asn Ala
        50                  55                  60 gtg gtg gtg ttc agc gcc agc ggc tgc tgc atg tgc cac gtc gtc aag   239
Val Val Val Phe Ser Ala Ser Gly Cys Cys Met Cys His Val Val Lys
65                  70                  75                  80 cgc ctg ctg ctg ggc ctc ggc gtc ggc ccc acc gtg tac gag ctc gac   287
Arg Leu Leu Leu Gly Leu Gly Val Gly Pro Thr Val Tyr Glu Leu Asp
                85                  90                  95 cag atg gcc gcc agc ggc ggg ggc agg gag atc cag gcg gcg ctg gcg   335
Gln Met Ala Ala Ser Gly Gly Gly Arg Glu Ile Gln Ala Ala Leu Ala
            100                 105                 110 cag ctg ctg ccg ccg ggc cag ccg ccc ctg ccc gac atc aac gac ata   383
Gln Leu Leu Pro Pro Gly Gln Pro Pro Leu Pro Asp Ile Asn Asp Ile
        115                 120                 125 cga aca ggctgaggtc acagtctcac agagcagcag gccgggggcc agtcagcagc    439
Arg Thr cttgtaaaag cgtacgtacg tacgtcgtcg agac                             473

<210> SEQ ID NO 7
<211> LENGTH: 129
<212> TYPE: PRT
<213> ORGANISM: Zea mays
```

<400> SEQUENCE: 7

```
Met Leu Arg Met Glu Val Gln Gln Gln Gln Glu Ser Gly Val Ser
1               5                  10                  15

Gly Gly Val Val Ala Asp Ala Ala Gly Ser Val Ala Asp Ala Ala
            20                  25                  30

Thr Thr Thr Thr Thr Met Val Ala Ala Pro His Ser Ala Ser Ala
        35                  40                  45

Leu Ala Val Tyr Glu Arg Val Ala Arg Met Ala Gly Gly Asn Ala Val
        50                  55                  60

Val Val Phe Ser Ala Ser Gly Cys Cys Met Cys His Val Val Lys Arg
65                  70                  75                  80

Leu Leu Leu Gly Leu Gly Val Gly Pro Thr Val Tyr Glu Leu Asp Gln
                85                  90                  95

Met Ala Ala Ser Gly Gly Gly Arg Glu Ile Gln Ala Ala Leu Ala Gln
            100                 105                 110

Leu Leu Pro Pro Gly Gln Pro Pro Leu Pro Asp Ile Asn Asp Ile Arg
            115                 120                 125

Thr
```

<210> SEQ ID NO 8
<211> LENGTH: 155
<212> TYPE: PRT
<213> ORGANISM: Zea mays

<400> SEQUENCE: 8

```
Met Leu Arg Met Glu Val Gln Gln Gln Glu Ser Gly Val Ser Gly Gly
1               5                  10                  15

Val Val Ala Asp Ala Ala Ala Gly Ser Val Ala Glu Ala Ala Thr
            20                  25                  30

Thr Thr Met Val Ala Ala Pro His Ser Ala Ser Ala Leu Ala Val
        35                  40                  45

Tyr Glu Arg Val Ala Arg Met Ala Gly Gly Asn Ala Val Val Phe
    50                  55                  60

Ser Ala Ser Gly Cys Cys Met Cys Asn Val Val Lys Arg Leu Leu Leu
65                  70                  75                  80

Gly Leu Gly Val Gly Pro Thr Val Tyr Glu Leu Asp Gln Met Ala Gly
                85                  90                  95

Gly Gly Gly Gly Arg Glu Ile Gln Ala Ala Leu Ala Gln Leu Leu Pro
            100                 105                 110

Pro Gly Gln Pro Pro Leu Pro Val Val Phe Val Gly Arg Leu Leu
            115                 120                 125

Gly Gly Val Glu Lys Val Met Ala Cys His Ile Asn Gly Thr Leu Val
        130                 135                 140

Pro Leu Leu Lys Gln Ala Gly Ala Leu Trp Leu
145                 150                 155
```

<210> SEQ ID NO 9
<211> LENGTH: 155
<212> TYPE: PRT
<213> ORGANISM: Zea mays

<400> SEQUENCE: 9

```
Met Leu Arg Met Glu Val Gln Gln Gln Glu Ser Gly Val Ser Gly Gly
1               5                  10                  15

Val Val Ala Asp Ala Ala Ala Gly Ser Val Ala Glu Ala Ala Thr
            20                  25                  30
```

```
Thr Thr Met Val Ala Ala Pro His Ser Ala Ser Ala Leu Ala Val
        35                  40                  45
Tyr Glu Arg Val Ala Arg Met Ala Gly Gly Asn Ala Val Val Phe
    50                  55                  60
Ser Ala Ser Gly Cys Cys Met Cys His Val Val Lys Arg Leu Leu Leu
65                  70                  75                  80
Gly Leu Gly Val Gly Pro Thr Val Tyr Glu Leu Asp Gln Met Ala Ala
                85                  90                  95
Ser Gly Gly Arg Glu Ile Gln Ala Ala Leu Ala Gln Leu Leu Pro
            100                 105                 110
Pro Gly Gln Pro Pro Leu Pro Val Val Phe Val Gly Gly Arg Leu Leu
            115                 120                 125
Gly Gly Val Glu Lys Val Met Ala Cys His Ile Asn Gly Thr Leu Val
        130                 135                 140
Pro Leu Leu Lys Gln Ala Gly Ala Leu Trp Leu
145                 150                 155

<210> SEQ ID NO 10
<211> LENGTH: 130
<212> TYPE: PRT
<213> ORGANISM: Zea mays

<400> SEQUENCE: 10

Met Leu Arg Met Glu Val Gln Gln Gln Gln Glu Ser Gly Val Ser
1               5                   10                  15
Gly Gly Val Val Ala Asp Ala Ala Gly Ser Val Ala Asp Ala Ala
            20                  25                  30
Thr Thr Thr Thr Thr Met Val Ala Ala Pro His Ser Ala Ser Ala
        35                  40                  45
Leu Ala Val Tyr Glu Arg Val Ala Arg Met Ala Gly Gly Asn Ala Val
    50                  55                  60
Val Val Phe Ser Ala Ser Gly Cys Cys Met Cys His Val Val Lys Arg
65                  70                  75                  80
Leu Leu Leu Gly Leu Gly Val Gly Pro Thr Val Tyr Glu Leu Asp Gln
                85                  90                  95
Met Ala Ala Ser Gly Gly Arg Glu Ile Gln Ala Ala Leu Ala Gln
            100                 105                 110
Leu Leu Pro Pro Gly Gln Pro Pro Leu Pro Asp Ile Asn Asp Ile Arg
            115                 120                 125
Thr Gly
    130

<210> SEQ ID NO 11
<211> LENGTH: 4
<212> TYPE: PRT
<213> ORGANISM: Zea mays

<400> SEQUENCE: 11

Cys Cys Met Cys
1

<210> SEQ ID NO 12
<211> LENGTH: 12
<212> TYPE: PRT
<213> ORGANISM: Zea mays

<400> SEQUENCE: 12

Leu Pro Val Val Phe Val Gly Gly Arg Leu Leu Gly
```

<210> SEQ ID NO 13
<211> LENGTH: 931
<212> TYPE: DNA
<213> ORGANISM: Zea mays
<220> FEATURE:
<221> NAME/KEY: CDS
<222> LOCATION: (410)..(886)

<400> SEQUENCE: 13

```
ggccaggcca ccacctctcg ccattccatt cccggtccta gctagtcctg ttctgttcct      60
gtagcagtag ctacggtact acgagtcctc ctcgacgtcc caggcactac tccactccac     120
gcagcagcag gcagcgagca tctctcgacc agatgcatac aagctacacc ctcctcggct     180
ccgatcctac ccatgccggc ccaggcggcc tataaaagcg cacccccggc ccgtcttcct     240
cccactgcat gcccattgcc ccccggcct  tcgccgtgcc aacgacacac ctcatcaccg     300
gccggaacat tccacgaccg aagaaaccag tccctagcta gtccacgcac gaccaacaag     360
gcaggcgagc gacgacagtc caaagcctcc aagaagaaga gaacgaag atg ctg cgg      418
                                                   Met Leu Arg
                                                     1
```

```
atg gag gtg cag cag cag cag cag gag tcg gga gtg agc ggc ggc gtg      466
Met Glu Val Gln Gln Gln Gln Gln Glu Ser Gly Val Ser Gly Gly Val
      5                  10                  15 gtg gcg gac gcg gcg gcg gca tcc ggg gcg gat gcc gcg ccg acg acg      514
Val Ala Asp Ala Ala Ala Ala Ser Gly Ala Asp Ala Ala Pro Thr Thr
 20                  25                  30                  35 acg acg atg gtg gcc gcg gcg ccg cac tcg gcg tcg gcg ctg gcg gtg      562
Thr Thr Met Val Ala Ala Ala Pro His Ser Ala Ser Ala Leu Ala Val
                 40                  45                  50 tac gag cgg gtg gcg cgc atg gcg ggg ggg aac gcg gtg gtg gtg ttc      610
Tyr Glu Arg Val Ala Arg Met Ala Gly Gly Asn Ala Val Val Val Phe
             55                  60                  65 agc gcc agc ggc tgc tgc atg tgc cac gtc gtc aag cgc ctg ctg ctg      658
Ser Ala Ser Gly Cys Cys Met Cys His Val Val Lys Arg Leu Leu Leu
         70                  75                  80 ggc ctc ggc gtc ggc ccc acc gtg tac gag cac gac cag atg gcc gcc      706
Gly Leu Gly Val Gly Pro Thr Val Tyr Glu His Asp Gln Met Ala Ala
     85                  90                  95 ggc ggc ggc ggg ggc agg gag atc cag gcg gcg ctg gcg cag ctg ctg      754
Gly Gly Gly Gly Gly Arg Glu Ile Gln Ala Ala Leu Ala Gln Leu Leu
100                 105                 110                 115 ccg ccg ggc cag ccg ccc ctg ccc gtc gtc ttc gtg ggc gga cgc ctc      802
Pro Pro Gly Gln Pro Pro Leu Pro Val Val Phe Val Gly Gly Arg Leu
                120                 125                 130 ctc ggc ggc gtc gag aag gtc atg gcg tgc cac atc aac ggc acc ctc      850
Leu Gly Gly Val Glu Lys Val Met Ala Cys His Ile Asn Gly Thr Leu
            135                 140                 145 gtc ccg ctc ctc aag cag gcc ggc gcg ctc tgg ctc tgatcgcgcc           896
Val Pro Leu Leu Lys Gln Ala Gly Ala Leu Trp Leu
        150                 155 gccgccgtcg tcgtcgtcga tcggccactg caaca                                931
```

<210> SEQ ID NO 14
<211> LENGTH: 1838
<212> TYPE: DNA
<213> ORGANISM: Zea mays
<220> FEATURE:
<221> NAME/KEY: CDS
<222> LOCATION: (421)..(885)

```
<400> SEQUENCE: 14
ggccaggcca ccacctctct cgccattcca ttcccggtcc tagctagtcc tgttctgttc      60
ctgtagcagc agtagcagta gctacggtac tacgagtcct cctcgrcgtc ccaggcacta     120
ctccacgcag cagcaggcag cggcgagcat ctctcgacca gatgcataca agctacaccc     180
tcctcggctc cgatcctacc catgccggcc caggcgtcct ataaaagcgc accccggcc      240 cgtcttcctc ccactgcaat actgcatgcc catcaccccc ttcgccgtgc caacgacaca     300
cctcatcacc ggccggaaca ttccacgacc gaagaaacca gtccctagct agtccacgca     360
cgaccaacaa gcaggcgag cgacgacagt ccaaagcctc caagaagaag aagaacgaag     420
```

| atg ctg cgg atg gag gtg cag cag cag cag cag gag tcg gga gtg agc | 468 |
|---|---|
| Met Leu Arg Met Glu Val Gln Gln Gln Gln Gln Glu Ser Gly Val Ser |  |
| 1           5                   10                  15 |  |

| ggc ggc gtg gtg gcg gac gcg gcg gcg gga tcc gta gcg gat gcc gcc | 516 |
|---|---|
| Gly Gly Val Val Ala Asp Ala Ala Ala Gly Ser Val Ala Asp Ala Ala |  |
|          20                  25                  30 |  |

| acg acg acg acg acg atg gtg gcc gcg gcg ccg cac tcg gcg tcg gcg | 564 |
|---|---|
| Thr Thr Thr Thr Thr Met Val Ala Ala Ala Pro His Ser Ala Ser Ala |  |
|      35                  40                  45 |  |

| ctg gcg gtg tac gag cgg gtg gcg cgc atg gcg ggc ggg aac gcg gtg | 612 |
|---|---|
| Leu Ala Val Tyr Glu Arg Val Ala Arg Met Ala Gly Gly Asn Ala Val |  |
| 50                  55                  60 |  |

| gtg gtg ttc agc gcc agc ggc tgc tgc atg tgc cac gtc gtc aag cgc | 660 |
|---|---|
| Val Val Phe Ser Ala Ser Gly Cys Cys Met Cys His Val Val Lys Arg |  |
| 65                  70                  75                  80 |  |

| ctg ctg ctg ggc ctc ggc gtc ggc ccc acc gtg tac gag ctc gac cag | 708 |
|---|---|
| Leu Leu Leu Gly Leu Gly Val Gly Pro Thr Val Tyr Glu Leu Asp Gln |  |
|          85                  90                  95 |  |

| atg gcc gcc ggc ggc ggg ggc agg gag atc cag gcg gcg ctg gcg cag | 756 |
|---|---|
| Met Ala Ala Gly Gly Gly Gly Arg Glu Ile Gln Ala Ala Leu Ala Gln |  |
|          100                 105                 110 |  |

| ctg ctg ccg ccg ggc cag ccg ccc ctg ccc gtc gtc ttc gtg ggc ggc | 804 |
|---|---|
| Leu Leu Pro Pro Gly Gln Pro Pro Leu Pro Val Val Phe Val Gly Gly |  |
|          115                 120                 125 |  |

| cga ctc ctc ggc ggc gtc gag aat agt cct gta agt ttg ggc cgt gct | 852 |
|---|---|
| Arg Leu Leu Gly Gly Val Glu Asn Ser Pro Val Ser Leu Gly Arg Ala |  |
|          130                 135                 140 |  |

| tgc tgg gcc agc acg agc acg gca cga aat aga tagcacgcag cccggcccag | 905 |
|---|---|
| Cys Trp Ala Ser Thr Ser Thr Ala Arg Asn Arg |  |
| 145                 150                 155 |  |

```
cacgaaacag aaaaaatcgg gccagcacga cacggtagac gggctgggcc gtgctctagc      965
tggtggcccg acgscccaaa tagcccggca cgccgtcgtg ggccgtgctc gggccagccc    1025
ggcacgattt agggttaggg ttcctatgac ggcggctctc ctcgtttttct ccgctcgctc    1085 tcgtccgctc gttctcttct gcgaccacag cgcgccgtcc accgctcgct ggcctctcgc    1145
gcctcagcac caagacttcg gcggcgggcc ctgctcctcc cagcgcgcca cctcgcgctc    1205
ctcgtgcacc cgccgaagtc ccagcaggcc agcacaccac ctcacgctcc tcccagcgag    1265
ccgccgaagt cccagcgcgc cacctcgcgc tccttccagc aagccgccgc gcaatcgagg    1325
acaagctgca ggcctacagc cgccggagcc caggcaatcg aggaccagct gcagccgtcg    1385
gagcctagtt ccggccatga tccccgcctc gcgccgtagc tgcgccgccg ccgccgccgg    1445
ccgacttgac ggccacgagc tcgccctcgc ccgccgcgac acgacggcgc ctgagaggag    1505
cacctgaagc actcttacgg gccgggtctg ggccagcacg gcacgatgca agcccaccgt    1565
gctttagggc cgtgctgggc ctatatttta agacgtgagc acgatatagc ccggctcgaa    1625
```

```
tgcatttcgt gctagcccgg cccgaagtat ttcagcccga agcacgacgg gcccgtgccg    1685
ggtcagcacg gcccggccca atttgcagga ctagtcgaga aggttatggc gtgccacatc    1745
aacggcaccc tcgtcccgct cctcaagcag gccggcgcgc tctggctctg atcgcgccgt    1805
cgccgtcgtc gtcgtcgatc ggccactgca aca                                 1838

<210> SEQ ID NO 15
<211> LENGTH: 1132
<212> TYPE: DNA
<213> ORGANISM: Zea mays

<400> SEQUENCE: 15
aattcgcggg acgtggcgtt gtcggctccg tgtcggcggc cgaaccacca cgaatcactg     60
acgtatctcg tctcctctct cctctagact cccacgatac ggccaacgaa gtgtatgtac    120
atatataccc atggtcatat ggcaacaaac gccaacgcca gcagagcact gcccggcggc    180 cttttttccca tctctctctc tctctctgat ggggtgtgca tgcctgactg actgatagat    240
agatagatgg tcaggtccgt ctgatcctca tcggcctagc tcaccccacg cgaaaaaagc    300
cactgctggc tggcgcccag ttgcgcttgc aacagtcact ttaacgagct ccgtccttgc    360
gtttgccctc ctcgctctgc ccctgccgcc gctgccgctg cgtggtggtg ctggtgcatg    420
aggcaggcag gcgtactagt gcatgcaatt gcaatgcaac cgtaggagtg cgttgcgtac    480
cctggtctgt ccctgcggcc tggcctgccc ttgttcgttg cggatgcggg gggtgccggg    540
tgggtactgt actgtactac tgggtagaga gatactacta gatagagaga gagagaggtc    600
ggtcaccccg ggcgcgggac acagcctctg cgaaaaagcg atccatgtcg cgcctagctt    660
tgacccggaa cggatccccc aaccaggaac cagcagagca ggagggccag gccaccacct    720
ctcgccattc cattcccggt cctagctagt cctgttctgt tcctgtagca gtagcagtag    780
ctacggtact acgagtcctc ctcgacgtcc caggcactac tccactccac gcagcagcag    840
gcagcgagca tctctcgacc agatgcatac aagctacacc ctcctcggct ccgatcctac    900
ccatgccggc ccaggcggcc tataaaagcg caccccggc ccgtcttcct cccactgcat    960
gcccattgcc cctcccccgg ccttcgccgt gccaacgaca cacctcatca ccggccgaa    1020 cattccacga ccgaagaaac cagtccctag ctagtccacg cacgaccaac aaggcaggcg   1080
agcgacgaca gtccaagcct ccaagaagaa gaagaagaag aagaagaaga ag           1132

<210> SEQ ID NO 16
<211> LENGTH: 2860
<212> TYPE: DNA
<213> ORGANISM: Oryza sativa

<400> SEQUENCE: 16
tggaacgcat ggcaagaagg gtagtagtac gccgtacgat cagacggtta cgcgtgatgt     60
aacgtgtcga cgatccatga tccatcgact aggaggtcat caccgggcc cacctgcccc    120 ccgggaggga ggttgcgttg gtgggcccgg gggagtcaaa cgacggcgga gatgagacgg    180
agagggcccc gccgttatgc tgtcgggctg tcggcgcttc acacagtggc cgtccgtacg    240
tgatgtcgcc tcctccagcc gtctccaagt acagctatac tagtagagta gtatactact    300
gctcctatac tgtacagtat accccgtact gtactagtgg caatatcact caaaacacat    360
ggagcattat gtatacatac aaccatcatg aatatatatt cttctagaaa cgaaaaaagc    420
atgcacatcg cccctatttt ggggagttag ttaattagaa tattcagctg ataggaatct    480
ttaaaagaat cggataatta attaaccata atttctgtca tgcagggtat caaatgtacc    540
```

| | |
|---|---|
| acattaaatt tttctagcaa tgtaaaatct atgcatgcac cacactggac agcgaaatat | 600 |
| atactcccett cgtactcata aagggaatcg ttttggacag tgacacggtc tccaaaacac | 660 |
| aactttgact ttttgtttct ataaaaatat ttattgaaaa gtgatatatg tatacttta | 720 |
| tgaaagtatt tttcaagaca aatctattca tatatttttt atattttcaa attcaataat | 780 |
| ttaaaaatta ttcatgattt atattctcaa ggtttgactt aaatattatc ctaaacgatt | 840 |
| ttctttatga gtacggaggg agtatactta caatttttgta cctctcgagt acgataaaat | 900 |
| ctctctccag attttgcgcg agaatatctg aacggtttgt agctgcatta tctagaagat | 960 |
| ctcttgaaaa tgaacatagt tcatatatta cctcatgtat gtggtgctat atatatatat | 1020 |
| gtttcactgg atggttaatt acttctggga aactgtttta acatgcaaca tgtactagct | 1080 |
| agctagctcc atttctcttc attccattcc agagagctcc tctatttctt ttactaatct | 1140 |
| ttttcccta tcaaaaagcc accagctttc tagtaagcaa cactagtcac tttaacctcc | 1200 |
| tcccttgctt ttgcttacta caccttgcat ctctctctgg taaccgtatc gtggtggaag | 1260 |
| gaaaggaaga aaggagtgta ctgggtagct cagctcagct cagctaggca gtggccatgt | 1320 |
| cagagcgtgt gttcgccgag ctcgcgacca tccactacca aaaagcctt ccatgtcgcc | 1380 |
| actcctttga ccccccctcgc accacaccaa ttctccatct atatatcatc caccttcttc | 1440 |
| ttcctcctct cattgccatt gtgtgtttgt gttacattgc aatcgtgcca tttgaagaag | 1500 |
| aggaggagag gatgaggatg caggtggtgg agacggcggc ggtggaggag gaggaggcgg | 1560 |
| cggcggcgat gatgtcggtg tacgagaggg tggcgaggat ggcgagcggg aacgcggtgg | 1620 |
| tggtgttcag cgcgagcggg tgctgcatgt gccacgtcgt caagcgcctc ctcctcggcc | 1680 |
| tcggcgtcgg ccccgccgtc tacgagctcg accagctcgc cgccgccgcc gacatccagg | 1740 |
| ccgcgctgtc gcagctcctc ccgccgggcc agccgccggt gcccgtcgtg ttcgtcggcg | 1800 |
| gcaggctcct cggcggcgtc gagaaggtga tggcgtgcca catcaatggc accctcgtcc | 1860 |
| ccctcctcaa gcaggccggc gccctctggc tctgatccat ccatcgatcc ctaccttgca | 1920 |
| ttgattaatg tatgatgctt aattaattaa tcaagatttt aatctatctc aaggaggagt | 1980 |
| ttgtagatat aattaattaa cagagtgatc tatcgcgatc tagcttagct taattaccta | 2040 |
| ggttggtgtg gtgtggtgtg ctgttgaatc ggttggttga ttagcgaaga gcatgcggtg | 2100 |
| tgttaattaa ttttaagcta cttgttggtc gacgatgagt ttgaaatgca atggaaatgc | 2160 |
| agtgctttta attaattgca tggtgtgtac gttgttcttg gctagctttt ccaaaacttg | 2220 |
| agtttgttta aaaggtgccg atcgatcaat gtgtcttcac tctgatcgat caaaaaagag | 2280 |
| aaaagagaga tacagtcata cagtagctag ctagcattac acagtctaaa gtttggcttc | 2340 |
| ttttaaacaa aaaaaataaa aaagcaaaga agcaaaagtt tggcttcttt tgaacgtaca | 2400 |
| gcatgaggca cgtagcgatg tatacgctat agtactattc gttcaaacta actgatggcc | 2460 |
| gtttcttact ttctttcttt gagctgatga gagttggttg cgagattctt tcatgtggcg | 2520 |
| tgaccgtttg atgaacaaat taaagctgca gtgtcgtcct tggttcatca tcgatcgaca | 2580 |
| aacacacaca cacacacaca cacattgcaa acaattaaca gatgattgtt gttggccgtc | 2640 |
| gtcatggtcg gtcagggcag agctagtgac agtcaaaagc aacgtatacg tatacgtatg | 2700 |
| taatggcgaa agcagcagca gctgctagct gctggttcta cagtgctttt aagtggctgg | 2760 |
| gtcagtcact gcatgcaatg caggcaaaag agctagctag aattgcatat atacatgatc | 2820 |
| tgagagaaag aaagagagag agatagagaa aattatttaa | 2860 |

<210> SEQ ID NO 17

<211> LENGTH: 192
<212> TYPE: PRT
<213> ORGANISM: Oryza sativa

<400> SEQUENCE: 17

```
Met Ser Glu Arg Val Phe Ala Glu Leu Ala Thr Ile His Tyr Gln Lys
  1               5                  10                  15
Ser Leu Pro Cys Arg His Ser Phe Asp Pro Pro Arg Thr Thr Pro Ile
             20                  25                  30
Leu His Leu Tyr Ile Ile His Leu Leu Pro Pro Leu Ile Ala Ile
         35                  40                  45
Val Cys Leu Cys Tyr Ile Ala Ile Val Pro Phe Glu Glu Glu Glu
     50                  55                  60
Arg Met Arg Met Gln Val Val Glu Thr Ala Ala Val Glu Glu Glu Glu
 65                  70                  75                  80
Ala Ala Ala Ala Met Met Ser Val Tyr Glu Arg Val Ala Arg Met Ala
                 85                  90                  95
Ser Gly Asn Ala Val Val Val Phe Ser Ala Ser Gly Cys Cys Met Cys
            100                 105                 110
His Val Val Lys Arg Leu Leu Leu Gly Leu Gly Val Gly Pro Ala Val
            115                 120                 125
Tyr Glu Leu Asp Gln Leu Ala Ala Ala Ala Asp Ile Gln Ala Ala Leu
        130                 135                 140
Ser Gln Leu Leu Pro Pro Gly Gln Pro Pro Val Pro Val Val Phe Val
145                 150                 155                 160
Gly Gly Arg Leu Leu Gly Gly Val Glu Lys Val Met Ala Cys His Ile
                165                 170                 175
Asn Gly Thr Leu Val Pro Leu Leu Lys Gln Ala Gly Ala Leu Trp Leu
            180                 185                 190
```

<210> SEQ ID NO 18
<211> LENGTH: 1316
<212> TYPE: DNA
<213> ORGANISM: Oryza sativa

<400> SEQUENCE: 18

```
tggaacgcat ggcaagaagg gtagtagtac gccgtacgat cagacggtta cgcgtgatgt      60
aacgtgtcga cgatccatga tccatcgact aggaggtcat caccgggggcc cacctgcccc     120
ccgggaggga ggttgcgttg gtgggcccgg ggagtcaaa cgacggcgga gatgagacgg      180
agagggcccc gccgttatgc tgtcgggctg tcggcgcttc acacagtggc cgtccgtacg      240
tgatgtcgcc tcctccagcc gtctccaagt acagctatac tagtagagta gtatactact      300
gctcctatac tgtacagtat accccgtact gtactagtgg caatatcact caaaacacat      360
ggagcattat gtatacatac aaccatcatg aatatatatt cttctagaaa cgaaaaaagc      420
atgcacatcg cccctattt ggggagttag ttaattagaa tattcagctg ataggaatct      480
ttaaaagaat cggataatta attaaccata atttctgtca tgcagggtat caaatgtacc      540
acattaaatt tttctagcaa tgtaaaatct atgcatgcac cacactggac agcgaaatat      600
atactccctt cgtactcata aagggaatcg ttttggacag tgacacggtc tccaaaacac      660
aactttgact ttttgtttct ataaaaatat ttattgaaaa gtgatatatg tatactttta      720
tgaaagtatt tttcaagaca aatctattca tatattttt atattttcaa attcaataat      780
ttaaaaatta ttcatgattt atattctcaa ggtttgactt aaatattatc ctaaacgatt      840
ttctttatga gtacggaggg agtatactta caattttgta cctctcgagt acgataaaat      900
```

| | |
|---|---:|
| ctctctccag attttgcgcg agaatatctg aacggtttgt agctgcatta tctagaagat | 960 |
| ctcttgaaaa tgaacatagt tcatatatta cctcatgtat gtggtgctat atatatatat | 1020 |
| gtttcactgg atggttaatt acttctggga aactgtttta acatgcaaca tgtactagct | 1080 |
| agctagctcc atttctcttc attccattcc agagagctcc tctatttctt ttactaatct | 1140 |
| ttttcccta tcaaaaagcc accagctttc tagtaagcaa cactagtcac tttaacctcc | 1200 |
| tcccttgctt ttgcttacta caccttgcat ctctctctgg taaccgtatc gtggtggaag | 1260 |
| gaaaggaaga aaggagtgta ctgggtagct cagctcagct cagctaggca gtggcc | 1316 |

<210> SEQ ID NO 19
<211> LENGTH: 3592
<212> TYPE: DNA
<213> ORGANISM: Oryza sativa

<400> SEQUENCE: 19

| | |
|---|---:|
| ttgtaaaacg acggccagtg aattgtaata cgactcacta tagggcgaat tgggccctct | 60 |
| agatgcatgc tcgagcggcc gccagtgtga tggatatctg cagaattcgc cctttgagca | 120 |
| tgcatgctaa gctagtactc cagctggtag cttttggtaa gcttatcata tccatcacgt | 180 |
| cacatatatc atatatgcat gatttcttgc tacctcgcca ctagcttttg ctgaaacggt | 240 |
| ttttatattg gagaaacacg acaccgcatg catgcatgtg ccatgtacga aatttggccc | 300 |
| cgtttagttc ccaaaagttt ttcccaaaat catcacatcg aattcttgga tatatgcatg | 360 |
| gagcattaaa tataaattaa aagaaaaact aattacacag ttaagggggga aatcgcgaga | 420 |
| caaatatttt gagcttaatt tgttcatgat tagccataag tgctacagta acccacatgt | 480 |
| gctaatgatg gattaattag gctcaaaaga ttcgtctcgc ggtttccatg cgagttacga | 540 |
| aattagtttt tcatttgtg tccgaaaacc ccttctgaca ttcggtcaaa catccgatgt | 600 |
| gacacccaaa aaattttatt tcacgactaa acatgccctt gtttcataaa tttaagttgc | 660 |
| ttttcatgca tgcaaaccaa agtaaactac tgtagcttag taaatttgca aacttcgcct | 720 |
| ttttcccccca gtggagatgc atgcatgcga cgcattaatg atcgacatat atatgtcgat | 780 |
| cattaactga tgatcactga tcatatcgat agaaatcata agattgatgt tgtgttgta | 840 |
| accagggttt accttaccgc cggggccggg gttaccgtgc cccggcggta agcacggtta | 900 |
| ccgcgcggta accgcggtaa ccgtgaaaaa ccgtacaaaa ccgtgcaaaa tttatcaaaa | 960 |
| attcaaatta ttttttaaat ttatttgtat ttaaggaggt taccgcggta tttatattac | 1020 |
| cgtaccccg cggtaagccc ggtaaccgcg cggttaccgg cggtaagtta aaccctggtt | 1080 |
| gtaactcgca gtggttgtca ttgtgaatcg gccgatacaa tacgtcaata tgatcataga | 1140 |
| cgcgactttg ttaatccatc atatatatct caatcgatct gcaatatgtg tgtgaaccgt | 1200 |
| gtgcatgtcg tcgaatcttt gacaacatct atcgatatcg atctcctcag atggatcgat | 1260 |
| cgatatcata tgaacaatgc attgcagcgg tgggccatca cagggcatgc atgcaaccat | 1320 |
| gcaaggcacc agctaccttc tattttggca tgcatttcat tactacgcca tgcaattaac | 1380 |
| ccagagagac agcgtctcaa ctagcaacat actctctccg tctcaaaata taagatattt | 1440 |
| tagttggatg tgacattctt agtactccct ccatccacaa aagttagaca tatttcacat | 1500 |
| ttgagttttt ccaaataagt tgttcctatt tgtagtcttt atgtatttaa gacttaaatg | 1560 |
| aagagataaa ttaaatgttt tatgagaacc caaggagtca tccaaatact cattggttgc | 1620 |
| atgcttgcat tcactccttg attttgtaac atccaagaag attttaattc tcattggtct | 1680 |
| ttgtgacaaa agtaatatgc gtaacttttg tggatggagg gagtactacg aatctgaaca | 1740 |

```
ggcagtagta ctaggataca tgtgtcacat ctatctaaaa tctctcttat tttgggacgg    1800
atggagtata ctccctccgt actcctaaag gaagtcgttt aggacagcga catggtctcc    1860
aaaacacaac tttgacttct tgtttctata aaatatttta ttgaaaagtg atatatgtat    1920
acttttatga aagtattttt caagacaaat ctattcatat aatttttaca ttttcaaaat    1980
caataacttg agagttattc gtgatttata ttcctaaggt ttgacttaaa cattatccta    2040
aacgactttc tttatgagta caatgagtac agagggagta ttaattaatc aatcgaggga    2100
ctggaccagc caatagatat atatgatgtg gccaagctga aattaaatta tgtctgtacc    2160
taaagcatgc ataattaatg aacattatgt atagtaagag cgagtttaat agtagagcta    2220
attattggct aatagcctat tttagatcta acatgtataa taagttatca ttcctcattt    2280
ctctctcaca taagcttata gtacgggctt atattccact attatccttg ctctaaagca    2340
taatatatgt cttgctcgta gtgtggagtg tggaaatgta gagtatgaaa agagagagaa    2400
aaaacaggca agagaaaaac ctatgagaaa aaaccataat tcacatgcat atacacttaa    2460
acaaaaaacg aatagacatt gtaacccctta attcttgtaa tctaattaag tgctatataa    2520
ttcaaaaaac aatcaacgta ttcatgatat atttaaaatt ctaatatttta taatatgaat    2580 aaatgataac ccagtcatgc aatgtgaacg agttgataac tcgtttaaga aaaaaataa    2640 taataaggta ttgtgcttct taattcaacg gaagcacctc acatatatca atacaaaact    2700
aatcaaaaag actaaactac cctcatttta ttaaattcca atgcaattat tccactcctt    2760
atcaattccc aacacatttt tatccatcca tcgatcccta ccttgcattg attaatgtgt    2820
gatgcttaat taattaatca agattttaat ctacctcaag gaggagtttg tagatataat    2880
taattaacag agtgatctat cgcgatctag cttagcttaa tcacctaggt tggtgtggtg    2940
tggtgtgctg ttgaatcggt tggttaatta gcgaagagca tgcggtgtgt taattaattt    3000
taagctactt gttggtcgac gatgagtttg aaatgcaatg gaaatgcagt gcttttaatt    3060
aattgcatgg tgtgtacgtt gttcttggct agcttttcca aaacttgagt ttgtttaaaa    3120
ggtgccgatc gatcaatgtg tcttcactct gatcgatcaa aaaagagaaa agagagatac    3180
agtcatacag tagctagcta gcaatacaca gtctgaagtt tggcttcatt taaacaaaaa    3240
aaataaaaaa gcaaagaagc aaaagtttgg cttcttttga acgtacagca tgaggcacgt    3300
agcgatgtat acgctatagt actattcgtt caaactaact gatggccgtt tcttactttc    3360
tttctttgag ctgatgagag ttggttgcga gattctttca tgtggcatga ccgtcatttc    3420
cacagttcag tcactgaagc ttgacttgaa aatgaacatc agtcaacagg acaaaaaaa    3480 aaattacgga ccaaataacg cctgttatta tcctactaaa aatcgtcttc gttgtcacca    3540
tcagagagga tcacaagggc gaattccagc acactggcgg ccgttactag tg           3592
```

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgagcatgca tgctaagcta gtactccagc                                      30

<210> SEQ ID NO 21
<211> LENGTH: 30
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 21
gtgatcctct ctgatggtga caacgaagac                                         30

<210> SEQ ID NO 22
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tatatatata ta                                                            12

<210> SEQ ID NO 23
<211> LENGTH: 159
<212> TYPE: PRT
<213> ORGANISM: Zea mays

<400> SEQUENCE: 23

Met Leu Arg Met Glu Val Gln Gln Gln Gln Glu Ser Gly Val Ser
  1               5                  10                  15

Gly Gly Val Val Ala Asp Ala Ala Ala Ser Gly Ala Asp Ala Ala
                 20                  25                  30

Pro Thr Thr Thr Thr Met Val Ala Ala Pro His Ser Ala Ser Ala
                 35                  40                  45

Leu Ala Val Tyr Glu Arg Val Ala Arg Met Ala Gly Gly Asn Ala Val
                 50                  55                  60

Val Val Phe Ser Ala Ser Gly Cys Cys Met Cys His Val Val Lys Arg
 65                  70                  75                  80

Leu Leu Leu Gly Leu Gly Val Gly Pro Thr Val Tyr Glu His Asp Gln
                 85                  90                  95

Met Ala Ala Gly Gly Gly Gly Arg Glu Ile Gln Ala Ala Leu Ala
                100                 105                 110

Gln Leu Leu Pro Pro Gly Gln Pro Pro Leu Pro Val Val Phe Val Gly
                115                 120                 125

Gly Arg Leu Leu Gly Gly Val Glu Lys Val Met Ala Cys His Ile Asn
                130                 135                 140

Gly Thr Leu Val Pro Leu Leu Lys Gln Ala Gly Ala Leu Trp Leu
145                 150                 155

<210> SEQ ID NO 24
<211> LENGTH: 155
<212> TYPE: PRT
<213> ORGANISM: Zea mays

<400> SEQUENCE: 24

Met Leu Arg Met Glu Val Gln Gln Gln Gln Glu Ser Gly Val Ser
  1               5                  10                  15

Gly Gly Val Val Ala Asp Ala Ala Ala Gly Ser Val Ala Asp Ala Ala
                 20                  25                  30

Thr Thr Thr Thr Thr Met Val Ala Ala Pro His Ser Ala Ser Ala
                 35                  40                  45

Leu Ala Val Tyr Glu Arg Val Ala Arg Met Ala Gly Gly Asn Ala Val
                 50                  55                  60

Val Val Phe Ser Ala Ser Gly Cys Cys Met Cys His Val Val Lys Arg
```

```
                65                  70                  75                  80
Leu Leu Leu Gly Leu Gly Val Gly Pro Thr Val Tyr Glu Leu Asp Gln
                    85                  90                  95

Met Ala Ala Gly Gly Gly Gly Arg Glu Ile Gln Ala Ala Leu Ala Gln
                100                 105                 110

Leu Leu Pro Pro Gly Gln Pro Pro Leu Pro Val Val Phe Val Gly Gly
            115                 120                 125

Arg Leu Leu Gly Gly Val Glu Asn Ser Pro Val Ser Leu Gly Arg Ala
        130                 135                 140

Cys Trp Ala Ser Thr Ser Thr Ala Arg Asn Arg
145                 150                 155

<210> SEQ ID NO 25
<211> LENGTH: 12
<212> TYPE: PRT
<213> ORGANISM: Oryza sativa

<400> SEQUENCE: 25

Val Pro Val Val Phe Val Gly Gly Arg Leu Leu Gly
 1               5                  10
```